US012686715B2

(12) United States Patent
Li et al.

(10) Patent No.: US 12,686,715 B2
(45) Date of Patent: Jul. 21, 2026

---

(54) METHODS FOR TREATMENT OF B CELL PROLIFERATIVE DISORDERS WITH ANTI-CD20/ANTI-CD3 BISPECIFIC ANTIBODIES

(71) Applicant: Genentech, Inc., South San Francisco, CA (US)

(72) Inventors: Chi-Chung Li, South San Francisco, CA (US); Carol Elaine O'Hear, South San Francisco, CA (US); Xi Chen, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 1025 days.

(21) Appl. No.: 17/829,807

(22) Filed: Jun. 1, 2022

(65) Prior Publication Data

US 2022/0380466 A1     Dec. 1, 2022

Related U.S. Application Data

(60) Provisional application No. 63/195,677, filed on Jun. 1, 2021.

(51) Int. Cl.
| | |
|---|---|
| *A61P 35/02* | (2006.01) |
| *C07K 16/28* | (2006.01) |
| *A61K 39/00* | (2006.01) |

(52) U.S. Cl.
CPC .......... *C07K 16/2809* (2013.01); *A61P 35/02* (2018.01); *C07K 16/2887* (2013.01); *A61K 2039/505* (2013.01); *A61K 2039/545* (2013.01); *C07K 2317/31* (2013.01); *C07K 2317/565* (2013.01); *C07K 2317/92* (2013.01)

(58) Field of Classification Search
CPC . A61P 35/02; C07K 16/2809; C07K 16/2887; C07K 2317/31
USPC ....................................................... 424/144.1
See application file for complete search history.

(56) References Cited

U.S. PATENT DOCUMENTS

| | | | |
|---|---|---|---|
| 8,895,702 B2 | 11/2014 | Williams et al. | |
| 10,357,571 B2 | 7/2019 | Williams et al. | |
| 11,466,094 B2 * | 10/2022 | Chu ................... | A61K 39/3955 |
| 12,351,643 B2 * | 7/2025 | Li ...................... | C07K 16/2887 |
| 12,492,261 B2 * | 12/2025 | Li ...................... | C07K 16/2809 |
| 2009/0304719 A1 | 12/2009 | Daugherty et al. | |
| 2011/0178279 A1 | 7/2011 | Williams et al. | |
| 2013/0266568 A1 | 10/2013 | Brinkmann et al. | |
| 2015/0166661 A1 | 6/2015 | Chen et al. | |
| 2015/0266966 A1 | 9/2015 | Smith et al. | |
| 2016/0152711 A1 | 6/2016 | Williams et al. | |
| 2016/0194399 A1 | 7/2016 | Irving et al. | |
| 2017/0218074 A1 | 8/2017 | Williams et al. | |
| 2018/0134798 A1 | 5/2018 | Chu et al. | |
| 2018/0148508 A1 | 5/2018 | Wang et al. | |

| | | | |
|---|---|---|---|
| 2018/0193479 A1 | 7/2018 | Williams et al. | |
| 2020/0164077 A1 | 5/2020 | Williams et al. | |
| 2020/0199578 A1 | 6/2020 | Short et al. | |
| 2022/0153842 A1 | 5/2022 | Li et al. | |
| 2022/0153858 A1 * | 5/2022 | Li ........................... | A61P 35/02 |
| 2022/0162329 A1 * | 5/2022 | Li ........................ | A61K 31/573 |
| 2023/0416391 A1 | 12/2023 | Huang et al. | |
| 2025/0043019 A1 * | 2/2025 | Ganesan ............ | C07K 16/2887 |
| 2025/0171552 A1 * | 5/2025 | Chu ................... | C07K 16/2827 |

FOREIGN PATENT DOCUMENTS

| | | |
|---|---|---|
| CN | 102369218 A | 3/2012 |
| JP | 2015-509951 A | 4/2015 |
| JP | 2015-509952 A | 4/2015 |
| JP | 2018-527887 A | 9/2018 |
| TW | 201508008 A | 3/2015 |
| WO | WO-2005/083431 A2 | 9/2005 |
| WO | WO-2007/005874 A2 | 1/2007 |
| WO | WO-2009/106321 A1 | 9/2009 |
| WO | WO-2011/028945 A1 | 3/2011 |
| WO | WO-2011/121110 A1 | 10/2011 |
| WO | WO-2012/025525 A1 | 3/2012 |
| WO | WO-2013/128027 A1 | 9/2013 |
| WO | WO-2013/128194 A1 | 9/2013 |
| WO | WO-2018/093821 A1 | 9/2013 |
| WO | WO-2015/095392 A1 | 6/2015 |
| WO | WO-2016/019969 A1 | 2/2016 |
| WO | WO-2016/081490 A1 | 5/2016 |
| WO | WO-2016/090210 A1 | 6/2016 |
| WO | WO-2016/110576 A1 | 7/2016 |
| WO | WO-2016/205520 A1 | 12/2016 |
| WO | WO-2022/098648 A2 | 5/2022 |
| WO | WO-2023/234933 A1 | 12/2023 |

OTHER PUBLICATIONS

NCT05207670 (clinicaltrials.gov; pp. 1-12 (Jan. 26, 2022)).*
NCT03677154 (clinicaltrials.gov; pp. 1-13 ( Sep. 19, 2018)).*
cancer.gov/publications/dictionaries/cancer-terms/def/monotherapy defintion of monotherapy (p. 1 (Dec. 8, 2025)).*
healthjournalism.org/glossary-terms/monotherapy definition of monotherapy (pp. 1-2 (Dec. 8, 2025)).*
merriam-webster.com/medical/monotherapy definition of monotherapy (p. 1 (Dec. 8, 2025)).*
U.S. Appl. No. 19/384,232, Li; Chi-Chung.*
U.S. Appl. No. 19/225,548, Li; Chi-Chung.*
U.S. Appl. No. 19/305,991, Chu: Yu-Waye.*

(Continued)

*Primary Examiner* — Lynn A Bristol

(74) *Attorney, Agent, or Firm* — Clark & Elbing LLP; Karen L. Elbing

(57)     ABSTRACT

The present invention relates to the treatment of subjects having B cell proliferative disorders, including high grade B-cell lymphomas, as well as non-Hodgkin's lymphomas, such as diffuse large B-cell lymphomas. More specifically, the invention pertains to the treatment of subjects having a B cell proliferative disorder by intravenous administration of an anti-CD20/anti-CD3 bispecific antibody.

26 Claims, 12 Drawing Sheets
Specification includes a Sequence Listing.

(56) References Cited

OTHER PUBLICATIONS

Budde et al., "Single-Agent Mosunetuzumab Shows Durable Complete Responses in Patients With Relapsed or Refractory B-Cell Lymphomas: Phase I Dose-Escalation Study," J Clin Oncol. 40(5):481-91 (Dec. 16, 2021) (15 pages).

"History of Changes for Study: NCT02500407: A Safety, Efficacy and Pharmacokinetic Study of BTCT4465A (Mosunetuzumab) as a Single Agent and Combined With Atezolizumab in Non- Hodgkin's Lymphoma (NHL) and Chronic Lymphocytic Leukemia (CLL) ," ClinicalTrials.gov, last updated Mar. 17, 2022, retrieved Jul. 17, 2023, from <https://classic.clinicaltrials.gov/ct2/history/NCT02500407?V_74=View#StudyPageTop> (10 pages).

Budde et al., "Mosunetuzumab, a Full-Length Bispecific CD20/CD3 Antibody, Displays Clinical Activity in Relapsed/Refractory B-Cell Non-Hodgkin Lymphoma (NHL): Interim Safety and Efficacy Results from a Phase 1 Study," Blood. 132(Supplement 1):399 (2018) (6 pages).

Buhmann et al., "Immunotherapy of recurrent B-cell malignancies after allo-SCT with Bi20 (FBTA05), a trifunctional anti-CD3 x anti-CD20 antibody and donor lymphocyte infusion," Bone Marrow Transplant. 43(5):383-97 (2009).

Buhmann et al., "Immunotherapy with FBTA05 (Bi20), a trifunctional bispecific anti-CD3 x anti-CD20 antibody and donor lymphocyte infusion (DLI) in relapsed or refractory B-cell lymphoma after allogeneic stem cell transplantation: study protocol of an investigator-driven, open-label, nonrandomized, uncontrolled, dose-escalating Phase I/II-trial," J Transl Med. 11:160 (2013) (9 pages).

Chu et al., "Immunotherapy with long-lived anti-CD20 x anti-CD3 bispecific antibodies stimulates potent T cell-mediated killing of Human B cell lines and of circulating and lymphoid B cells in monkeys: a potential therapy for B cell lymphomas and leukemias," Blood. 124(21):3111 (2014) (1 page).

Desnoyers et al., "Tumor-specific activation of an EGFR-targeting probody enhances therapeutic index," Sci Transl Med. 5(207):207ra144 (2013) (2 pages) (Abstract only).

Diefenbach et al., "An individualized risk mitigation approach for safety: experience from the mosunetuzumab (CD20/CD3 bispecific antibody) development program in relation to neurotoxicity risk," 61st ASH Annual Meeting & Exposition, Dec. 7-10, Orlando, Florida, Poster P-4728 (2019) (1 page).

Donaldson et al., "Design and development of masked therapeutic antibodies to limit off-target effects: application to anti-EGFR antibodies," available in PMC Jan. 16, 2013, published in final edited form as: Cancer Biol Ther. 8(22): 2147-52 (2009) (12 pages).

Erster et al., "Site-specific targeting of antibody activity in vivo mediated by disease-associated proteases," J Control Release. 161(3): 804-12 (2012) (2 pages) (Abstract only).

Gaston et al., "Intracellular delivery of therapeutic antibodies into specific cells using antibody-peptide fusions," Sci Rep. 9(1):18688 (2019) (12 pages).

Goebeler et al., "Bispecific T-cell Engager (BiTE) Antibody Construct Blinatumomab for the Treatment of Patients With Relapsed/Refractory Non-Hodgkin Lymphoma: Final Results From a Phase I Study," J Clin Oncol. 34(10):1104-11 (2016) (13 pages).

Haile et al., "Soluble CD80 Restores T Cell Activation and Overcomes Tumor Cell Programmed Death Ligand 1-Mediated Immune Suppression," J Immunol. 191(5):2829-36 (2013) (9 pages).

Han et al., "Masked Chimeric Antigen Receptor for Tumor-Specific Activation," Mol Ther. 25(1):274-84 (2017).

Hernandez et al., "Pharmacodynamic Effects and Immune Correlates of Response to the CD20/CD3 Bispecific Antibody Mosunetuzumab in Relapsed or Refractory Non-Hodgkin Lymphoma," Blood. 134(Supplement 1):1585 (2019) (4 pages).

Hosseini et al., "Abstract B043: Systems pharmacology modeling of anti-CD20/CD3 T-cell dependent bispecific antibody and its application to clinical trial design," Proceedings of the Second CRI-CIMT-EATI-AACR International Cancer Immunotherapy Conference: Translating Science into Survival; September 25-28; New York, NY. Cancer Immunol Res. 4(11 Suppl):Abstract nr B043 (2016) (4 pages).

Hosseini et al., "Mitigating The Risk Of Cytokine Release Syndrome In A Phase I Trial Of CD20/CD3 Bispecific Antibody Mosunetuzumab In NHL: Impact Of Translational System Modeling," NPJ Syst Biol Appl. 6(1):28 (2020) (11 pages).

Hosseini et al., "Systems pharmacology modeling of anti-CD20/CD3 T-cell dependent bispecific antibody and its application to clinical trial design," American Conference on Pharmacometrics 7; Oct. 25; Bellevue, WA. (2016) (1 page).

Huang, "Structural chemistry and therapeutic intervention of protein-protein interactions in immune response, human immunodeficiency virus entry, and apoptosis," Pharmacol Ther. 86(3):201-215 (2000).

Lee et al., "Current concepts in the diagnosis and management of cytokine release syndrome," Blood. 124(2):188-95 (2014) (18 pages).

Li et al., "Exposure-response analyses indicate a promising benefit/risk profile of mosunetuzumab in relapsed and refractory non-Hodgkin lymphoma," 61st ASH Annual Meeting & Exposition, Dec. 7-10, 2019, Orlando, Florida. Poster P-1285 (2019) (1 page).

Li et al., "Exposure-response analyses indicate a promising benefit/risk profile of mosunetuzumab in relapsed and refractory non-Hodgkin lymphoma," Blood. 134(Supplement 1):1285 (2019) (8 pages).

Li, "Successful QSP modeling in drug development starts with the right questions," American Conference on Pharmacometrics 8, Oct. 16, Fort Lauderdale, FL. (2017) (20 pages).

Lord et al., "Structure-based engineering to restore high affinity binding of an isoform-selective anti-TGFβ1 antibody," MAbs. 10(3):444-452 (2018) (10 pages).

Lu et al., "Tetravalent anti-CD20/CD3 bispecific antibody for the treatment of B cell lymphoma," Biochem Biophys Res Commun. 473(4):808-813 (2016) (Abstract only) (3 pages).

Mariuzza et al., "The structural basis of antigen-antibody recognition," Annu Rev Biophys Biophys Chem. 16:139-159 (1987) (2 pages) (Abstract only).

Milne et al., "Systematic Analysis of Immune Infiltrates in High-Grade Serous Ovarian Cancer Reveals CD20, FoxP3 and TIA-1 as Positive Prognostic Factors," PLoS One. 4(7):e6412 (2009) (14 pages).

NIH/NCI, "anti-PD-1 fusion protein AMP-224," dated Jul. 10, 2015, accessed Jul. 31, 2019 (1 page).

Nishimoto et al., "Toxicity, pharmacokinetics, and dose-finding study of repetitive treatment with the humanized anti-interleukin 6 receptor antibody MRA in rheumatoid arthritis. Phase I/II clinical study," J Rheumatol. 30(7):1426-35 (2003).

Olszewski et al., "401 Single-agent mosunetuzumab is a promising safe and efficacious chemotherapy-free regimen for elderly/unfit patients with previously untreated diffuse large B-cell lymphoma," 62nd American Society of Hematology (ASH) Annual Meeting and Exposition, Dec. 5-8, Oral Abstract, <https://ash.confex.com/ash/2020/webprogram/Paper136255.html>, retrieved on Apr. 21, 2022 (2020) (4 pages).

Paino et al., "Reply to 'Response to "CD20 Positive Cells Are Undetectable in the Majority of Multiple Myeloma Cell Lines and Are Not Associated With a Cancer Stem Cell Phenotype,""" Haematologica. 97(7):1110-1114 (2012) (1 page).

Polu et al., "Probody therapeutics for targeting antibodies to diseased tissue," Expert Opin Biol Ther. 14(8):1049-53 (2014).

"Purified Mouse Anti-Human CD3epsilon Clone SP34," Bd Biosciences, ,https://www.bdbiosciences.com/us/reagents/research/antibodies-buffers/immunology-reagents/anti-non-human-primate-antibodies/cellsurface-antigens/purified-mouse-anti-human-cd3-sp34/p/556610>, retrieved on Jan. 4, 2021 (4 pages).

Reusch et al., "Anti-CD3 x anti-epidermal growth factor receptor (EGFR) bispecific antibody redirects T-cell cytolytic activity to EGFR-positive cancers in vitro and in an animal model," Clin Cancer Res. 12(1):183-190 (2006) (9 pages).

Salmerón et al., "A conformational epitope expressed upon association of CD3-epsilon with either CD3-delta or CD3-gamma is the main target for recognition by anti-CD3 monoclonal antibodies," J Immunol. 147(9): 3047-52 (1991) (2 pages) (Abstract only).

Schuster et al., "Immunotherapy with the trifunctional anti-CD20 x anti-CD3 antibody FBTA05 (Lymphomun) in paediatric high-risk patients with recurrent CD20-positive B cell malignancies," Br J Haematol. 169:90-102 (2015).

(56)                    References Cited

OTHER PUBLICATIONS

Schuster et al., "Mosunetuzumab Induces Complete Remissions in Poor Prognosis Non-Hodgkin Lymphoma Patients, Including Those Who Are Resistant to or Relapsing After Chimeric Antigen Receptor T-Cell (CAR-T) Therapies, and Is Active in Treatment through Multiple Lines," Blood. 134 (Supplement 1):6 (2019) (5 pages).

Shi et al., "Margin-Infiltrating CD20⁺ B Cells Display an Atypical Memory Phenotype and Correlate with Favorable Prognosis in Hepatocellular Carcinoma," Clin Cancer Res. 19(21):5994-6005 (2013) (13 pages).

Somasundaram et al., "Will Engineered T Cells Expressing CD20 scFv Eradicate Melanoma?" Mol Ther. 19(4):638-40 (2011).

Stein et al., "Novel and Emerging Drugs for Acute Myeloid Leukemia," available in PMC May 22, 2014, published in final edited form as: Curr Cancer Drug Targets. 12(5):522-530 (2012) (19 pages).

Stieglmaier et al., "Utilizing the BiTE (bispecific T-cell engager) platform for immunotherapy of cancer," Expert Opin Biol Ther. 15(8):1093-9 (2015) (8 pages).

Sun et al., "Anti-CD20/CD3 T cell-dependent bispecific antibody for the treatment of B cell malignancies," Sci Transl Med. 7(287):287ra70 (2015) (11 pages).

Wells et al., "Reaching for high-hanging fruit in drug discovery at protein-protein interfaces," Nature. 450(7172):1001-9 (2007).

Yang et al., "Generation and characterization of a target-selectively activated antibody against epidermal growth factor receptor with enhanced anti-tumor potency," MAbs. 7(2):440-50 (2015).

International Preliminary Report on Patentability for International Patent Application No. PCT/US2017/061683, issued May 21, 2019 (7 pages).

International Search Report and Written Opinion for International Patent Application No. PCT/US2017/061683, mailed Feb. 23, 2018 (14 pages).

Invitation to Pay Additional Fees and, Where Applicable, Protest Fee for International Patent Application No. PCT/US2022/31621, mailed Aug. 22, 2022 (2 pages).

Katz et al., "Progress in development of the index of ADL," Gerentologist. 10(1):20-30 (1970).

Lawton et al., "Assessment of older people: self-maintaining and instrumental activities of daily living," Gerontologist. 9(3):179-186 (1969).

Lee et al., "ASTCT Consensus Grading for Cytokine Release Syndrome and Neurologic Toxicity Associated with Immune Effector Cells," Biology of Blood and Marrow Transplantation. 25(4):625-638 (Apr. 2019).

Olszewski et al., "Mosunetuzumab Monotherapy Continues to Demonstrate Promising Efficacy and Durable Complete Responses in Elderly/Unfit Patients with Previously Untreated Diffuse Large B-Cell Lymphoma," Blood. 140(Supplement 1):1778-1780 (Nov. 2022) (7 pages).

Castellino et al., "Follicular lymphoma: The Management of Elderly Patient," Mediterr J Hematol Infect Dis 9(1):1-13 e2017009 (Jan. 2017) (14 pages).

Presley et al., "Immunotherapy in Older Adults with Cancer," J Clin Oncol. 39(19):2115-2127 (May 2021) (14 pages).

Viardot et al., "Phase 2 study of the bispecific T-cell engager (BiTE) antibody blinatumomab in relapsed/refractory diffuse large B-cell lymphoma," Blood. 127(11):1410-6 (Jan. 2016) (7 pages).

Wang et al., "Ethnic variations in diagnosis, treatment, socioeconomic status, and survival in a large population-based cohort of elderly patients with non-Hodgkin lymphoma," Cancer 113(11):3231-3241 (Oct. 2008) (12 pages).

* cited by examiner

Note: D1, D8, and D15 refers to Day 1, Day 8,
and Day 15, respectively in
the above figure and legend

| Characteristic | No treatment* (n=57) | R-Benda (n=56) | R-CHOP (n=59) | R-CVP (n=58) | R-Len (n=2) | R-mono (n=57) | Reduced-dose R-CHOP (n=115) |
|---|---|---|---|---|---|---|---|
| Median age at diagnosis, years (IQR)# | 79.0 (76.0, 81.0) | 79.0 (77.0, 81.0) | 75.0 (73.0, 78.0) | 79.0 (77.0, 80.8) | 81.5 (80.8, 82.2) | 79.0 (76.0, 82.0) | 80.0 (79.0, 83.0) |
| Sex, n (%) Female | 35 (61) | 30 (54) | 24 (41) | 28 (48) | 1 (50) | 29 (51) | 48 (42) |
| Ann Arbor Stage | | | | | | | |
| I | 7 (12) | 2 (3.6) | 8 (14) | 2 (3.4) | 0 (0) | 8 (14) | 7 (6.1) |
| II | 1 (1.8) | 8 (14) | 12 (20) | 6 (10) | 0 (0) | 6 (11) | 20 (17) |
| III | 4 (7.0) | 12 (21) | 20 (34) | 12 (21) | 0 (0) | 7 (12) | 23 (20) |
| IV | 13 (23) | 12 (21) | 14 (24) | 5 (26) | 0 (0) | 20 (35) | 30 (26) |
| Unknown/not documented | 32 (56) | 22 (39) | 5 (8.5) | 23 (40) | 2 (100) | 16 (28) | 35 (30) |
| Extranodal involvement, n (%) | 33 (58) | 32 (57) | 32 (54) | 27 (47) | 0 (0) | 38 (67) | 59 (51) |
| CCI score on or prior to 1L therapy, median (IQR) | 0.00 (0.00, 0.00) | 1.00 (0.00, 2.25) | 1.00 (0.00, 2.00) | 1.00 (0.00, 2.00) | 1.00 (0.50, 1.50) | 2.00 (0.00, 4.00) | 1.00 (0.00, 3.00) |
| CCI score categories, n (%) | | | | | | | |
| 0–1 | 57 (100) | 35 (62) | 40 (68) | 36 (62) | 1 (50) | 26 (46) | 64 (56) |
| ≥2 | 0 (0) | 21 (38) | 19 (32) | 22 (38) | 1 (50) | 31 (54) | 51 (44) |

*Pts with no record of any systemic treatment or radiotherapy. #To protect pt privacy, the exact age for all patients >85 years is indicated as 85 years in the Flatiron Health database. CCI, Charlson Comorbidity Index; IQR, interquartile range.

FIG. 2

Number at risk

| | | | | |
|---|---|---|---|---|
| 59 | 29 | 13 | 8 | 1 |
| 115 | 32 | 12 | 2 | 0 |
| 58 | 23 | 9 | 3 | 0 |
| 56 | 17 | 6 | 1 | 0 |
| 57 | 18 | 7 | 4 | 2 |
| 57 | 6 | 2 | 1 | 0 |

| Treatment group¥ | Median OS, months (95% CI) |
|---|---|
| Number of events: 191 | |
| R-CHOP (n=59) | 92 (92-NR) |
| Reduced dose R-CHOP (n=115) | 36 (23-NR) |
| R-CVP (n=58) | 29 (17-61) |
| R-Benda (n=56) | 18 (13-75) |
| R-mono (n=57) | 13 (9-40) |
| No treatment (n=57)** | 7 (3-NR) |

| Treatment group* | Median OS, months (95% CI) |
|---|---|
| Number of events: 166 | |
| R-CHOP (n=59) | 91 (91-NR) |
| Reduced dose R-CHOP (n=115) | 37 (21-NR) |
| R-CVP (n=58) | 29 (16-57) |
| R-Benda (n=56) | 16 (12-46) |
| R-mono (n=57) | 11 (7-31) |

| Treatment group | Number of documented rationales | Treatment rationale, n (%)* | | | | | | | |
|---|---|---|---|---|---|---|---|---|---|
| | | Age | Comorbidity | Patient request | Disease burden | IPI for DLBCL | PS | Other | No rationale stated |
| Total (N=404)** | 437 | 99 (23.8) | 70 (16.8) | 20 (4.3) | 18 (4.8) | 0 | 49 (11.7) | 10 (2.4) | 148 (35.6) |
| R-CHOP (n=59) | 61 | ≤4‡ | ≤4‡ | ≤4‡ | 0 | 0 | ≤4‡ | ≤4‡ | 51 (83.6) |
| Reduced-dose R-CHOP (n=115) | 139 | 41 (29.5) | 22 (15.8) | ≤4‡ | 7 (5.0) | ≤4‡ | 13 (9.4) | ≤4‡ | 46 (33.1) |
| R-mono (n=57) | 73 | 21 (28.7) | 11 (15.1) | 9 (12.3) | 6 (8.2) | 0 | 14 (19.2) | ≤4‡ | 11 (15.1) |
| R-Benda (n=56) | 64 | 12 (18.8) | 15 (23.4) | ≤4‡ | ≤4‡ | 0 | 7 (10.9) | ≤4‡ | 23 (35.9) |
| R-CVP (n=58) | 76 | 22 (28.9) | 20 (26.3) | ≤4‡ | ≤4‡ | 0 | 12 (15.8) | 0 | 17 (22.4) |
| No treatment# (n=57) | 24 | ≤4‡ | 5 (21) | 7 (29) | ≤4‡ | 0 | ≤4‡ | ≤4‡ | ≤4‡ |

FIG. 6

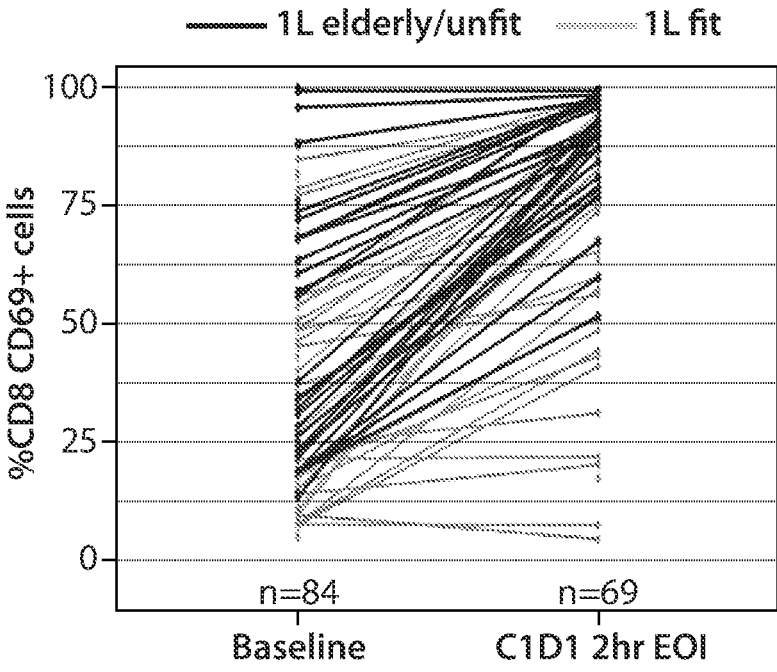
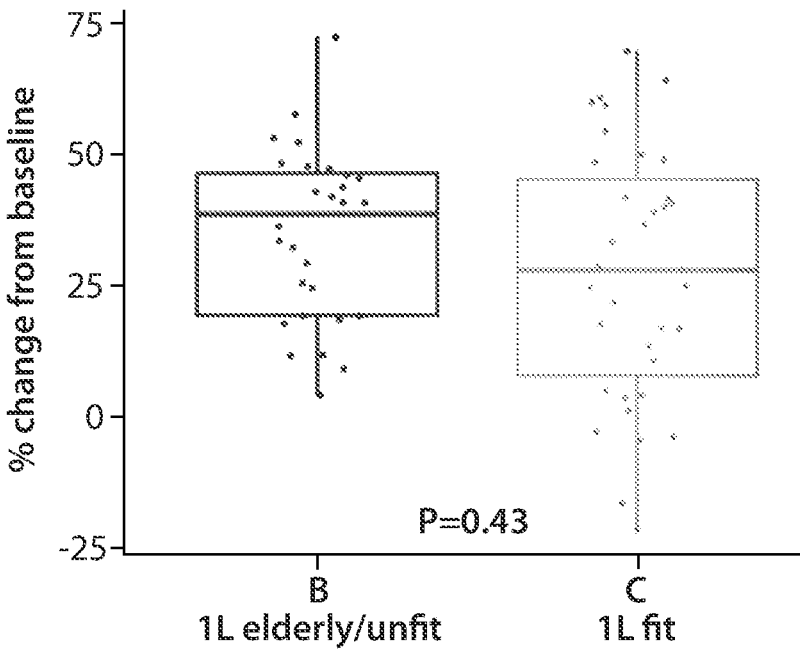
FIG. 9B

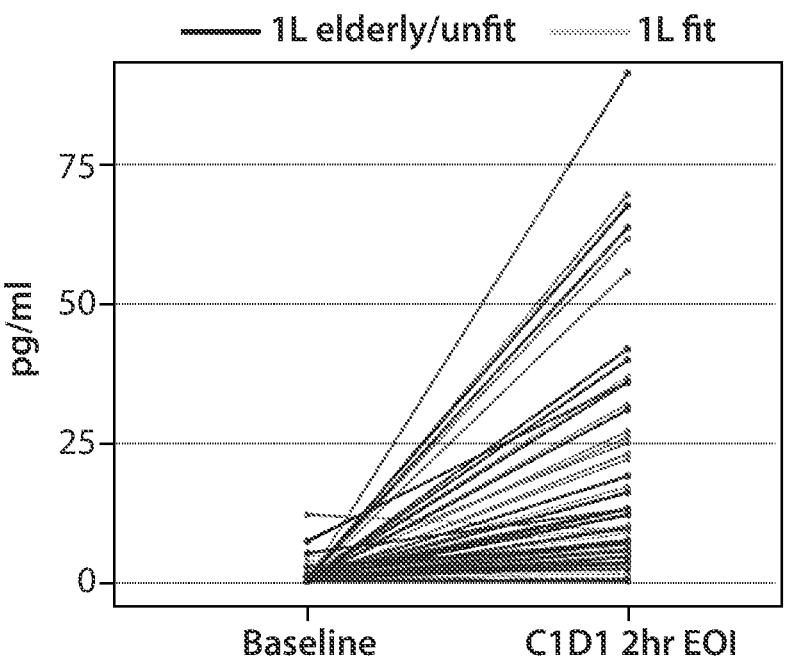
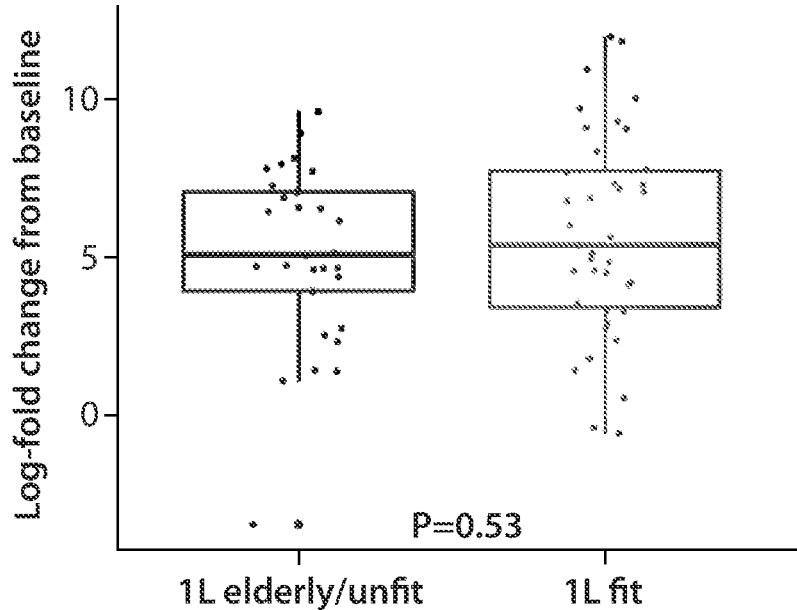
FIG. 9C

SEQUENCE LISTING

```
<160> NUMBER OF SEQ ID NOS: 36

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct

<400> SEQUENCE: 1

Gly Tyr Thr Phe Thr Ser Tyr Asn Met His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Ala Ile Tyr Pro Gly Asn Gly Asp Thr Ser Tyr Asn Gln Lys Phe Lys
1               5                   10                  15

Gly

<210> SEQ ID NO 3
<211> LENGTH: 13
<212> TYPE: PRT
<213> ORGANISM: Artificial Sequence
<220> FEATURE:
<223> OTHER INFORMATION: Synthetic Construct

<400> SEQUENCE: 3

Val Val Tyr Tyr Ser Asn Ser Tyr Trp Tyr Phe Asp Val
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct
```

-continued

<400> SEQUENCE: 4

Arg Ala Ser Ser Ser Val Ser Tyr Met His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Ala Pro Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Gln Gln Trp Ser Phe Asn Pro Pro Thr
1               5

<210> SEQ ID NO 7
<211> LENGTH: 122
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Asp Thr Ser Tyr Asn Gln Lys Phe
    50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Asn Ser Tyr Trp Tyr Phe Asp Val Trp
            100                 105                 110

Gly Gln Gly Thr Leu Val Thr Val Ser Ser
        115                 120

<210> SEQ ID NO 8
<211> LENGTH: 106
<212> TYPE: PRT
<213> ORGANISM: Artificial Sequence
<220> FEATURE:
<223> OTHER INFORMATION: Synthetic Construct

<400> SEQUENCE: 8

Asp Ile Gln Met Thr Gln Ser Pro Ser Ser Leu Ser Ala Ser Val Gly
1               5                   10                  15

-continued

```
Asp Arg Val Thr Ile Thr Cys Arg Ala Ser Ser Ser Val Ser Tyr Met
        20                      25                      30

His Trp Tyr Gln Gln Lys Pro Gly Lys Ala Pro Lys Pro Leu Ile Tyr
        35                      40                      45

Ala Pro Ser Asn Leu Ala Ser Gly Val Pro Ser Arg Phe Ser Gly Ser
    50                      55                      60

Gly Ser Gly Thr Asp Phe Thr Leu Thr Ile Ser Ser Leu Gln Pro Glu
65                      70                      75                      80

Asp Phe Ala Thr Tyr Tyr Cys Gln Gln Trp Ser Phe Asn Pro Pro Thr
                    85                      90                      95

Phe Gly Gln Gly Thr Lys Val Glu Ile Lys
                    100                     105
```

```
<210> SEQ ID NO 9
<211> LENGTH: 5
<212> TYPE: PRT
<213> ORGANISM: Artificial Sequence
<220> FEATURE:
<223> OTHER INFORMATION: Synthetic Construct

<400> SEQUENCE: 9

Asn Tyr Tyr Ile His
1               5
```

```
<210> SEQ ID NO 10
<211> LENGTH: 17
<212> TYPE: PRT
<213> ORGANISM: Artificial Sequence
<220> FEATURE:
<223> OTHER INFORMATION: Synthetic Construct

<400> SEQUENCE: 10

Trp Ile Tyr Pro Gly Asp Gly Asn Thr Lys Tyr Asn Glu Lys Phe Lys
1               5                       10                      15

Gly
```

```
<210> SEQ ID NO 11
<211> LENGTH: 10
<212> TYPE: PRT
<213> ORGANISM: Artificial Sequence
<220> FEATURE:
<223> OTHER INFORMATION: Synthetic Construct

<400> SEQUENCE: 11

Asp Ser Tyr Ser Asn Tyr Tyr Phe Asp Tyr
1               5                       10
```

```
<210> SEQ ID NO 12
<211> LENGTH: 17
<212> TYPE: PRT
<213> ORGANISM: Artificial Sequence
<220> FEATURE:
<223> OTHER INFORMATION: Synthetic Construct

<400> SEQUENCE: 12

Lys Ser Ser Gln Ser Leu Leu Asn Ser Arg Thr Arg Lys Asn Tyr Leu
1               5                       10                      15

Ala
```

```
<210> SEQ ID NO 13
<211> LENGTH: 7
<212> TYPE: PRT
<213> ORGANISM: Artificial Sequence
```

<220> FEATURE:
<223> OTHER INFORMATION: Synthetic Construct

<400> SEQUENCE: 13

Trp Ala Ser Thr Arg Glu Ser
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic Construct

<400> SEQUENCE: 14

Thr Gln Ser Phe Ile Leu Arg Thr
1               5

<210> SEQ ID NO 15
<211> LENGTH: 119
<212> TYPE: PRT
<213> ORGANISM: Artificial Sequence
<220> FEATURE:
<223> OTHER INFORMATION: Synthetic Construct

<400> SEQUENCE: 15

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Ile His Trp Val Arg Gln Ala Pro Gly Gln Gly Leu Glu Trp Ile
            35                  40                  45

Gly Trp Ile Tyr Pro Gly Asp Gly Asn Thr Lys Tyr Asn Glu Lys Phe
        50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ser Tyr Ser Asn Tyr Tyr Phe Asp Tyr Trp Gly Gln Gly
            100                 105                 110

Thr Leu Val Thr Val Ser Ser
        115

<210> SEQ ID NO 16
<211> LENGTH: 112
<212> TYPE: PRT
<213> ORGANISM: Artificial Sequence
<220> FEATURE:
<223> OTHER INFORMATION: Synthetic Construct

<400> SEQUENCE: 16

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

-continued

```
Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
        100                 105                 110

<210> SEQ ID NO 17
<211> LENGTH: 25
<212> TYPE: PRT
<213> ORGANISM: Artificial Sequence
<220> FEATURE:
<223> OTHER INFORMATION: Synthetic Construct

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 18
<211> LENGTH: 14
<212> TYPE: PRT
<213> ORGANISM: Artificial Sequence
<220> FEATURE:
<223> OTHER INFORMATION: Synthetic Construct

<400> SEQUENCE: 18

Trp Val Arg Gln Ala Pro Gly Lys Gly Leu Glu Trp Val Gly
1               5                   10

<210> SEQ ID NO 19
<211> LENGTH: 32
<212> TYPE: PRT
<213> ORGANISM: Artificial Sequence
<220> FEATURE:
<223> OTHER INFORMATION: Synthetic Construct

<400> SEQUENCE: 19

Arg Phe Thr Ile Ser Val Asp Lys Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 20
<211> LENGTH: 11
<212> TYPE: PRT
<213> ORGANISM: Artificial Sequence
<220> FEATURE:
<223> OTHER INFORMATION: Synthetic Construct

<400> SEQUENCE: 20

Trp Gly Gln Gly Thr Leu Val Thr Val Ser Ser
1               5                   10

<210> SEQ ID NO 21
<211> LENGTH: 23
<212> TYPE: PRT
<213> ORGANISM: Artificial Sequence
<220> FEATURE:
<223> OTHER INFORMATION: Synthetic Construct

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys
```

-continued

```
                20

<210> SEQ ID NO 22
<211> LENGTH: 15
<212> TYPE: PRT
<213> ORGANISM: Artificial Sequence
<220> FEATURE:
<223> OTHER INFORMATION: Synthetic Construct

<400> SEQUENCE: 22

Trp Tyr Gln Gln Lys Pro Gly Lys Ala Pro Lys Pro Leu Ile Tyr
1               5                   10                  15

<210> SEQ ID NO 23
<211> LENGTH: 32
<212> TYPE: PRT
<213> ORGANISM: Artificial Sequence
<220> FEATURE:
<223> OTHER INFORMATION: Synthetic Construct

<400> SEQUENCE: 23

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 24
<211> LENGTH: 10
<212> TYPE: PRT
<213> ORGANISM: Artificial Sequence
<220> FEATURE:
<223> OTHER INFORMATION: Synthetic Construct

<400> SEQUENCE: 24

Phe Gly Gln Gly Thr Lys Val Glu Ile Lys
1               5                   10

<210> SEQ ID NO 25
<211> LENGTH: 30
<212> TYPE: PRT
<213> ORGANISM: Artificial Sequence
<220> FEATURE:
<223> OTHER INFORMATION: Synthetic Construct

<400> SEQUENCE: 25

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 26
<211> LENGTH: 14
<212> TYPE: PRT
<213> ORGANISM: Artificial Sequence
<220> FEATURE:
<223> OTHER INFORMATION: Synthetic Construct

<400> SEQUENCE: 26

Trp Val Arg Gln Ala Pro Gly Gln Gly Leu Glu Trp Ile Gly
1               5                   10

<210> SEQ ID NO 27
<211> LENGTH: 32
<212> TYPE: PRT
<213> ORGANISM: Artificial Sequence
<220> FEATURE:
```

<223> OTHER INFORMATION: Synthetic Construct

<400> SEQUENCE: 27

Arg Ala Thr Leu Thr Ala Asp Thr Ser Thr Ser Thr Ala Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 28
<211> LENGTH: 11
<212> TYPE: PRT
<213> ORGANISM: Artificial Sequence
<220> FEATURE:
<223> OTHER INFORMATION: Synthetic Construct

<400> SEQUENCE: 28

Trp Gly Gln Gly Thr Leu Val Thr Val Ser Ser
1               5                   10

<210> SEQ ID NO 29
<211> LENGTH: 23
<212> TYPE: PRT
<213> ORGANISM: Artificial Sequence
<220> FEATURE:
<223> OTHER INFORMATION: Synthetic Construct

<400> SEQUENCE: 29

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 30
<211> LENGTH: 15
<212> TYPE: PRT
<213> ORGANISM: Artificial Sequence
<220> FEATURE:
<223> OTHER INFORMATION: Synthetic Construct

<400> SEQUENCE: 30

Trp Tyr Gln Gln Lys Pro Gly Gln Pro Pro Lys Leu Leu Ile Tyr
1               5                   10                  15

<210> SEQ ID NO 31
<211> LENGTH: 32
<212> TYPE: PRT
<213> ORGANISM: Artificial Sequence
<220> FEATURE:
<223> OTHER INFORMATION: Synthetic Construct

<400> SEQUENCE: 31

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 32
<211> LENGTH: 10
<212> TYPE: PRT
<213> ORGANISM: Artificial Sequence
<220> FEATURE:
<223> OTHER INFORMATION: Synthetic Construct

<400> SEQUENCE: 32

Phe Gly Gln Gly Thr Lys Val Glu Ile Lys

```
1               5                    10
```

<210> SEQ ID NO 33
<211> LENGTH: 452
<212> TYPE: PRT
<213> ORGANISM: Artificial Sequence
<220> FEATURE:
<223> OTHER INFORMATION: Synthetic Construct

<400> SEQUENCE: 33

```
Glu Val Gln Leu Val Glu Ser Gly Gly Gly Leu Val Gln Pro Gly Gly
1               5                    10                   15

Ser Leu Arg Leu Ser Cys Ala Ala Ser Gly Tyr Thr Phe Thr Ser Tyr
            20                   25                   30

Asn Met His Trp Val Arg Gln Ala Pro Gly Lys Gly Leu Glu Trp Val
        35                   40                   45

Gly Ala Ile Tyr Pro Gly Asn Gly Asp Thr Ser Tyr Asn Gln Lys Phe
    50                   55                   60

Lys Gly Arg Phe Thr Ile Ser Val Asp Lys Ser Lys Asn Thr Leu Tyr
65                   70                   75                   80

Leu Gln Met Asn Ser Leu Arg Ala Glu Asp Thr Ala Val Tyr Tyr Cys
                85                   90                   95

Ala Arg Val Val Tyr Tyr Ser Asn Ser Tyr Trp Tyr Phe Asp Val Trp
            100                  105                  110

Gly Gln Gly Thr Leu Val Thr Val Ser Ser Ala Ser Thr Lys Gly Pro
            115                  120                  125

Ser Val Phe Pro Leu Ala Pro Ser Ser Lys Ser Thr Ser Gly Gly Thr
    130                  135                  140

Ala Ala Leu Gly Cys Leu Val Lys Asp Tyr Phe Pro Glu Pro Val Thr
145                  150                  155                  160

Val Ser Trp Asn Ser Gly Ala Leu Thr Ser Gly Val His Thr Phe Pro
                165                  170                  175

Ala Val Leu Gln Ser Ser Gly Leu Tyr Ser Leu Ser Ser Val Val Thr
            180                  185                  190

Val Pro Ser Ser Ser Leu Gly Thr Gln Thr Tyr Ile Cys Asn Val Asn
            195                  200                  205

His Lys Pro Ser Asn Thr Lys Val Asp Lys Lys Val Glu Pro Lys Ser
    210                  215                  220

Cys Asp Lys Thr His Thr Cys Pro Pro Cys Pro Ala Pro Glu Leu Leu
225                  230                  235                  240

Gly Gly Pro Ser Val Phe Leu Phe Pro Pro Lys Pro Lys Asp Thr Leu
            245                  250                  255

Met Ile Ser Arg Thr Pro Glu Val Thr Cys Val Val Val Asp Val Ser
            260                  265                  270

His Glu Asp Pro Glu Val Lys Phe Asn Trp Tyr Val Asp Gly Val Glu
    275                  280                  285

Val His Asn Ala Lys Thr Lys Pro Arg Glu Glu Gln Tyr Gly Ser Thr
    290                  295                  300

Tyr Arg Val Val Ser Val Leu Thr Val Leu His Gln Asp Trp Leu Asn
305                  310                  315                  320

Gly Lys Glu Tyr Lys Cys Lys Val Ser Asn Lys Ala Leu Pro Ala Pro
            325                  330                  335

Ile Glu Lys Thr Ile Ser Lys Ala Lys Gly Gln Pro Arg Glu Pro Gln
            340                  345                  350

Val Tyr Thr Leu Pro Pro Ser Arg Glu Glu Met Thr Lys Asn Gln Val
```

-continued

```
              355                  360                  365

Ser Leu Trp Cys Leu Val Lys Gly Phe Tyr Pro Ser Asp Ile Ala Val
    370                  375                  380

Glu Trp Glu Ser Asn Gly Gln Pro Glu Asn Asn Tyr Lys Thr Thr Pro
385                  390                  395                  400

Pro Val Leu Asp Ser Asp Gly Ser Phe Phe Leu Tyr Ser Lys Leu Thr
                405                  410                  415

Val Asp Lys Ser Arg Trp Gln Gln Gly Asn Val Phe Ser Cys Ser Val
                420                  425                  430

Met His Glu Ala Leu His Asn His Tyr Thr Gln Lys Ser Leu Ser Leu
                435                  440                  445

Ser Pro Gly Lys
    450
```

<210> SEQ ID NO 34
<211> LENGTH: 213
<212> TYPE: PRT
<213> ORGANISM: Artificial Sequence
<220> FEATURE:
<223> OTHER INFORMATION: Synthetic Construct

<400> SEQUENCE: 34

```
Asp Ile Gln Met Thr Gln Ser Pro Ser Ser Leu Ser Ala Ser Val Gly
1               5                  10                  15

Asp Arg Val Thr Ile Thr Cys Arg Ala Ser Ser Ser Val Ser Tyr Met
                20                  25                  30

His Trp Tyr Gln Gln Lys Pro Gly Lys Ala Pro Lys Pro Leu Ile Tyr
                35                  40                  45

Ala Pro Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Phe Asn Pro Pro Thr
                85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
                115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
    210
```

<210> SEQ ID NO 35
<211> LENGTH: 449
<212> TYPE: PRT
<213> ORGANISM: Artificial Sequence
<220> FEATURE:
<223> OTHER INFORMATION: Synthetic Construct

<400> SEQUENCE: 35

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Ile His Trp Val Arg Gln Ala Pro Gly Gln Gly Leu Glu Trp Ile
        35                  40                  45

Gly Trp Ile Tyr Pro Gly Asp Gly Asn Thr Lys Tyr Asn Glu Lys Phe
    50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ser Tyr Ser Asn Tyr Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys

-continued

```
             405              410              415

Ser Arg Trp Gln Gln Gly Asn Val Phe Ser Cys Ser Val Met His Glu
            420              425              430

Ala Leu His Asn His Tyr Thr Gln Lys Ser Leu Ser Leu Ser Pro Gly
        435              440              445

Lys

<210> SEQ ID NO 36
<211> LENGTH: 219
<212> TYPE: PRT
<213> ORGANISM: Artificial Sequence
<220> FEATURE:
<223> OTHER INFORMATION: Synthetic Construct

<400> SEQUENCE: 36

Asp Ile Val Met Thr Gln Ser Pro Asp Ser Leu Ala Val Ser Leu Gly
1               5                10               15

Glu Arg Ala Thr Ile Asn Cys Lys Ser Ser Gln Ser Leu Leu Asn Ser
            20               25               30

Arg Thr Arg Lys Asn Tyr Leu Ala Trp Tyr Gln Gln Lys Pro Gly Gln
        35               40               45

Pro Pro Lys Leu Leu Ile Tyr Trp Ala Ser Thr Arg Glu Ser Gly Val
    50               55               60

Pro Asp Arg Phe Ser Gly Ser Gly Ser Gly Thr Asp Phe Thr Leu Thr
65               70               75               80

Ile Ser Ser Leu Gln Ala Glu Asp Val Ala Val Tyr Tyr Cys Thr Gln
            85               90               95

Ser Phe Ile Leu Arg Thr Phe Gly Gln Gly Thr Lys Val Glu Ile Lys
        100              105              110

Arg Thr Val Ala Ala Pro Ser Val Phe Ile Phe Pro Pro Ser Asp Glu
        115              120              125

Gln Leu Lys Ser Gly Thr Ala Ser Val Val Cys Leu Leu Asn Asn Phe
    130              135              140

Tyr Pro Arg Glu Ala Lys Val Gln Trp Lys Val Asp Asn Ala Leu Gln
145              150              155              160

Ser Gly Asn Ser Gln Glu Ser Val Thr Glu Gln Asp Ser Lys Asp Ser
            165              170              175

Thr Tyr Ser Leu Ser Ser Thr Leu Thr Leu Ser Lys Ala Asp Tyr Glu
        180              185              190

Lys His Lys Val Tyr Ala Cys Glu Val Thr His Gln Gly Leu Ser Ser
        195              200              205

Pro Val Thr Lys Ser Phe Asn Arg Gly Glu Cys
    210              215
```

METHODS FOR TREATMENT OF B CELL PROLIFERATIVE DISORDERS WITH ANTI-CD20/ANTI-CD3 BISPECIFIC ANTIBODIES

CROSS-REFERENCE TO RELATED APPLICATIONS

This application claims benefit of priority to U.S. Provisional Application No. 63/195,677, filed on Jun. 1, 2021, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on May 27, 2022, is named 50474-258002_Sequence_Listing_05_27_22_ST25 and is 23,644 bytes in size.

FIELD OF THE INVENTION

The present invention relates to the treatment of CD20-positive cell proliferative disorders in elderly and unfit subjects. More specifically, the invention pertains to treatment of elderly and/or unfit subjects having a B cell proliferative disorder by administration of a bispecific antibody that binds to anti-cluster of differentiation 20 (CD20) and anti-cluster of differentiation 3 (CD3).

BACKGROUND

Cancers are characterized by the uncontrolled growth of cell subpopulations. Cancers are the leading cause of death in the developed world and the second leading cause of death in developing countries, with over 14 million new cancer cases diagnosed and over eight million cancer deaths occurring each year. Cancer care thus represents a significant and ever-increasing societal burden.

B cell proliferative disorders are a leading cause of cancer-related deaths. For example, non-Hodgkin's lymphoma (NHL) advances quickly and is fatal if untreated. In the United States, B-cell lymphomas constitute approximately 80%-85% of all cases of NHL. Diffuse large B-cell lymphoma (DLBCL) is the most common type of NHL accounting for approximately 30%-40% of all NHL diagnosis, followed by follicular lymphoma (FL; 20%-25% of all NHL diagnosis) and mantle cell lymphoma (MCL; 6%-10% of all NHL diagnosis). B-cell chronic lymphocytic leukemia (CLL) is the most common leukemia in adults, with approximately 15,000 new cases per year in the United States (American Cancer Society 2015).

Treatment of B cell proliferative disorders, such as DLBCL and high grade B-cell lymphoma (HGBL), in older patients presents particular challenges, in part because of the presence of preexisting comorbidities, functional impairments, and cognitive decline (Pal et al. 2010) associated with increasing age. Elderly patients benefit substantially from standard immunochemotherapy induction when they can tolerate it (Pfreundschuh et al. 2008); however, there remains a substantial number of patients who are unable to tolerate full-dose standard immunochemotherapy (Hamlin et al. 2014). Studies report around 13%-30% of newly diagnosed patients with DLBCL are unfit to receive full-dose chemotherapy for reasons such as age, poor performance, or decreased end-organ function (Janssen-Heijnen et al. 2005; Hamlin et al. 2014; Chiappella et al. 2017).

Bispecific antibodies are capable of simultaneously binding cell surface antigens on cytotoxic cells (e.g., T cells, via binding to cluster of differentiation 3 (CD3)) and cancer cells (e.g., B cells, via binding to CD20), with the intent that the bound cytotoxic cell will destroy the bound cancer cell. However, such antibody-based immunotherapies may be limited by unwanted effects, including cytokine-driven toxicities (e.g., cytokine release syndrome (CRS)), infusion-related reactions (IRRs), severe tumor lysis syndrome (TLS), and central nervous system (CNS) toxicities. Thus, there is an unmet need in the field for the development of efficacious methods of dosing therapeutic bispecific antibodies (e.g., bispecific antibodies that bind to CD20 and CD3) for the treatment of B cell proliferative disorders (e.g., DLBCL or high grade B-cell lymphoma (HGBL)) that achieve a more favorable benefit-risk profile in elderly patients who may be unfit for treatment with full-dose and/or standard chemotherapy.

SUMMARY OF THE INVENTION

The present invention relates to methods of treating a subject having a previously untreated B cell proliferative disorder (e.g., a previously untreated high grade B-cell lymphoma or a previously untreated diffuse large B-cell lymphoma (DLBCL)) by intravenous administration of mosunetuzumab as a monotherapy.

In one aspect, the invention features a method of treating a subject having a previously untreated B cell proliferative disorder comprising intravenously administering to the subject, as a monotherapy, mosunetuzumab in a dosing regimen comprising at least a first dosing cycle and a second dosing cycle, wherein: the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and the second dosing cycle comprises a single dose (C2D1) of the mosunetuzumab, wherein the C2D1 is equivalent in amount to the C1D3.

In one aspect, the invention features a method of treating an elderly subject having a previously untreated B cell proliferative disorder comprising intravenously administering to the subject, as a monotherapy, mosunetuzumab in a dosing regimen comprising at least a first dosing cycle and a second dosing cycle, wherein: (a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and (b) the second dosing cycle comprises a single dose (C2D1) of the mosunetuzumab, wherein the C2D1 is equivalent in amount to the C1D3. In some embodiments, the elderly subject is at least 60-years old. In some embodiments, the elderly subject is at least 65-years old. In some embodiments, the elderly subject is at least 80-years old.

In one aspect, the invention features a method of treating an unfit subject having a previously untreated B cell proliferative disorder comprising intravenously administering to the subject, as a monotherapy, mosunetuzumab in a dosing regimen comprising at least a first dosing cycle and a second dosing cycle, wherein: (a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and (b) the second dosing cycle comprises a single dose (C2D1) of the mosunetuzumab, wherein the C2D1 is equivalent in amount to the C1D3. In some embodiments, the unfit subject is at least 60-years old. In some embodiments, the unfit subject is 60-years to 79-years old. In some embodiments, the unfit subject exhibits: (i) an impairment in at least one activity of daily living (ADL) component; (ii) an impairment in at least one instrumental activity of daily living (IADL) component; (iii) an impairment in at least one of cardiac function, vascular function, renal function, and/or liver function; and/or (iv) diabetes. In some embodiments, the unfit subject exhibits an impairment in at least one ADL component. In some embodiments, the unfit subject exhibits an impairment in at least one IADL component. In some embodiments, the unfit subject exhibits an impairment in cardiac function comprising heart arrhythmia, congestive heart failure (CHF), myocardial infarction, and/or cardiac-related symptoms of hypothyroidism. In some embodiments, the unfit subject exhibits an impairment in vascular function comprising anemia, cerebrovascular accident (CVA), cerebrovascular disease (CVD), chronic obstructive pulmonary disease not otherwise specified (COPD: NOS), hyperlipidemia, peripheral vascular disease, stroke, and/or ischemic attack (TIA). In some embodiments, the unfit subject exhibits an impairment in renal function comprising acute kidney disease and/or chronic kidney disease. In some embodiments, the unfit subject exhibits an impairment in liver function. In some embodiments, the unfit subject exhibits diabetes, comprising type 2 diabetes, diabetes with end organ damage (EOD), and/or diabetes without EOD. In some embodiments, the subject is unsuitable for treatment with R-CHOP therapy.

In one aspect, the invention features a method of treating a subject having a previously untreated B cell proliferative disorder comprising intravenously administering to the subject, as a monotherapy, mosunetuzumab in a dosing regimen comprising at least a first dosing cycle and a second dosing cycle, wherein: (a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and (b) the second dosing cycle comprises a single dose (C2D1) of the mosunetuzumab, wherein the C2D1 is equivalent in amount to the C1D3, wherein the subject is unsuitable for treatment with R-CHOP therapy.

In some embodiments, the R-CHOP therapy comprises rituximab, cyclophosphamide, doxorubicin, vincristine, and prednisone, and further wherein the rituximab is administered to the subject at a dose of 375 mg/m2 every three weeks.

In some embodiments, the C1D3 and the C2D1 are each 13.5 mg. In some embodiments, the C1D3 and the C2D1 are each 30 mg. In some embodiments, the first and second dosing cycles are 21-day (e.g., 21±3 days) dosing cycles. In some embodiments, the method comprises administering the C1D1, the C1D2, and the C1D3 on Days 1, 8 (±1 day), and 15 (±1 day), respectively, of the first dosing cycle. In some embodiments, the method comprises administering the C2D1 on Day 1 (±1 day) of the second dosing cycle.

In some embodiments, the dosing regimen further comprises one or more additional dosing cycles. In some embodiments, the dosing regimen comprises six to 15 additional dosing cycles. In some embodiments, the dosing regimen comprises six additional dosing cycles. In some embodiments, the dosing regimen comprises 15 additional dosing cycles. In some embodiments, the additional dosing cycles are 21-day (e.g., 21±3 days) dosing cycles. In some embodiments, one or more of the additional dosing cycles comprise an additional single dose of the mosunetuzumab. In some embodiments, the additional single dose of the mosunetuzumab is administered to the subject on Day 1 (±1 day) of each additional dosing cycle. In some embodiments, the additional single dose of the mosunetuzumab is equivalent in amount to the C1D3. In some embodiments, the additional single dose of the mosunetuzumab is 13.5 mg. In some embodiments, the additional single dose of the mosunetuzumab is 30 mg.

In some embodiments, the method further comprises administering to the subject one or more additional therapeutic agents. In some embodiments, the one or more additional therapeutic agents is tocilizumab. In some embodiments, the one or more additional therapeutic agents is an antihistamine. In some embodiments, the antihistamine is diphenhydramine. In some embodiments, the one or more additional therapeutic agents comprises allopurinol and rasburicase.

In some embodiments, the one or more additional therapeutic agents is a corticosteroid. In some embodiments, the corticosteroid comprises prednisone, prednisolone, methylprednisolone, or dexamethasone. In some embodiments, the corticosteroid comprises prednisone. In some embodiments, the prednisone is administered to the subject on each of the seven days (±1 day) prior to the administration of the C1D1. In some embodiments, the prednisone is administered at a dose of 100 mg/day.

In some embodiments, the one or more additional therapeutic agents comprises a single dose of vincristine, and wherein the single dose of vincristine is 1 mg. In some embodiments, the single dose of vincristine is administered to the subject seven days (±1 day) prior to the administration of the C1D1.

In some embodiments, the previously untreated B cell proliferative disorder is a previously untreated high-grade B-cell lymphoma. In some embodiments, the previously untreated B cell proliferative disorder is a previously untreated non-Hodgkin's lymphoma (NHL). In some embodiments, the previously untreated NHL is a previously untreated DLBCL.

In one aspect, the invention features a method of treating a population of subjects having a previously untreated DLBCL comprising intravenously administering to the subjects, as a monotherapy, mosunetuzumab in a dosing regimen comprising eight 21-day (e.g., 21±3 days) dosing cycles, wherein: (a) the first dosing cycle comprises a first dose (C1D1), a second dose (C1D2), and a third dose (C1D3) of the mosunetuzumab administered on Days 1, 8 (±1 day), and 15 (±1 day), respectively, of the first dosing cycle, wherein the C1D1 is 1 mg, the C1D2 is 2 mg, and the C1D3 is 13.5 or 30 mg; and (b) the second to eighth dosing cycles each comprises a single dose (C2D1-C8D1) of the mosunetuzumab administered on Day 1 (±1 day) of each dosing cycle, wherein each single dose C2D1-C8D1 is equivalent in amount to the C1D3, wherein the subjects are at least 65-years old, and wherein the subjects are unfit for treatment with standard R-CHOP therapy.

In one aspect, the invention features a method of treating a population of subjects having a previously untreated DLBCL comprising intravenously administering to the subjects, as a monotherapy, mosunetuzumab in a dosing regimen comprising seventeen 21-day (e.g., 21±3 days) dosing cycles, wherein: (a) the first dosing cycle comprises a first dose (C1D1), a second dose (C1D2), and a third dose (C1D3) of the mosunetuzumab administered on Days 1, 8 (±1 day), and 15 (±1 day), respectively, of the first dosing cycle, wherein the C1D1 is 1 mg, the C1D2 is 2 mg, and the C1D3 is 13.5 or 30 mg; and (b) the second to seventeenth dosing cycles each comprises a single dose (C2D1-C17D1) of the mosunetuzumab administered on Day 1 (±1 day) of each dosing cycle, wherein each single dose C2D1-C17D1 is equivalent in amount to the C1D3, wherein the subjects are at least 65-years old, and wherein the subjects are unfit for treatment with standard R-CHOP therapy.

In some embodiments, the overall response rate is greater than 56% (e.g., greater than 57%, 58%, 59%, 60%, 61%, 62%, 63%, 64%, 65%, 66%, 67%, 68%, 69%, 70%, 71%, 72%, 73%, 74%, 75%, 76%, 77%, 78%, 80%, 85%, 90%, 95%, 97%, 98%, 99%, or 100%; e.g., between 56%-100%, 56%-90%, 56%-80%, 56%-70%, 56%-68%, 56%-67%, 56%-66%, 56%-65%, 56%-64%, 56%-63%, 56%-62%, 56%-61%, 56%-60%, 56%-59%, 56%-58%, 56%-57%, 57%-61%, 58%-61%, 59%-61%, 60%-61%, 57%-60%, 58%-59%, 57%-59%, 61%-65%, 61%-70%, 61%-75%, 61%-80%, 61%-90%, 70%-90%, 65%-80%, 60%-90%, 75%-85%, 85%-100%, 56%-66%, 56%-71%, 59%-63%, or 60%-65%; e.g., 56%, 57%, 58%, 59%, 60%, 61%, 62%, 63%, 64%, 65%, 66%, 67%, 68%, 69%, 70%, 75%, 80%, 85%, 90%, 95%, 97%, 98%, 99%, or 100%). In some embodiments, the overall response rate is greater than 61%.

In some embodiments, the complete response rate is greater than 38% (e.g., greater than 39%, 40%, 41%, 42%, 43%, 44%, 45%, 46%, 47%, 48%, 49%, 50%, 51%, 52%, 53%, 54%, 55%, 56%, 57%, 58%, 59%, 60%, 65%, 70%, 75%, 80%, 85%, 90%, 95%, 97%, 98%, 99%, or 100%; e.g., between 38%-100%, 38%-90%, 38%-80%, 38%-70%, 38%-65%, 38%-60%, 38%-55%, 38%-50%, 38%-48%, 38%-47%, 38%-46%, 38%-45%, 38%-44%, 38%-43%, 38%-42%, 38%-41%, 38%-40%, 38%-39%, 39%-43%, 40%-43%, 41%-43%, 42%-43%, 39%-42%, 43%-45%, 43%-48%, 43%-50%, 43%-55%, 43%-60%, 43%-70%, 43%-80%, 43%-90%, 43%-100%, 50%-90%, 60%-80%, 55%-70%, 85%-100%, 39%-50%, 41%-50%, 39%-55%, or 41%-55%; e.g., 38%, 39%, 40%, 41%, 42%, 43%, 44%, 45%, 46%, 47%, 48%, 49%, 50%, 52%, 54%, 55%, 57%, 60%, 65%, 70%, 75%, 80%, 85%, 90%, 95%, 97%, 98%, 99%, or 100%). In some embodiments, the complete response rate is greater than 43%.

In some embodiments, greater than 42% (e.g., greater than 43%, 44%, 45%, 46%, 47%, 48%, 49%, 50%, 51%, 52%, 53%, 54%, 55%, 56%, 57%, 58%, 59%, 60%, 65%, 70%, 75%, 80%, 85%, 90%, 95%, 97%, 98%, 99%, or 100%; e.g., between 42%-100%, 45%-100%, 50%-100%, 55%-100%, 60%-100%, 65%-100%, 70%-100%, 80%-100%, 90%-100%, 42%-47%, 42%-50%, 42%-55%, 42%-60%, 42%-65%, 42%-70%, 42%-80%, 42%-90%, 47%-55%, 47%-60%, 47%-70%, 45%-55%, or 45%-60%; e.g., 43%, 44%, 45%, 46%, 47%, 48%, 49%, 50%, 51%, 52%, 53%, 54%, 55%, 56%, 57%, 58%, 59%, 60%, 65%, 70%, 75%, 80%, 85%, 90%, 95%, 97%, 98%, 99%, or 100%) of subjects having a complete response maintained complete remission for 12 months. In some embodiments, greater than 47% of subjects having a complete response maintained complete remission for 12 months.

In some embodiments, the rate of cytokine release syndrome having a grade of 3 or higher (as defined by the American Society for Transplantation and Cellular Therapy®, 2018; ASTCT®) is less than 5% (e.g., less than 4%, less than 3%, less than 2%, or less than 1%; e.g., 4%, 3%, 2%, 1%, or 0%). In some embodiments, the rate of cytokine release syndrome having a grade of 3 or higher (as defined by the ASTCT®) is less than 3%. In some embodiments, the rate of cytokine release syndrome having a grade of 3 or higher (as defined by the ASTCT®) is less than 1%.

In some embodiments, the rate of cytokine release syndrome having a grade of 3 or higher (as defined by the ASTCT®) is 0%.

In one aspect, the invention features a method of treating a subject having a previously untreated B cell proliferative disorder comprising intravenously administering to the subject, as a monotherapy, mosunetuzumab in a dosing regimen comprising eight 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8, and 15, respectively, of the first dosing cycle, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab administered on Day 1 (±1 day) of each dosing cycle, wherein each single dose C2D1-C8D1 is equivalent in amount to the C1D3.

In one aspect, the invention features a method of treating a subject having a previously untreated B cell proliferative disorder comprising intravenously administering to the subject, as a monotherapy, mosunetuzumab in a dosing regimen comprising eight 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 30 mg; and (b) the second to eighth dosing cycles each comprises a single dose (C2D1-C8D1) of mosunetuzumab administered on Day 1 (±1 day) of each dosing cycle, wherein each single dose C2D1-C8D1 is equivalent in amount to the C1D3.

In one aspect, the invention features a method of treating a subject having a previously untreated B cell proliferative disorder comprising intravenously administering to the subject, as a monotherapy, mosunetuzumab in a dosing regimen comprising seventeen 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 13.5 mg; and (b) the second to seventeenth dosing cycles each comprises a single dose (C2D1-C17D1) of mosunetuzumab administered on Day 1 (±1 day) of each dosing cycle, wherein each single dose C2D1-C17D1 is equivalent in amount to the C1D3.

In one aspect, the invention features a method of treating a subject having a previously untreated B cell proliferative disorder comprising intravenously administering to the subject, as a monotherapy, mosunetuzumab in a dosing regimen comprising seventeen 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab administered on Day 1 (±1 day) of each dosing cycle, wherein each single dose C2D1-C17D1 is equivalent in amount to the C1D3.

In one aspect, the invention features a method of treating a subject having a previously untreated DLBCL comprising intravenously administering to the subject, as a monotherapy, mosunetuzumab in a dosing regimen comprising eight 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab administered on Day 1 (±1 day) of each dosing cycle, wherein each single dose C2D1-C8D1 is equivalent in amount to the C1D3.

In one aspect, the invention features a method of treating a subject having a previously untreated DLBCL comprising intravenously administering to the subject, as a mono-therapy, mosunetuzumab in a dosing regimen comprising eight 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 30 mg; and (b) the second to eighth dosing cycles each comprises a single dose (C2D1-C8D1) of mosunetuzumab administered on Day 1 (±1 day) of each dosing cycle, wherein each single dose C2D1-C8D1 is equivalent in amount to the C1D3.

In one aspect, the invention features a method of treating a subject having a previously untreated DLBCL comprising intravenously administering to the subject, as a mono-therapy, mosunetuzumab in a dosing regimen comprising seventeen 21-day (e.g., 21±3 days) dosing cycles, wherein: (a) the first dosing cycle comprises a first dose (C1D1), a second dose (C1D2), and a third dose (C1D3) of mosu-netuzumab administered on Days 1, 8 (±1 day), and 15 (±1 day), respectively, of the first dosing cycle, wherein the C1D1 is 1 mg, the C1D2 is 2 mg, and the C1D3 is 13.5 mg; and (b) the second to seventeenth dosing cycles each com-prises a single dose (C2D1-C17D1) of mosunetuzumab administered on Day 1 (±1 day) of each dosing cycle, wherein each single dose C2D1-C17D1 is equivalent in amount to the C1D3.

In one aspect, the invention features a method of treating a subject having a previously untreated DLBCL comprising intravenously administering to the subject, as a mono-therapy, mosunetuzumab in a dosing regimen comprising seventeen 21-day (e.g., 21±3 days) dosing cycles, wherein: (a) the first dosing cycle comprises a first dose (C1D1), a second dose (C1D2), and a third dose (C1D3) of mosu-netuzumab administered on Days 1, 8 (±1 day), and 15 (±1 day), respectively, of the first dosing cycle, wherein the C1D1 is 1 mg, the C1D2 is 2 mg, and the C1D3 is 30 mg; and (b) the second to seventeenth dosing cycles each com-prises a single dose (C2D1-C17D1) of mosunetuzumab administered on Day 1 (±1 day) of each dosing cycle, wherein each single dose C2D1-C17D1 is equivalent in amount to the C1D3.

In one aspect, the invention features a method of treating a subject having a previously untreated DLBCL comprising intravenously administering to the subject, as a mono-therapy, mosunetuzumab in a dosing regimen comprising eight 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab administered on Day 1 (±1 day) of each dosing cycle, wherein each single dose C2D1-C8D1 is equivalent in amount to the C1D3, wherein the subject is at least 65-years old, and wherein the subject is unfit for treatment with standard R-CHOP therapy.

In one aspect, the invention features a method of treating a subject having a previously untreated DLBCL comprising intravenously administering to the subject, as a mono-therapy, mosunetuzumab in a dosing regimen comprising eight 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 30 mg; and (b) the second to eighth dosing cycles each comprises a single dose (C2D1-C8D1) of mosunetuzumab administered on Day 1 (±1 day) of each dosing cycle, wherein each single dose C2D1-C8D1 is equivalent in amount to the C1D3, wherein the subject is at least 65-years old, and wherein the subject is unfit for treatment with standard R-CHOP therapy.

In one aspect, the invention features a method of treating a subject having a previously untreated DLBCL comprising intravenously administering to the subject, as a mono-therapy, mosunetuzumab in a dosing regimen comprising seventeen 21-day (e.g., 21±3 days) dosing cycles, wherein: (a) the first dosing cycle comprises a first dose (C1D1), a second dose (C1D2), and a third dose (C1D3) of mosu-netuzumab administered on Days 1, 8 (±1 day), and 15 (±1 day), respectively, of the first dosing cycle, wherein the C1D1 is 1 mg, the C1D2 is 2 mg, and the C1D3 is 13.5 mg; and (b) the second to seventeenth dosing cycles each com-prises a single dose (C2D1-C17D1) of mosunetuzumab administered on Day 1 (±1 day) of each dosing cycle, wherein each single dose C2D1-C17D1 is equivalent in amount to the C1D3, wherein the subject is at least 65-years old, and wherein the subject is unfit for treatment with standard R-CHOP therapy.

In one aspect, the invention features a method of treating a subject having a previously untreated DLBCL comprising intravenously administering to the subject, as a mono-therapy, mosunetuzumab in a dosing regimen comprising seventeen 21-day (e.g., 21±3 days) dosing cycles, wherein: (a) the first dosing cycle comprises a first dose (C1D1), a second dose (C1D2), and a third dose (C1D3) of mosu-netuzumab administered on Days 1, 8 (±1 day), and 15 (±1 day), respectively, of the first dosing cycle, wherein the C1D1 is 1 mg, the C1D2 is 2 mg, and the C1D3 is 30 mg; and (b) the second to seventeenth dosing cycles each com-prises a single dose (C2D1-C17D1) of mosunetuzumab administered on Day 1 (±1 day) of each dosing cycle, wherein each single dose C2D1-C17D1 is equivalent in amount to the C1D3, wherein the subject is at least 65-years old, and wherein the subject is unfit for treatment with standard R-CHOP therapy.

In one aspect, the invention features a method of treating an elderly subject having a previously untreated DLBCL comprising intravenously administering to the subject, as a monotherapy, mosunetuzumab in a dosing regimen compris-ing eight 21-day (e.g., 21±3 days) dosing cycles, wherein: (a) the first dosing cycle comprises a first dose (C1D1), a second dose (C1D2), and a third dose (C1D3) of mosu-netuzumab administered on Days 1, 8 (±1 day), and 15 (±1 day), respectively, of the first dosing cycle, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab administered on Day 1 (±1 day) of each dosing cycle, wherein each single dose C2D1-C8D1 is equivalent in amount to the C1D3, wherein the subject is at least 80-years old.

9

10

In one aspect, the invention features a method of treating an elderly subject having a previously untreated DLBCL comprising intravenously administering to the subject, as a monotherapy, mosunetuzumab in a dosing regimen comprising eight 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 30 mg; and (b) the second to eighth dosing cycles each comprises a single dose (C2D1-C8D1) of mosunetuzumab administered on Day 1 (±1 day) of each dosing cycle, wherein each single dose C2D1-C8D1 is equivalent in amount to the C1D3, wherein the subject is at least 80-years old.

In one aspect, the invention features a method of treating an elderly subject having a previously untreated DLBCL comprising intravenously administering to the subject, as a monotherapy, mosunetuzumab in a dosing regimen comprising seventeen 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 13.5 mg; and (b) the second to seventeenth dosing cycles each comprises a single dose (C2D1-C17D1) of mosunetuzumab administered on Day 1 (±1 day) of each dosing cycle, wherein each single dose C2D1-C17D1 is equivalent in amount to the C1D3, wherein the subject is at least 80-years old.

In one aspect, the invention features a method of treating an elderly subject having a previously untreated DLBCL comprising intravenously administering to the subject, as a monotherapy, mosunetuzumab in a dosing regimen comprising seventeen 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab administered on Day 1 (±1 day) of each dosing cycle, wherein each single dose C2D1-C17D1 is equivalent in amount to the C1D3, wherein the subject is at least 80-years old.

In one aspect, the invention features a method of treating an unfit subject having a previously untreated DLBCL comprising intravenously administering to the subject, as a monotherapy, mosunetuzumab in a dosing regimen comprising eight 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab administered on Day 1 (±1 day) of each dosing cycle, wherein each single dose C2D1-C8D1 is equivalent in amount to the C1D3, wherein the subject is at least 60-years old, and wherein the subject exhibits: (i) an impairment in at least ADL component (Katz et al., 1970); (ii) an impairment in at least one IADL component (Lawton and Brody, 1969); (iii) an impairment in at least one of cardiac function, vascular function, renal function, and/or liver function; and/or (iv) diabetes.

In one aspect, the invention features a method of treating an unfit subject having a previously untreated DLBCL comprising intravenously administering to the subject, as a monotherapy, mosunetuzumab in a dosing regimen comprising eight 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 30 mg; and (b) the second to eighth dosing cycles each comprises a single dose (C2D1-C8D1) of mosunetuzumab administered on Day 1 (±1 day) of each dosing cycle, wherein each single dose C2D1-C8D1 is equivalent in amount to the C1D3, wherein the subject is at least 60-years old, and wherein the subject exhibits: (i) an impairment in at least ADL component; (ii) an impairment in at least one IADL component; (iii) an impairment in at least one of cardiac function, vascular function, renal function, and/or liver function; and/or (iv) diabetes.

In one aspect, the invention features a method of treating an unfit subject having a previously untreated DLBCL comprising intravenously administering to the subject, as a monotherapy, mosunetuzumab in a dosing regimen comprising seventeen 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 13.5 mg; and (b) the second to seventeenth dosing cycles each comprises a single dose (C2D1-C17D1) of mosunetuzumab administered on Day 1 (±1 day) of each dosing cycle, wherein each single dose C2D1-C17D1 is equivalent in amount to the C1D3, wherein the subject is at least 60-years old, and wherein the subject exhibits: (i) an impairment in at least ADL component; (ii) an impairment in at least one IADL component; (iii) an impairment in at least one of cardiac function, vascular function, renal function, and/or liver function; and/or (iv) diabetes.

In one aspect, the invention features a method of treating an unfit subject having a previously untreated DLBCL comprising intravenously administering to the subject, as a monotherapy, mosunetuzumab in a dosing regimen comprising seventeen 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab administered on Day 1 (±1 day) of each dosing cycle, wherein each single dose C2D1-C17D1 is equivalent in amount to the C1D3, wherein the subject is at least 60-years old, and wherein the subject exhibits: (i) an impairment in at least ADL component; (ii) an impairment in at least one IADL component; (iii) an impairment in at least one of cardiac function, vascular function, renal function, and/or liver function; and/or (iv) diabetes.

In some embodiments, the subject is human. In some embodiments, the subjects comprising the population of subjects are human.

IRA=interim response assessment; SD=stable disease; PR=partial response; PRA=primary response assessment.

FIG. 2 is a table showing patient disposition and baseline characteristics of the patients of the study described in Example 2. R-CHOP=rituximab plus cyclophosphamide, doxorubicin, vincristine, and prednisone; reduced-dose R-CHOP=<80% standard dose cyclophosphamide and doxorubicin; R-mono=rituximab monotherapy; R-Benda=rituximab plus bendamustine; R-CVP=rituximab plus cyclophosphamide, vincristine, and prednisolone; R-Len=rituximab plus lenalidomide.

Figure 3:
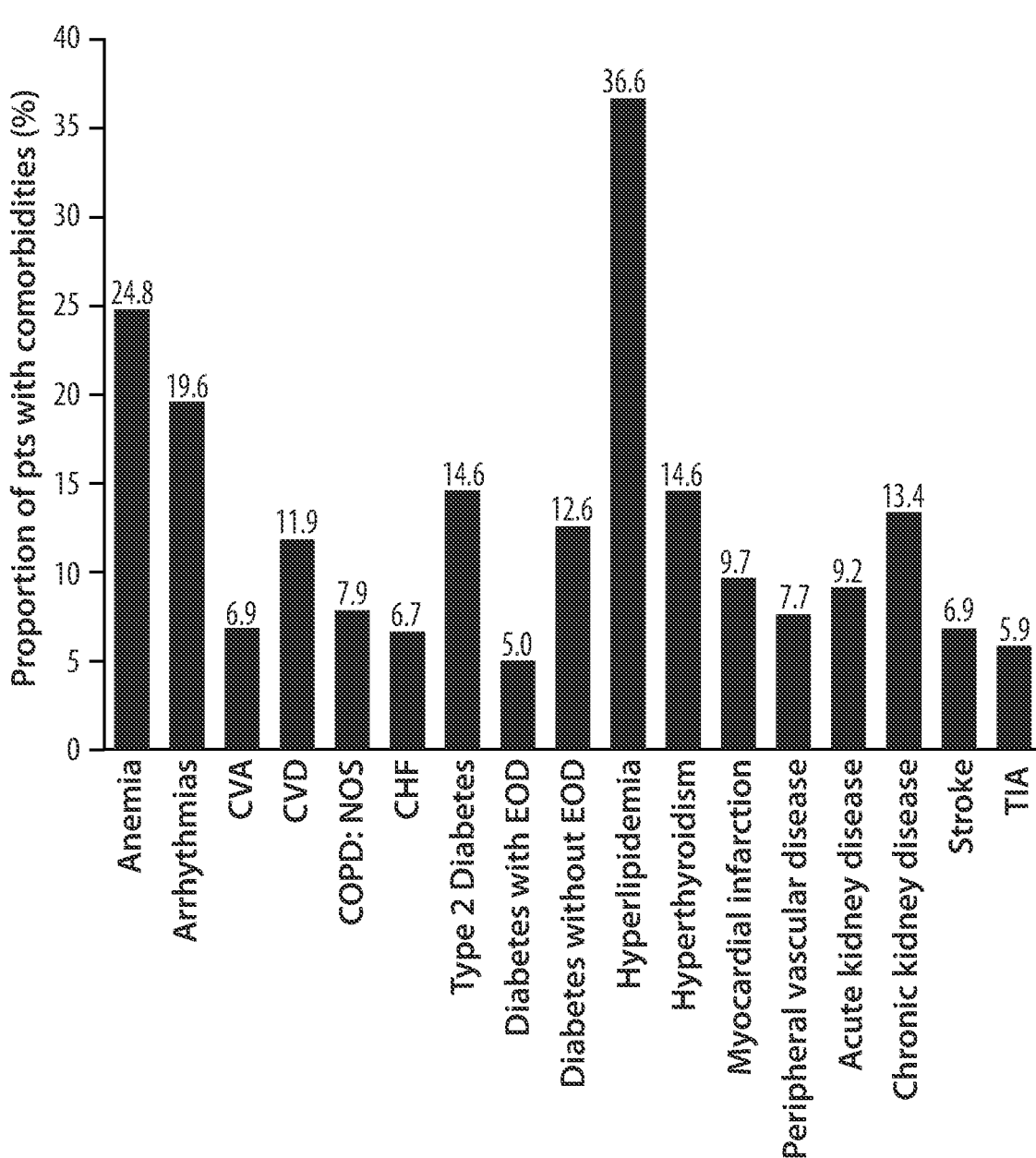

FIG. 3 is a figure showing the percentage of patients of the study described in Example 2 with the indicated comorbidities. Only comorbidities with incidence rate ≥5% were reported. CHF=congestive heart failure; COPD: NOS=chronic obstructive pulmonary disease not otherwise specified; CVA=cerebrovascular accident; CVD=cerebrovascular disease; EOD=end organ damage; TIA=transient ischemic attack.

Figures 4A, 4B:
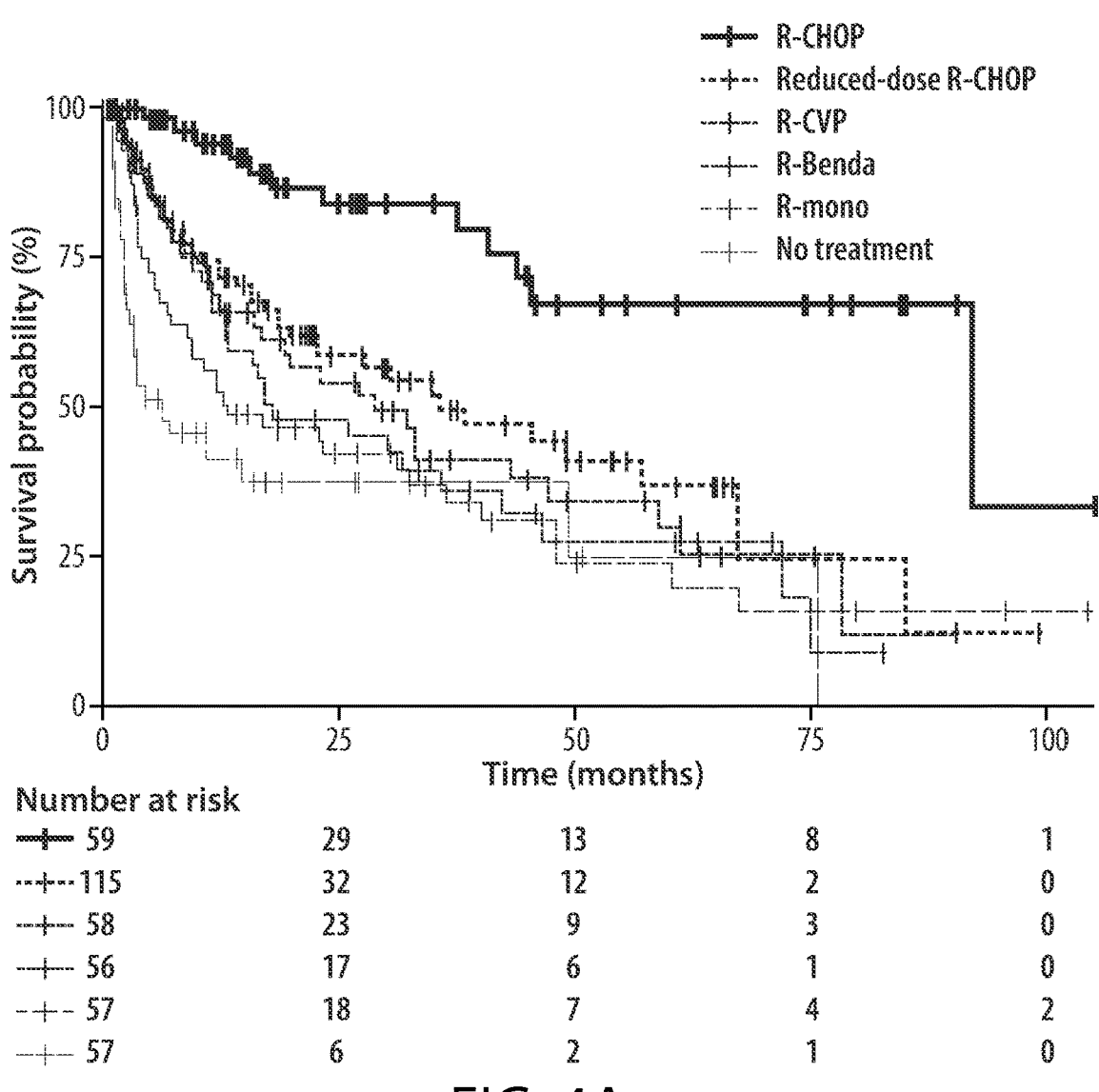

FIG. 4A is a figure showing the overall survival of patients, grouped by treatment status. The numbers below the figure reports the number of patients with each treatment status (as indicated by the line on the left in each row) at the indicated time points (in months of treatment, as shown in the x-axis value above each corresponding column). Overall survival (OS) is calculated from the time of initial DLBCL diagnosis.

FIG. 4B is a table summarizing the data in FIG. 4A. **: patients with no record of any systemic treatment or radiotherapy. NR=not reached.

Figures 5A, 5B:
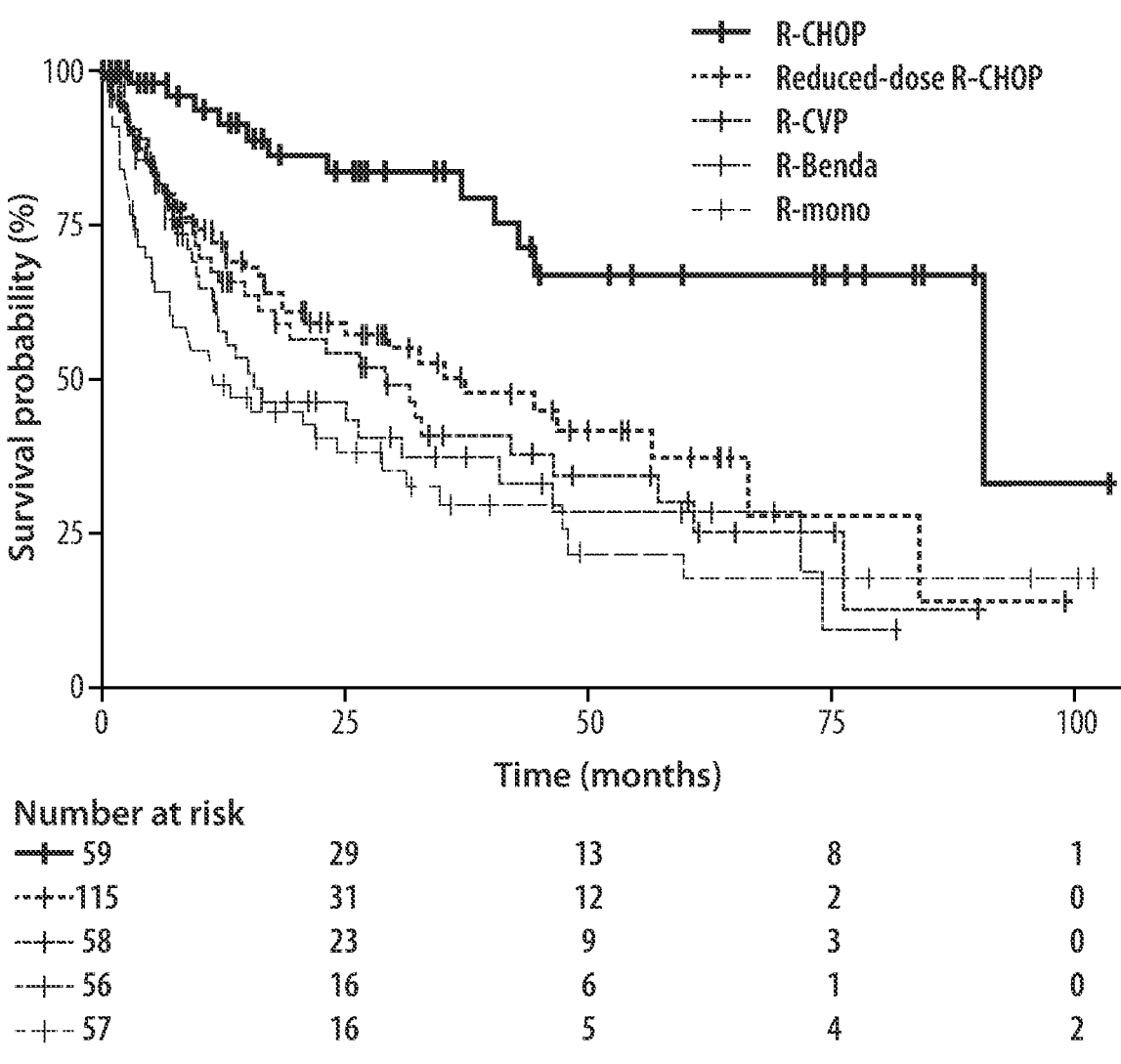

FIG. 5A is a figure showing the overall survival of patients, grouped by first-line (1 L) treatment. The numbers below the figure reports the number of patients undergoing each form of 1 L treatment (as indicated by the line on the left in each row) at the indicated time points (in months of treatment, as shown in the x-axis value above each corresponding column). Overall survival (OS) is calculated from the start of 1 L treatment to death or last visit/admin date.

FIG. 5B is a table summarizing the data in FIG. 5A. NR=not reached.

FIG. 6 is a table showing the most commonly reported rationales that influence the choice of first-line (1 L) treatment in patients receiving systemic treatment and ratio therapy. #Percentage represents the proportion of pts from the total number of documented rationales per each specific treatment group. **Data for R-Len-treated pts (n=2) are not included due to small sample size available. #Pts with no record of any systemic treatment or radiotherapy. ‡As per the recommendations for the use of Flatiron Health data, the percentage values are specified for cell counts of ≥5 only. IPI=international prognostic index; PS=performance state.

Figure 7:
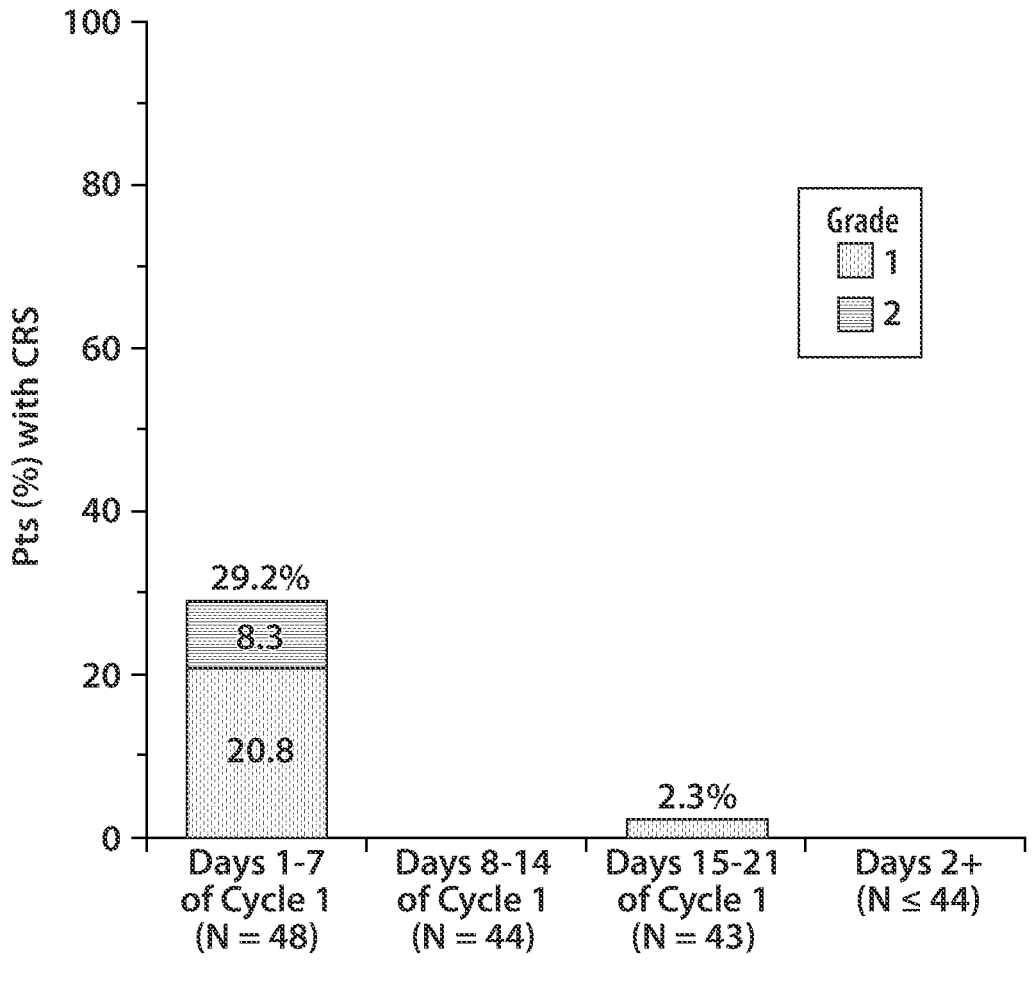

FIG. 7 is a figure showing the percentage of patients of the study described in Example 3 that experienced CRS (ASTCT®; as defined by Lee et al. 2019 criteria) events, broken down by the timing of the CRS event.

Figure 8A:
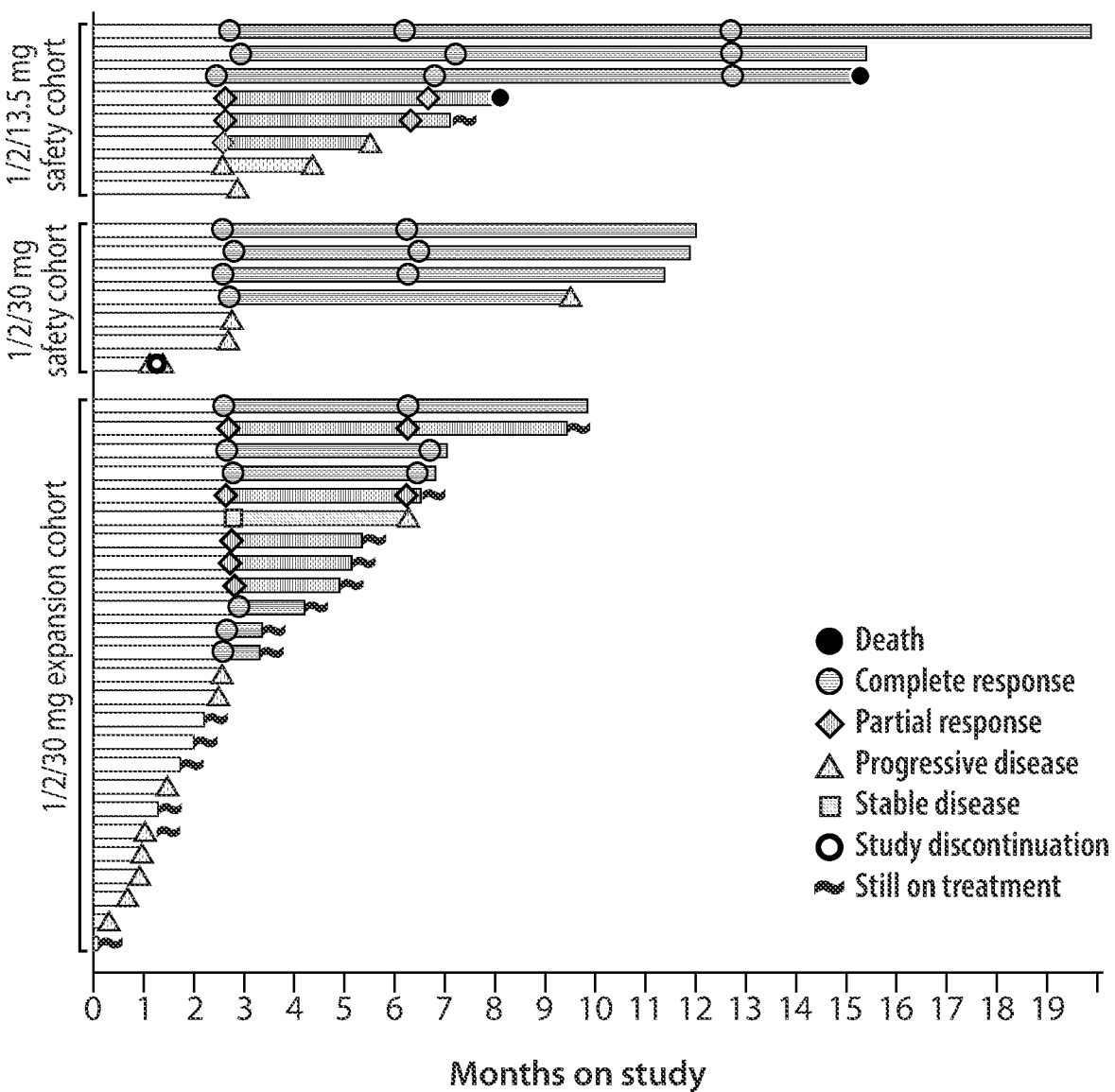

FIG. 8A is a figure showing the durations of response of all efficacy-evaluable 1 L DLBCL patients of the study described in Example 3 with a data cut-off date of Jan. 15, 2021. Each horizontal bar reports the duration of response of a patient, grouped according to the experimental cohort of the patients (1/2/13.5 mg dosing safety, 1/2/30 mg dosing safety, and 1/2/30 mg expansion).

Figure 8B:
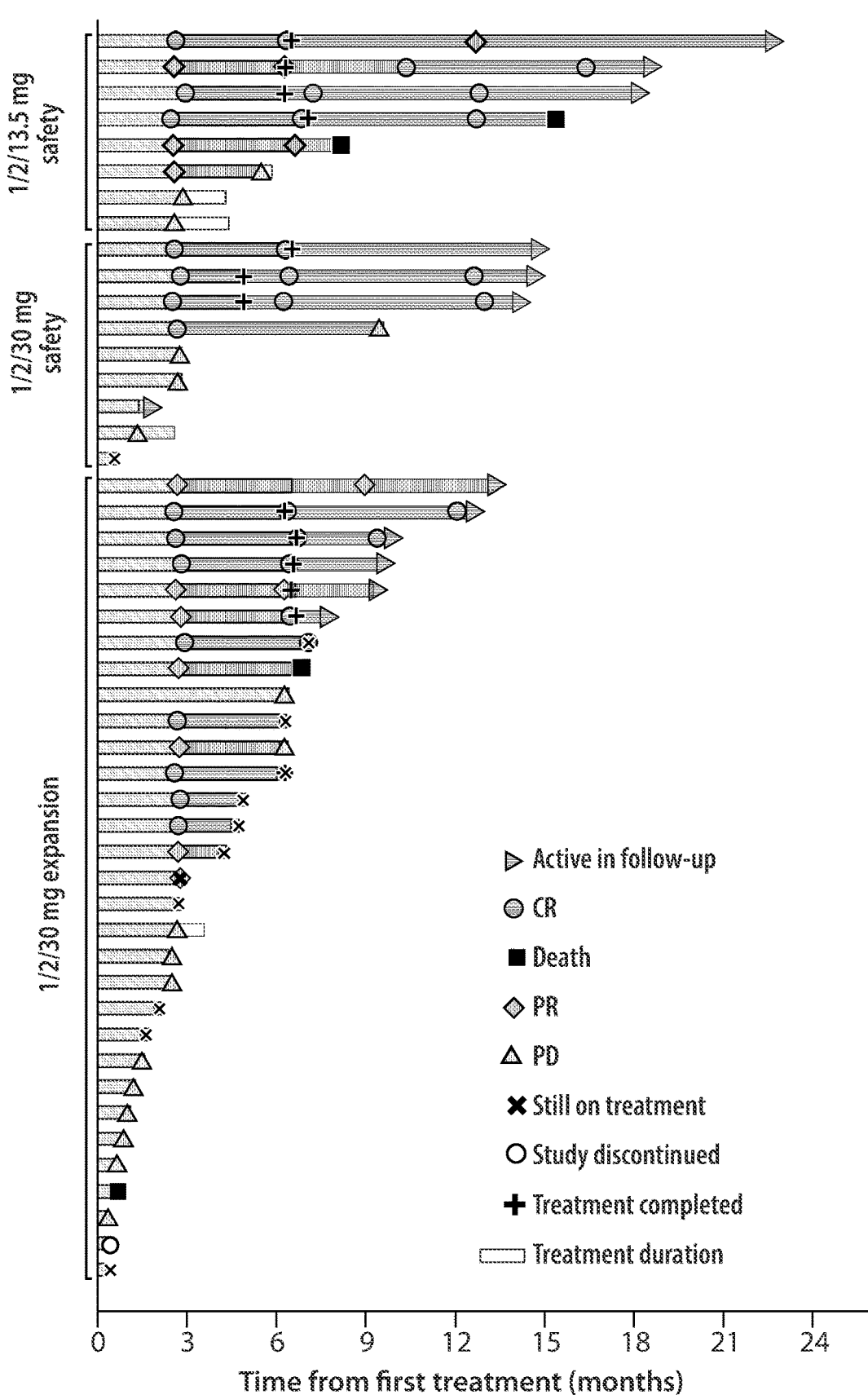

FIG. 8B is a figure showing the durations of response of all efficacy-evaluable 1 L DLBCL patients of the study described in Example 3 with a data cut-off date of Apr. 12, 2021. Each horizontal bar reports the duration of response of a patient, grouped according to the experimental cohort of the patients (1/2/13.5 mg dosing safety, 1/2/30 mg dosing safety, and 1/2/30 mg expansion).

Figure 9A:
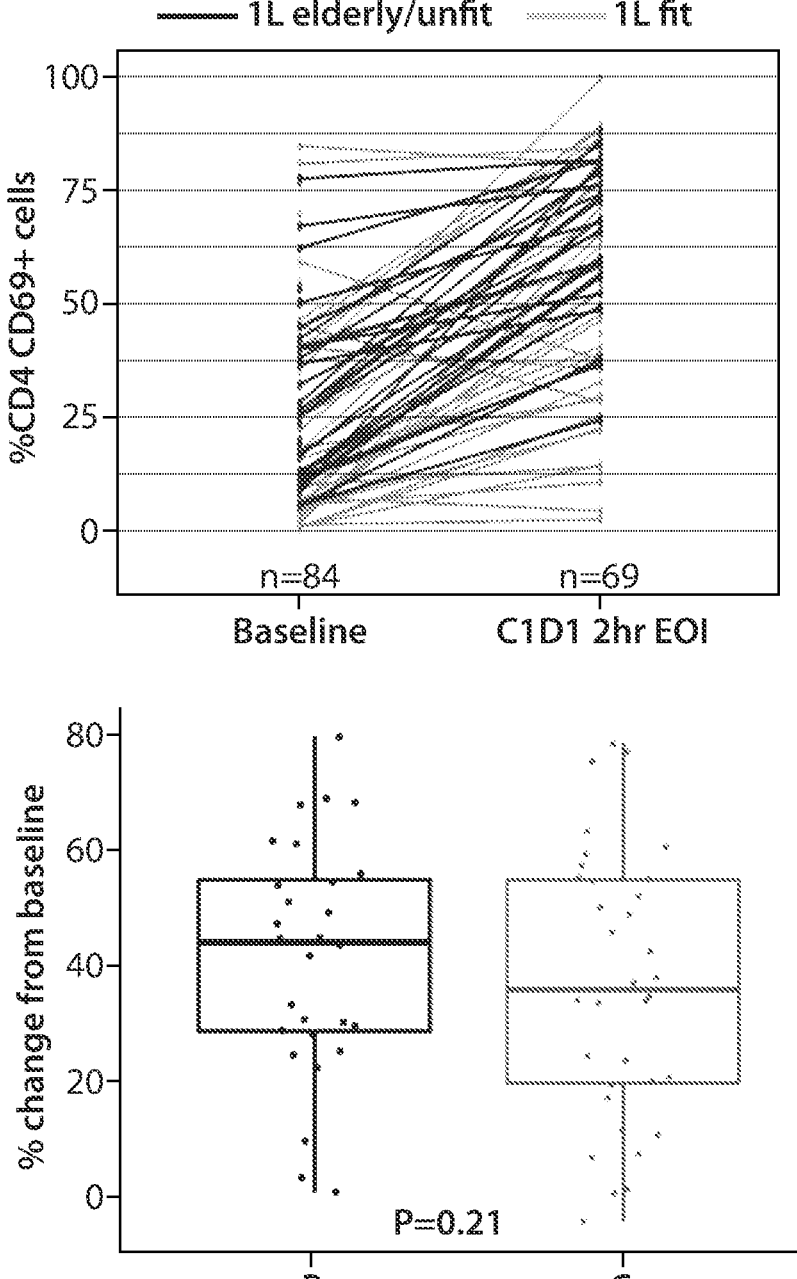

FIG. 9A are figures comparing CD4 T-cell activation in previously untreated (1 L) elderly/unfit vs 1 L fit patients. CD4 T-cell activation is measured at baseline and at 2 hours after end of infusion of the C1D1 dose of mosunetuzumab (left panel). There is no statistical significance between 1 L elderly/unfit patients vs 1 L fit patients in terms of % change from baseline to 2 hours after end of infusion (right panel; p=0.21).

FIG. 9B are figures comparing CD8 T-cell activation in previously untreated (1 L) elderly/unfit vs 1 L fit patients. CD8 T-cell activation is measured at baseline and at 2 hours after end of infusion of the C1D1 dose of mosunetuzumab (left panel). There is no statistical significance between 1 L elderly/unfit patients vs 1 L fit patients in terms of % change from baseline to 2 hours after end of infusion (right panel; p=0.43).

FIG. 9C are figures comparing interferon gamma (IFN-γ) induction in previously untreated (1 L) elderly/unfit vs 1 L fit patients. CD4 T-cell activation is measured at baseline and at 2 hours after end of infusion of the C1D1 dose of mosunetuzumab (left panel). There is no statistical significance between 1 L elderly/unfit patients vs 1 L fit patients in terms of log-fold change from baseline to 2 hours after end of infusion (right panel; p=0.53).

DETAILED DESCRIPTION

The present invention involves methods of treating a subject (or a population of subjects) having a previously untreated (1 L) B cell proliferative disorder (e.g., 1 L non-Hodgkin's lymphoma (NHL) (e.g., 1 L diffuse-large B cell lymphoma (DLBCL)) or 1 L high grade B-cell lymphoma) by intravenously administering to the subject an anti-CD20/anti-CD3 bispecific antibody (e.g., mosunetuzumab) in fractionated, dose-escalation dosing regimen. The method comprises at least a first dosing cycle and a second dosing cycle, wherein: the first dosing cycle comprises a first dose (C1D1), a second dose (C1D2), and a third dose (C1D3) of the anti-CD20/anti-CD3 bispecific antibody (e.g., mosunetuzumab), wherein the C1D1 is 1 mg, the C1D2 is 2 mg, and the C1D3 is 13.5 or 30 mg; and the second dosing cycle comprises a single dose (C2D1) of the anti-CD20/anti-CD3 bispecific antibody (e.g., mosunetuzumab), wherein the C2D1 is equivalent in amount to the C1D3.

The invention is based, in part, on the discovery that dosing regimens involving intravenous administration of an anti-CD20/anti-CD3 antibody (e.g., mosunetuzumab) over multiple dosing cycles (e.g., wherein the first dosing cycle is a step-up, fractionated dosing cycle) can effectively treat subjects (e.g., elderly subjects, unfit subject, or subjects unsuitable for treatment with R-CHOP therapy) having a previously untreated B cell proliferative disorder while maintaining an acceptable safety profile (e.g., with respect to frequency and severity of adverse events).

I. GENERAL TECHNIQUES

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): PCR 2*: A Practical Approach* (M. J. MacPherson, B. D. Hames and G. R. Taylor eds. (1995)), Harlow and Lane, eds. (1988) *Antibodies, A Laboratory Manual, and Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

II. DEFINITIONS

It is to be understood that aspects and embodiments of the invention described herein include "comprising," "consisting," and "consisting essentially of" aspects and embodiments.

As used herein, the singular form "a," "an," and "the" includes plural references unless indicated otherwise.

The term "about" as used herein refers to the usual error range for the respective value readily known to the skilled person in this technical field. Reference to "about" a value or parameter herein includes (and describes) embodiments that are directed to that value or parameter per se.

The terms "cancer" and "cancerous" refer to or describe the physiological condition in mammals that is typically characterized by unregulated cell growth. Examples of cancer include, but are not limited to, hematologic cancers, such as mature B cell cancers, excluding Hodgkin's lymphoma, but including non-Hodgkin's lymphoma (NHL), such as diffuse large B cell lymphoma (DLBCL), which may be relapsed or refractory DLBCL or a Richter's transformation. Other specific examples of cancer also include germinal-center B cell-like (GCB) diffuse large B cell lymphoma (DLBCL), activated B cell-like (ABC) DLBCL, follicular lymphoma (FL), transformed FL, mantle cell lymphoma (MCL), acute myeloid leukemia (AML), chronic lymphoid leukemia (CLL), marginal zone lymphoma (MZL), transformed MZL, high grade B-cell lymphoma, primary mediastinal (thymic) large B cell lymphoma (PMLBCL), small lymphocytic leukemia (SLL), lymphoplasmacytic lymphoma (LL), transformed LL, Waldenstrom macroglobulinemia (WM), central nervous system lymphoma (CNSL), Burkitt's lymphoma (BL), B cell prolymphocytic leukemia, splenic marginal zone lymphoma, hairy cell leukemia, splenic lymphoma/leukemia, unclassifiable, splenic diffuse red pulp small B cell lymphoma, hairy cell leukemia variant, heavy chain diseases, α heavy chain disease, γ heavy chain disease, μ heavy chain disease, plasma cell myeloma, solitary plasmacytoma of bone, extraosseous plasmacytoma, extranodal marginal zone lymphoma of mucosa-associated lymphoid tissue (MALT lymphoma), nodal marginal zone lymphoma, pediatric nodal marginal zone lymphoma, pediatric follicular lymphoma, primary cutaneous follicle centre lymphoma, T cell/histiocyte rich large B cell lymphoma, primary DLBCL of the CNS, primary cutaneous DLBCL, leg type, EBV-positive DLBCL of the elderly, DLBCL associated with chronic inflammation, lymphomatoid granulomatosis, intravascular large B cell lymphoma, ALK-positive large B cell lymphoma, plasmablastic lymphoma, large B cell lymphoma arising in HHV8-associated multicentric Castleman disease, primary effusion lymphoma: B cell lymphoma, unclassifiable, with features intermediate between DLBCL and Burkitt lymphoma, and B cell lymphoma, unclassifiable, with features intermediate between DLBCL and classical Hodgkin's lymphoma. Further examples of cancer include, but are not limited to, carcinoma, lymphoma, blastoma, sarcoma, and leukemia or lymphoid malignancies, including B cell lymphomas. More particular examples of such cancers include, but are not limited to, multiple myeloma (MM); low-grade/follicular NHL; small lymphocytic (SL) NHL; intermediate-grade/follicular NHL; intermediate-grade diffuse NHL; high-grade immunoblastic NHL; high-grade lymphoblastic NHL; high-grade small non-cleaved cell NHL; bulky disease NHL; AIDS-related lymphoma; and acute lymphoblastic leukemia (ALL); chronic myeloblastic leukemia; and post-transplant lymphoproliferative disorder (PTLD).

"Tumor," as used herein, refers to all neoplastic cell growth and proliferation, whether malignant or benign, and all pre-cancerous and cancerous cells and tissues. The terms "cancer", "cancerous", "cell proliferative disorder", "proliferative disorder," and "tumor" are not mutually exclusive as referred to herein.

A "disorder" is any condition that would benefit from treatment including, but not limited to, chronic and acute disorders or diseases including those pathological conditions which predispose the mammal to the disorder in question.

The terms "cell proliferative disorder" and "proliferative disorder" refer to disorders that are associated with some degree of abnormal cell proliferation. In one embodiment, the cell proliferative disorder is cancer. In another embodiment, the cell proliferative disorder is a tumor.

The terms "B cell proliferative disorder" or "B cell malignancy" refer to disorders that are associated with some degree of abnormal B cell proliferation and include, for example, lymphomas, leukemias, myelomas, and myelodysplastic syndromes. In some instances, the B cell proliferative disorder is a lymphoma, such as non-Hodgkin's lymphoma (NHL), including, for example, diffuse large B cell lymphoma (DLBCL) (e.g., a relapsed or refractory DLBCL or a Richter's transformation), FL (e.g., a relapsed and/or refractory FL or transformed FL), MCL, high grade B-cell lymphoma, or PMLBCL). In another embodiment, the B cell proliferative disorder is a leukemia, such as chronic lymphocytic leukemia (CLL). In one embodiment, the B-cell proliferative disorder is a previously untreated (1 L) B cell proliferative disorder (e.g., 1 L non-Hodgkin's lymphoma (NHL) (e.g., 1 L diffuse-large B cell lymphoma (DLBCL)) or 1 L high grade B-cell lymphoma).

As used herein, "treatment" (and grammatical variations thereof, such as "treat" or "treating") refers to clinical intervention in an attempt to alter the natural course of the subject being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

As used herein, "delaying progression" of a disorder or disease means to defer, hinder, slow, retard, stabilize, and/or postpone development of the disease or disorder (e.g., a previously untreated (1 L) B cell proliferative disorder (e.g., 1 L non-Hodgkin's lymphoma (NHL) (e.g., 1 L diffuse-large B cell lymphoma (DLBCL)) or 1 L high grade B-cell lymphoma)). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

By "reduce" or "inhibit" is meant the ability to cause an overall decrease, for example, of 20%, 30%, 40%, 50%, 60%, 70%, 75%, 80%, 85%, 90%, 95%, or greater. For clarity the term includes also reduction to zero (or below the detection limit of the analytical method), i.e., complete abolishment or elimination. In certain embodiments, reduce or inhibit can refer to the reduction or inhibition of undesirable events, such as cytokine-driven toxicities (e.g., cytokine release syndrome (CRS)), infusion-related reactions (IRRs), macrophage activation syndrome (MAS), neurologic toxicities, severe tumor lysis syndrome (TLS), neutropenia, thrombocytopenia, elevated liver enzymes, and/or central nervous system (CNS) toxicities, following treatment with an anti-CD20/anti-CD3 bispecific antibody using the step-up dosing regimen of the invention relative to unchanging, preset dosing with the target dose of the bispecific antibody. In other embodiments, reduce or inhibit can refer to effector function of an antibody that is mediated by the antibody Fc region, such effector functions specifically including complement-dependent cytotoxicity (CDC), antibody-dependent cellular cytotoxicity (ADCC), and antibody-dependent cellular phagocytosis (ADCP). In other embodiments reduce or inhibit can refer to the symptoms of the CD20-positive B cell proliferative disorder being treated (e.g., an NHL (e.g., a DLBCL), an FL (e.g., a relapsed and/or refractor FL or a transformed FL), an MCL, a high-grade B cell lymphoma, or a PMLBCL), the presence or size of metastases, or the size of the primary tumor. In yet other embodiments, reducing or inhibiting cancer relapse means to reduce or inhibit tumor or cancer relapse, or tumor or cancer progression.

As used herein, "administering" is meant a method of giving a dosage of a compound (e.g., a bispecific antibody) or a composition (e.g., a pharmaceutical composition, e.g., a pharmaceutical composition including a bispecific antibody) to a subject. The compounds and/or compositions utilized in the methods described herein can be administered intravenously (e.g., by intravenous infusion).

A "fixed" or "flat" dose of a therapeutic agent (e.g., a bispecific antibody) herein refers to a dose that is administered to a patient without regard for the weight or body surface area (BSA) of the patient. The fixed or flat dose is therefore not provided as a mg/kg dose or a mg/m$^2$ dose, but rather as an absolute amount of the therapeutic agent (e.g., mg).

A "subject" or an "individual" is a mammal. Mammals include, but are not limited to, primates (e.g., humans and non-human primates such as monkeys), domesticated animals (e.g., cows, sheep, cats, dogs, and horses), rabbits, and rodents (e.g., mice and rats). In certain embodiments, the subject or individual is a human.

By an "elderly" subject is meant a human subject who is 60-years of age or older. In some embodiments, an elderly patient may be 65-years of age or older. In a particular embodiment, an elderly patient may be 80-years of age or older.

By an "unsuitable" subject, as used herein, is meant a subject who is considered by an attending physician to be physically inappropriate for treatment with a defined therapy. In some embodiments, the subject may be unsuitable due to a disorder, disability, or condition that precludes safe administration of one or more doses of the therapy. In some embodiments, the subject is unsuitable for treatment with chemotherapy or chemoimmunotherapy (CIT), including, e.g., R-CHOP (rituximab plus cyclophosphamide, doxorubicin, vincristine, and prednisone), reduced-dose R-CHOP (<80% standard dose cyclophosphamide and doxorubicin), R-mono (rituximab monotherapy), R-Benda (rituximab plus bendamustine), R-CVP (rituximab plus cyclophosphamide, vincristine, and prednisolone), and/or R-Len (rituximab plus lenalidomide). In a particular embodiment, the subject may be unsuitable for treatment with standard, full-dose R-CHOP.

By an "unfit" subject, as used herein, is meant a subject who is at least 60-years of age and who has a disorder, disability, or condition that precludes safe administration of one or more doses of a therapy. In some embodiments, the subject is unfit for treatment with chemotherapy or chemoimmunotherapy (CIT), including, e.g., R-CHOP (rituximab plus cyclophosphamide, doxorubicin, vincristine, and prednisone), reduced-dose R-CHOP (<80% standard dose cyclophosphamide and doxorubicin), R-mono (rituximab monotherapy), R-Benda (rituximab plus bendamustine), R-CVP (rituximab plus cyclophosphamide, vincristine, and prednisolone), and/or R-Len (rituximab plus lenalidomide). In a particular embodiment, the subject may be unfit for treatment with standard, full-dose R-CHOP. In some embodiments, the subject may be impaired. In some embodiments, the subject may have one or more impairments selected from the list comprising impaired Activities of Daily Living (ADL), impaired Instrumental Activities of Daily Living (IADL), impaired cardiac function (e.g., heart arrhythmia, congestive heart failure (CHF), myocardial infarction, and/or cardiac-related symptoms of hypothyroidism), impaired vascular function (e.g., anemia, cerebrovascular accident (CVA), cerebrovascular disease (CVD), chronic obstructive pulmonary disease not otherwise specified (COPD: NOS), hyperlipidemia, peripheral vascular disease, stroke, and/or ischemic attack (TIA)), impaired renal function (e.g., acute kidney disease and/or chronic kidney disease), impaired liver function, and diabetes (e.g., type 2 diabetes, diabetes with end organ damage (EOD), and/or diabetes without EOD).

By "ADL" is meant Activities of Daily Living, the Katz Index of Independence in Activities of daily living, or Katz ADL, as defined in Katz et al., *Gerentologist,* 1970, 10(1): 20-30. ADL comprises a score or an index reflecting a subject's independence in daily activities, comprising bathing, dressing, toileting, transferring, continence, and feeding. Higher scores reflect greater independence, and lower scores reflect lower independence.

By "IADL" is meant Instrumental Activities of Daily Living, Lawton Instrumental Activities of Daily Living, or Lawton-Brody Instrumental Activities of Daily Living, as defined in Lawton and Brody, Gerontologist, 1969, 9(3): 179-186. IADL comprises a score or an index reflecting a subject's independence in daily activities, comprising ability to use telephone, shopping, food preparation, housekeeping, laundry, mode of transportation, responsibility for own medications, and ability to handle finances. Higher scores reflect greater independence, and lower scores reflect lower independence.

"Individual response" or "response" can be assessed using any endpoint indicating a benefit to the subject, including, without limitation, (1) inhibition, to some extent, of disease progression (e.g., progression of a previously untreated (1 L) B cell proliferative disorder (e.g., 1 L non-Hodgkin's lymphoma (NHL) (e.g., 1 L diffuse-large B cell lymphoma (DLBCL)) or 1 L high grade B-cell lymphoma), including slowing down and complete arrest; (2) a reduction in tumor size; (3) inhibition (i.e., reduction, slowing down or complete stopping) of cancer cell infiltration into adjacent peripheral organs and/or tissues; (4) inhibition (i.e., reduction, slowing down or complete stopping) of metastasis; (5) relief, to some extent, of one or more symptoms associated with the previously untreated (1 L) B cell proliferative disorder (e.g., 1 L non-Hodgkin's lymphoma (NHL) (e.g., 1 L diffuse-large B cell lymphoma (DLBCL)) or 1 L high grade B-cell lymphoma); (6) increase or extend in the length of survival, including overall survival and progression-free survival; and/or (9) decreased mortality at a given point of time following treatment.

As used herein, "complete response" or "CR" refers to disappearance of all target lesions (i.e., all evidence of disease).

As used herein, "partial response" or "PR" refers to at least a 30% decrease in the sum of the longest diameters (SLD) of target lesions, taking as reference the baseline SLD, or at least a 50% decrease in the product of the diameters (SPD) of target lesions, taking as reference the baseline SPD.

As used herein, "objective response rate" (ORR) refers to the sum of complete response (CR) rate and partial response (PR) rate.

As used herein, "duration of objective response" (DOR) is defined as the time from the first occurrence of a documented objective response to disease progression, or death from any cause within 30 days of the last dose of a treatment, whichever occurs first.

"Sustained response" refers to the sustained effect on reducing tumor growth after cessation of a treatment. For example, the tumor size may remain to be the same or smaller as compared to the size at the beginning of the administration phase. In some embodiments, the sustained response has a duration at least the same as the treatment duration, at least 1.5×, 2.0×, 2.5×, or 3.0× length of the treatment duration.

An "effective response" of a subject or a subject's "responsiveness" to treatment with a medicament and similar wording refers to the clinical or therapeutic benefit imparted to a subject as risk for, or suffering from, a disease or disorder, such as cancer. In one embodiment, such benefit includes any one or more of: extending survival (including overall survival and progression free survival); resulting in an objective response (including a complete response or a partial response); or improving signs or symptoms of cancer.

A subject who "does not have an effective response" to treatment refers to a subject who does not have any one of extending survival (including overall survival and progression free survival); resulting in an objective response (including a complete response or a partial response); or improving signs or symptoms of cancer.

As used herein, "survival" refers to the patient remaining alive, and includes overall survival as well as progression-free survival.

As used herein, "overall survival" (OS) refers to the percentage of subjects in a group who are alive after a particular duration of time, e.g., 1 year or 5 years from the time of diagnosis or treatment.

As used herein, "progression-free survival" (PFS) refers to the length of time during and after treatment during which the disease being treated (e.g., a previously untreated (1 L) B cell proliferative disorder (e.g., 1 L non-Hodgkin's lymphoma (NHL) (e.g., 1 L diffuse-large B cell lymphoma (DLBCL)) or 1 L high grade B-cell lymphoma)) does not get worse. Progression-free survival may include the amount of time patients have experienced a complete response or a partial response, as well as the amount of time patients have experienced stable disease.

As used herein, "stable disease" or "SD" refers to neither sufficient shrinkage of target lesions to qualify for PR, nor sufficient increase to qualify for PD, taking as reference the smallest SLD since the treatment started.

As used herein, "progressive disease" or "PD" refers to at least a 20% increase in the SLD of target lesions, taking as reference the smallest SLD, or at least a 50% increase in the SPD of target legions, taking as reference the smallest SPD, recorded since the treatment started or the presence of one or more new lesions.

As used herein, "delaying progression" of a disorder or disease means to defer, hinder, slow, retard, stabilize, and/or postpone development of the disease or disorder (e.g., a previously untreated (1 L) B cell proliferative disorder (e.g., 1 L non-Hodgkin's lymphoma (NHL) (e.g., 1 L diffuse-large B cell lymphoma (DLBCL)) or 1 L high grade B-cell lymphoma)). This delay can be of varying lengths of time, depending on the history of the disease and/or subject being treated. As is evident to one skilled in the art, a sufficient or significant delay can, in effect, encompass prevention, in that the subject does not develop the disease. For example, in a late stage cancer, development of central nervous system (CNS) metastasis, may be delayed.

By "extending survival" is meant increasing overall or progression free survival in a treated patient relative to an untreated patient (e.g., relative to a patient not treated with the medicament), or relative to a patient who does not express a biomarker at the designated level, and/or relative to a patient treated with an approved anti-tumor agent. An objective response refers to a measurable response, including complete response (CR) or partial response (PR).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; single-chain antibody molecules (e.g., scFv); and multispecific antibodies formed from antibody fragments.

The terms "full-length antibody," "intact antibody," and "whole antibody" are used herein interchangeably to refer to an antibody having a structure substantially similar to a native antibody structure or having heavy chains that contain an Fc region as defined herein.

By "binding domain" is meant a part of a compound or a molecule that specifically binds to a target epitope, antigen, ligand, or receptor. Binding domains include but are not limited to antibodies (e.g., monoclonal, polyclonal, recombinant, humanized, and chimeric antibodies), antibody fragments or portions thereof (e.g., Fab fragments, Fab'$_2$, scFv antibodies, SMIP, domain antibodies, diabodies, minibodies, scFv-Fc, affibodies, NANOBODIES®, and VH and/or VL domains of antibodies), receptors, ligands, aptamers, and other molecules having an identified binding partner.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, MD, 1991.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term IgG "isotype" or "subclass" as used herein is meant any of the subclasses of immunoglobulins defined by the chemical and antigenic characteristics of their constant regions.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3. In one embodiment, for the VL, the subgroup is subgroup kappa I as in Kabat et al., supra. In one embodiment, for the VH, the subgroup is subgroup III as in Kabat et al., supra.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227:381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Nat. Acad. Sci. USA*, 103:3557-3562 (2006) regarding human antibodies generated via a human B-cell hybridoma technology.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, MD (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

The term an "isolated antibody" when used to describe the various antibodies disclosed herein, means an antibody that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or non-proteinaceous solutes. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For a review of methods for assessment of antibody purity, see, e.g., Flatman et al., *J. Chromatogr. B* 848:79-87 (2007). In preferred embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated antibody includes antibodies in situ within recombinant cells, because at least one component of the polypeptide natural environment will not be present. Ordinarily, however, isolated polypeptide will be prepared by at least one purification step.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-CD3 antibody" and "an antibody that binds to CD3" refer to an antibody that is capable of binding CD3 with sufficient affinity such that the antibody is useful as a diagnostic and/or therapeutic agent in targeting CD3. In one embodiment, the extent of binding of an anti-CD3 antibody to an unrelated, non-CD3 protein is less than about 10% of the binding of the antibody to CD3 as measured, e.g., by a radioimmunoassay (RIA). In certain embodiments, an antibody that binds to CD3 has a dissociation constant ($K_D$) of $\leq 1$ μM, $\leq 100$ nM, $\leq 10$ nM, $\leq 1$ nM, $\leq 0.1$ nM, $\leq 0.01$ nM, or $\leq 0.001$ nM (e.g., $10^{-8}$ M or less, e.g., from $10^{-8}$ M to $10^{-13}$ M, e.g., from $10^{-9}$ M to $10^{-13}$ M). In certain embodiments, an anti-CD3 antibody binds to an epitope of CD3 that is conserved among CD3 from different species.

The term "cluster of differentiation 3" or "CD3," as used herein, refers to any native CD3 from any vertebrate source, including mammals such as primates (e.g., humans) and rodents (e.g., mice and rats), unless otherwise indicated, including, for example, CD3ε, CD3γ, CD3α, and CD3β chains. The term encompasses "full-length," unprocessed CD3 (e.g., unprocessed or unmodified CD3ε or CD3γ), as well as any form of CD3 that results from processing in the cell. The term also encompasses naturally occurring variants of CD3, including, for example, splice variants or allelic variants. CD3 includes, for example, human CD3ε protein (NCBI® RefSeq No. NP_000724), which is 207 amino acids in length, and human CD3γ protein (NCBI® RefSeq No. NP_000064), which is 182 amino acids in length.

The terms "anti-CD20 antibody" and "an antibody that binds to CD20" refer to an antibody that is capable of binding CD20 with sufficient affinity such that the antibody is useful as a diagnostic and/or therapeutic agent in targeting CD20. In one embodiment, the extent of binding of an anti-CD20 antibody to an unrelated, non-CD20 protein is less than about 10% of the binding of the antibody to CD20 as measured, e.g., by a radioimmunoassay (RIA). In certain embodiments, an antibody that binds to CD20 has a dissociation constant (Kd) of $\leq 1$ μM, $\leq 100$ nM, $\leq 10$ nM, $\leq 1$ nM, $\leq 0.1$ nM, $\leq 0.01$ nM, or $\leq 0.001$ nM (e.g., $10^{-8}$ M or less, e.g., from $10^{-8}$ M to $10^{-13}$ M, e.g., from $10^{-9}$ M to $10^{-13}$ M). In certain embodiments, an anti-CD20 antibody binds to an epitope of CD20 that is conserved among CD20 from different species.

The term "cluster of differentiation 20" or "CD20," as used herein, refers to any native CD20 from any vertebrate source, including mammals such as primates (e.g., humans) and rodents (e.g., mice and rats), unless otherwise indicated. The term encompasses "full-length," unprocessed CD20, as well as any form of CD20 that results from processing in the cell. The term also encompasses naturally occurring variants of CD20, including, for example, splice variants or allelic variants. CD20 includes, for example, human CD20 protein (see, e.g., NCBI® RefSeq Nos. NP_068769.2 and NP_690605.1), which is 297 amino acids in length and may be generated, for example, from variant mRNA transcripts that lack a portion of the 5' UTR (see, e.g., NCBI® RefSeq No. NM_021950.3) or longer variant mRNA transcripts (see, e.g., NCBI® RefSeq No. NM_152866.2).

The terms "anti-CD20/anti-CD3 bispecific antibody," "bispecific anti-CD20/anti-CD3 antibody," and "antibody that binds to CD20 and CD3," or variants thereof, refer to a multispecific antibody (e.g., a bispecific antibody) that is capable of binding to CD20 and CD3 with sufficient affinity such that the antibody is useful as a diagnostic and/or therapeutic agent in targeting CD20 and/or CD3. In one embodiment, the extent of binding of a bispecific antibody that binds to CD20 and CD3 to an unrelated, non-CD3 protein and/or non-CD20 protein is less than about 10% of the binding of the antibody to CD3 and/or CD20 as measured, e.g., by a radioimmunoassay (RIA). In certain embodiments, a bispecific antibody that binds to CD20 and CD3 has a dissociation constant (Kd) of $\leq 1$ µM, $\leq 100$ nM, $\leq 10$ nM, $\leq 1$ nM, $\leq 0.1$ nM, $\leq 0.01$ nM, or $\leq 0.001$ nM (e.g., $10^{-8}$ M or less, e.g., from $10^{-8}$ M to $10^{-13}$ M, e.g., from $10^{-9}$ M to $10^{-13}$ M). In certain embodiments, a bispecific antibody that binds to CD20 and CD3 binds to an epitope of CD3 that is conserved among CD3 from different species and/or an epitope of CD20 that is conserved among CD20 from different species. In one embodiment, the bispecific antibody binds monovalently to CD20 and binds monovalently to CD3. In one embodiment, a bispecific antibody that binds to CD20 and CD3 is mosunetuzumab.

As used herein, the term "mosunetuzumab" refers to an anti-CD20/anti-CD3 bispecific antibody having the International Nonproprietary Names for Pharmaceutical Substances (INN) List 117 (WHO Drug Information, Vol. 31, No. 2, 2017, p. 303), or the CAS Registry® Number 1905409-39-3.

As used herein, the term "binds," "specifically binds to," or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, for example, by a radioimmunoassay (RIA). In certain embodiments, an antibody that specifically binds to a target has a dissociation constant ($K_D$) of $\leq 1$ µM, $\leq 100$ nM, $\leq 10$ nM, $\leq 1$ nM, or $\leq 0.1$ nM. In certain embodiments, an antibody specifically binds to an epitope on a protein that is conserved among the protein from different species. In another embodiment, specific binding can include, but does not require exclusive binding. The term as used herein can be exhibited, for example, by a molecule having a $K_D$ for the target of $10^{-4}$ M or lower, alternatively $10^{-5}$ M or lower, alternatively $10^{-6}$ M or lower, alternatively $10^{-7}$ M or lower, alternatively $10^{-8}$ M or lower, alternatively $10^{-9}$ M or lower, alternatively $10^{-10}$ M or lower, alternatively $10^{-11}$ M or lower, alternatively $10^{-12}$ M or lower or a $K_D$ in the range of $10^{-4}$ M to $10^{-6}$ M or $10^{-6}$ M to $10^{-10}$ M or $10^{-7}$ M to $10^{-9}$ M. As will be appreciated by the skilled artisan, affinity and $K_D$ values are inversely related. A high affinity for an antigen is measured by a low $K_D$ value. In one embodiment, the term "specific binding" refers to binding where a molecule binds to a particular polypeptide or epitope on a particular polypeptide without substantially binding to any other polypeptide or polypeptide epitope.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN® (DNASTAR®) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX® operating system, including digital UNIX® V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, the term "chemotherapeutic agent" refers to a compound useful in the treatment of a cancer, such as a previously untreated (1 L) B cell proliferative disorder (e.g., 1 L non-Hodgkin's lymphoma (NHL) (e.g., 1 L diffuse-large B cell lymphoma (DLBCL)) or 1 L high grade B-cell lymphoma). Examples of chemotherapeutic agents include EGFR inhibitors (including small molecule inhibitors (e.g., erlotinib (TARCEVA®, Genentech/OSI Pharm.); PD 183805 (CI 1033, 2-propenamide, N-[4-[(3-chloro-4-fluorophenyl)amino]-7-[3-(4-morpholinyl)propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl) amino]-1H-pyrrolo[2,3-d]pyrimidin-6-yl]-phenol); (R)-6-(4-hydroxyphenyl)-4-[(1-phenylethyl)amino]-7H-pyrrolo [2,3-d]pyrimidine); CL-387785 (N-[4-[(3-bromophenyl) amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); and dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl)ethyl]amino] methyl]-2-furanyl]-4-quinazolinamine)); a tyrosine kinase inhibitor (e.g., an EGFR inhibitor; a small molecule HER2 tyrosine kinase inhibitor such as TAK165 (Takeda); CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; PKI-166 (Novartis); pan-HER inhibitors such as canertinib (CI-1033; Pharmacia); Raf-1 inhibitors such as antisense agent ISIS-5132 (ISIS Pharmaceuticals) which inhibit Raf-1 signaling; non-HER-targeted tyrosine kinase inhibitors such as imatinib mesylate (GLEEVEC®, Glaxo SmithKline); multi-targeted tyrosine kinase inhibitors such as sunitinib (SUTENT®, Pfizer); VEGF receptor tyrosine kinase inhibitors such as vatalanib (PTK787/ZK222584, Novartis/Schering AG); MAPK extracellular regulated kinase I inhibitor CI-1040 (Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis (4-fluoroanilino) phthalimide); tyrphostines containing nitrothiophene moieties; PD-0183805 (Warner-Lamber); antisense molecules (e.g., those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone); and rapamycin (sirolimus, RAPAMUNE®)); proteasome inhibitors such as bortezomib (VELCADE®, Millennium Pharm.); disulfiram; epigallocatechin gallate; salinosporamide A; carfilzomib; 17-AAG (geldanamycin); radicicol; lactate dehydrogenase A (LDH-A); fulvestrant (FASLODEX®, AstraZeneca); letrozole (FEMARA®, Novartis), finasunate (VATALANIB®, Novartis); oxaliplatin (ELOXATIN®, Sanofi); 5-FU (5-fluorouracil); leucovorin; lonafamib (SCH 66336); sorafenib (NEXAVAR®, Bayer Labs); AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimustine; antibiotics such as the enediyne antibiotics (e.g., calicheamicin, especially calicheamicin γ1 and calicheamicin ω1); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, cactinomycin, carabicin, caminomycin, carzinophilin, chromomycinis, dactinomycin, detorubicin, 6-diazo-5-oxo-L-norleucine, morpholino-doxorubicin, cyanomorpholinodoxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone;

mopidamnol; nitraerine; pentostatin; phenamet; pirarubicin; losoxantrone; podophyllinic acid; 2-ethylhydrazide; procarbazine; PSK® polysaccharide complex (JHS Natural Products); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); thiotepa; chloranmbucil; GEMZAR® (gemcitabine); 6-thioguanine; mercaptopurine; methotrexate; etoposide (VP-16); ifosfamide; mitoxantrone; novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids, prodrugs, and derivatives of any of the above.

Chemotherapeutic agents also include (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; (ix) growth inhibitory agents including vincas (e.g., vincristine and vinblastine), NAVELBINE® (vinorelbine), taxanes (e.g., paclitaxel, nab-paclitaxel, and docetaxel), topoisomerase II inhibitors (e.g., doxorubicin, epirubicin, daunorubicin, etoposide, and bleomycin), and DNA alkylating agents (e.g., tamoxigen, dacarbazine, mechlorethamine, cisplatin, methotrexate, 5-fluorouracil, and ara-C); and (x) pharmaceutically acceptable salts, acids, prodrugs, and derivatives of any of the above.

The term "R-CHOP" as used herein refers to a treatment comprising rituximab plus cyclophosphamide, doxorubicin, vincristine, and prednisone. In some embodiments, R-CHOP is a chemotherapy treatment or regimen used in the treatment of a cancer, optionally a B cell proliferative disorder (e.g., a non-Hodgkin's lymphoma; e.g., a DLBCL or a high grade B-cell lymphoma). In some embodiments, R-CHOP is the standard of care (SOC) or standard therapy to be administered to a subject to treat the cancer, optionally the B cell proliferative disorder (e.g., the non-Hodgkin's lymphoma; e.g., the DLBCL or the high grade B-cell lymphoma). In some embodiments, R-CHOP is the standard front-line or first-line therapy to be administered to a previously untreated subject. In some embodiments, R-CHOP is administered every 3 weeks (in 21-day dosing cycles) for 3 to 6 dosing cycles. In some embodiments, the dosing regimen for R-CHOP therapy comprises 21-day dosing cycles, wherein during each dosing cycle, the subject is administered 375 mg/m$^2$ rituximab IV, and also administered cyclophosphamide, doxorubicin, vincristine, and prednisone. In some embodiments, the dosing regimen for R-CHOP therapy further comprises 750 mg/m$^2$ cyclophosphamide IV, 50 mg/m$^2$ doxorubicin IV, 1.4 mg/m$^2$ vincristine IV, and 5 days of 100 mg or 40 mg/m$^2$ per day prednisone oral. In some embodiments, a maximum single dose of vincristine is 2 mg. In some embodiments, R-CHOP is unsuitable for use as a treatment or unsuitable to be administered to a subject because of the subject's age, low ADL or IADL score, and/or comorbidities of the subject, including, e.g., impairments to cardiac, renal, and/or liver function, as well as one or more comorbidities comprising anemia, arrhythmias, cerebrovascular accident (CVA), cerebrovascular disease (CVD), chronic obstructive pulmonary disease not otherwise specified (COPD: NOS), congestive heart failure (CHF), type 2 diabetes, diabetes with end organ damage (EOD), diabetes without EOD, hyperlipidemia, hypothyroidism, myocardial infarction, peripheral vascular disease, acute kidney disease, chronic kidney disease, stroke, and/or transient ischemic attack (TIA).

The term "cytotoxic agent" as used herein refers to any agent that is detrimental to cells (e.g., causes cell death, inhibits proliferation, or otherwise hinders a cellular function). Cytotoxic agents include, but are not limited to, radioactive isotopes (e.g., $^{211}$At, $^{131}$I, $^{125}$I, $^{90}$Y, $^{186}$Re, $^{188}$Re, $^{153}$Sm, $^{212}$Bi, $^{32}$P, $^{212}$Pb, and radioactive isotopes of Lu); chemotherapeutic agents; enzymes and fragments thereof such as nucleolytic enzymes; and toxins such as small molecule toxins or enzymatically active toxins of bacterial, fungal, plant or animal origin, including fragments and/or variants thereof. Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signaling inhibitors, HDAC inhibitors, proteasome inhibitors, and inhibitors of cancer metabolism. In one instance, the cytotoxic agent is a platinum-based chemotherapeutic agent (e.g., carboplatin or cisplatin). In one instance, the cytotoxic agent is an antagonist of EGFR, e.g., N-(3-ethynylphenyl)-6,7-bis(2-methoxyethoxy)quinazolin-4-amine (e.g., erlotinib). In one instance the cytotoxic agent is a RAF inhibitor, e.g., a BRAF and/or CRAF inhibitor. In one instance the RAF inhibitor is vemurafenib. In one instance, the cytotoxic agent is a PI3K inhibitor.

The term "package insert" is used to refer to instructions customarily included in commercial packages of therapeutic products, that contain information about the indications, usage, dosage, administration, combination therapy, contraindications and/or warnings concerning the use of such therapeutic products.

III. THERAPEUTIC METHODS

Provided herein are methods of treating a subject having a previously untreated (first-line; 1 L) B cell proliferative disorder (e.g., 1 L non-Hodgkin's lymphoma (NHL) (e.g., 1 L diffuse-large B cell lymphoma (DLBCL)) or 1 L high grade B-cell lymphoma) comprising intravenously administering to the subject an anti-CD20/anti-CD3 bispecific antibody (e.g., mosunetuzumab) in a fractionated, dose-escalation dosing regimen. In some instances, the present methods are for treating a subject having a 1 L DLBCL. In some instances, the present methods are for treating a subject having a 1 L high grade B-cell lymphoma. In some instances, the subjects may include elderly subjects, unfit subjects, or subjects unsuitable for treatment with standard chemotherapy or chemoimmunotherapy (CIT).

A. Therapeutic Methods for Dosing of the Anti-CD20/Anti-CD3 Bispecific Antibody (e.g., Mosunetuzumab)

The invention provides methods for treating a subject having a previously untreated (1 L) B cell proliferative disorder (e.g., 1 L non-Hodgkin's lymphoma (NHL) (e.g., 1 L diffuse-large B cell lymphoma (DLBCL)) or 1 L high grade B-cell lymphoma) that includes administering to the subject an anti-CD20/anti-CD3 bispecific antibody (e.g., mosunetuzumab), e.g., in a fractionated, dose-escalation dosing regimen or e.g., in a fractionated step-up dosing regimen in the first dosing cycle. In some embodiments, the present methods are used for treating a subject having a previously untreated NHL, and the present dosing regimen is a first-line therapy.

In some instances, the invention involves treating a subject having a previously untreated B cell proliferative disorder comprising intravenously administering to the subject, as a monotherapy, mosunetuzumab in a dosing regimen comprising at least a first dosing cycle and a second dosing cycle, wherein: the first dosing cycle comprises a first dose (C1D1), a second dose (C1D2), and a third dose (C1D3) of the anti-CD20/anti-CD3 bispecific antibody (e.g., mosunetuzumab), wherein the C1D1 is 1 mg, the C1D2 is 2 mg, and the C1D3 is 13.5 or 30 mg; and the second dosing cycle comprises a single dose (C2D1) of the anti-CD20/anti-CD3 bispecific antibody (e.g., mosunetuzumab), wherein the C2D1 is equivalent in amount to the C1D3.

In some instances, the invention involves treating an elderly subject having a previously untreated B cell proliferative disorder comprising intravenously administering to the subject, as a monotherapy, mosunetuzumab in a dosing regimen comprising at least a first dosing cycle and a second dosing cycle, wherein: (a) the first dosing cycle comprises a first dose (C1D1), a second dose (C1D2), and a third dose (C1D3) of the anti-CD20/anti-CD3 bispecific antibody (e.g., mosunetuzumab), wherein the C1D1 is 1 mg, the C1D2 is 2 mg, and the C1D3 is 13.5 or 30 mg; and (b) the second dosing cycle comprises a single dose (C2D1) of the anti-CD20/anti-CD3 bispecific antibody (e.g., mosunetuzumab), wherein the C2D1 is equivalent in amount to the C1D3. In some embodiments, the elderly subject is at least 60-years old. In some embodiments, the elderly subject is at least 65-years old. In some embodiments, the elderly subject is at least 80-years old.

In one aspect, the invention features a method of treating an unfit subject having a previously untreated B cell proliferative disorder comprising intravenously administering to the subject, as a monotherapy, mosunetuzumab in a dosing regimen comprising at least a first dosing cycle and a second dosing cycle, wherein: (a) the first dosing cycle comprises a first dose (C1D1), a second dose (C1D2), and a third dose (C1D3) of the anti-CD20/anti-CD3 bispecific antibody (e.g., mosunetuzumab), wherein the C1D1 is 1 mg, the C1D2 is 2 mg, and the C1D3 is 13.5 or 30 mg; and (b) the second dosing cycle comprises a single dose (C2D1) of the anti-CD20/anti-CD3 bispecific antibody (e.g., mosunetuzumab), wherein the C2D1 is equivalent in amount to the C1D3. In some embodiments, the unfit subject is at least 60-years old.

In some embodiments, the unfit subject is 60-years to 79-years old. In some embodiments, the unfit subject exhibits: (i) an impairment in at least one activity of daily living (ADL) component; (ii) an impairment in at least one instrumental activity of daily living (IADL) component; (iii) an impairment in at least one of cardiac function, vascular function, renal function, and/or liver function; and/or (iv) diabetes. In some embodiments, the unfit subject exhibits an impairment in at least one ADL component. In some embodiments, the unfit subject exhibits an impairment in at least one IADL component. In some embodiments, the unfit subject exhibits an impairment in cardiac function comprising heart arrhythmia, congestive heart failure (CHF), myocardial infarction, and/or cardiac-related symptoms of hypothyroidism. In some embodiments, the unfit subject exhibits an impairment in vascular function comprising anemia, cerebrovascular accident (CVA), cerebrovascular disease (CVD), chronic obstructive pulmonary disease not otherwise specified (COPD: NOS), hyperlipidemia, peripheral vascular disease, stroke, and/or ischemic attack (TIA). In some embodiments, the unfit subject exhibits an impairment in renal function comprising acute kidney disease and/or chronic kidney disease. In some embodiments, the unfit subject exhibits an impairment in liver function. In some embodiments, the unfit subject exhibits diabetes, comprising type 2 diabetes, diabetes with end organ damage (EOD), and/or diabetes without EOD. In some embodiments, the subject is unsuitable for treatment with R-CHOP therapy.

In one aspect, the invention features a method of treating a subject having a previously untreated B cell proliferative disorder comprising intravenously administering to the subject, as a monotherapy, mosunetuzumab in a dosing regimen comprising at least a first dosing cycle and a second dosing cycle, wherein: (a) the first dosing cycle comprises a first dose (C1D1), a second dose (C1D2), and a third dose (C1D3) of the anti-CD20/anti-CD3 bispecific antibody (e.g., mosunetuzumab), wherein the C1D1 is 1 mg, the C1D2 is 2 mg, and the C1D3 is 13.5 or 30 mg; and (b) the second dosing cycle comprises a single dose (C2D1) of the anti-CD20/anti-CD3 bispecific antibody (e.g., mosunetuzumab), wherein the C2D1 is equivalent in amount to the C1D3, wherein the subject is unsuitable for treatment with R-CHOP therapy.

In some embodiments, the R-CHOP therapy comprises rituximab, cyclophosphamide, doxorubicin, vincristine, and prednisone, and further wherein the rituximab is administered to the subject at a dose of 375 mg/m² every three weeks.

In some embodiments, the C1D3 and the C2D1 are each 13.5 mg. In some embodiments, the C1D3 and the C2D1 are each 30 mg. In some embodiments, the first and second dosing cycles are 21-day dosing cycles. In some embodiments, the method comprises administering the C1D1, the C1D2, and the C1D3 on Days 1, 8 (±1 day), and 15 (±1 day), respectively, of the first dosing cycle. In some embodiments, the method comprises administering the C2D1 on Day 1 (±1 day) of the second dosing cycle.

In some embodiments, the dosing regimen further comprises one or more additional dosing cycles. In some embodiments, the dosing regimen comprises six to 15 additional dosing cycles. In some embodiments, the dosing regimen comprises six additional dosing cycles. In some embodiments, the dosing regimen comprises 15 additional dosing cycles. In some embodiments, the additional dosing cycles are 21-day dosing cycles.

In some embodiments, one or more of the additional dosing cycles comprise an additional single dose of the anti-CD20/anti-CD3 bispecific antibody (e.g., mosunetuzumab). In some embodiments, the additional single dose of the anti-CD20/anti-CD3 bispecific antibody (e.g., mosunetuzumab) is administered to the subject on Day 1 (±1 day) of each additional dosing cycle. In some embodiments, the additional single dose of the anti-CD20/anti-CD3 bispecific antibody (e.g., mosunetuzumab) is equivalent in amount to the C1D3. In some embodiments, the additional single dose of the anti-CD20/anti-CD3 bispecific antibody (e.g., mosunetuzumab) is 13.5 mg. In some embodiments, the additional single dose of the anti-CD20/anti-CD3 bispecific antibody (e.g., mosunetuzumab) is 30 mg.

In some embodiments, the method further comprises administering to the subject one or more additional therapeutic agents. In some embodiments, the one or more additional therapeutic agents is tocilizumab. In some embodiments, the one or more additional therapeutic agents is an antihistamine. In some embodiments, the antihistamine is diphenhydramine. In some embodiments, the one or more additional therapeutic agents comprises allopurinol and rasburicase.

In some embodiments, the one or more additional therapeutic agents is a corticosteroid. In some embodiments, the corticosteroid comprises prednisone, prednisolone, methylprednisolone, and dexamethasone. In some embodiments, the corticosteroid comprises prednisone. In some embodiments, the prednisone is administered to the subject on each of the seven days (±1 day) prior to the administration of the C1D1. In some embodiments, the prednisone is administered at a dose of 100 mg/day.

In some embodiments, the one or more additional therapeutic agents comprises a single dose of vincristine, and wherein the single dose of vincristine is 1 mg. In some embodiments, the single dose of vincristine is administered to the subject seven days (±1 day) prior to the administration of the C1D1.

In some embodiments, the previously untreated B cell proliferative disorder is a previously untreated high-grade B-cell lymphoma. In some embodiments, the previously untreated B cell proliferative disorder is a previously untreated non-Hodgkin's lymphoma (NHL). In some embodiments, the previously untreated NHL is a previously untreated DLBCL.

In one aspect, the invention features a method of treating a subject having a previously untreated B cell proliferative disorder comprising intravenously administering to the subject, as a monotherapy, mosunetuzumab in a dosing regimen comprising eight 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8, and 15, respectively, of the first dosing cycle, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab administered on Day 1 (±1 day) of each dosing cycle, wherein each single dose C2D1-C8D1 is equivalent in amount to the C1D3.

In one aspect, the invention features a method of treating a subject having a previously untreated B cell proliferative disorder comprising intravenously administering to the subject, as a monotherapy, mosunetuzumab in a dosing regimen comprising eight 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 30 mg; and (b) the second to eighth dosing cycles each comprises a single dose (C2D1-C8D1) of mosunetuzumab administered on Day 1 (±1 day) of each dosing cycle, wherein each single dose C2D1-C8D1 is equivalent in amount to the C1D3.

In one aspect, the invention features a method of treating a subject having a previously untreated B cell proliferative disorder comprising intravenously administering to the subject, as a monotherapy, mosunetuzumab in a dosing regimen comprising seventeen 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 13.5 mg; and (b) the second to seventeenth dosing cycles each comprises a single dose (C2D1-C17D1) of mosunetuzumab administered on Day 1 (±1 day) of each dosing cycle, wherein each single dose C2D1-C17D1 is equivalent in amount to the C1D3.

In one aspect, the invention features a method of treating a subject having a previously untreated B cell proliferative disorder comprising intravenously administering to the subject, as a monotherapy, mosunetuzumab in a dosing regimen comprising seventeen 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab administered on Day 1 (±1 day) of each dosing cycle, wherein each single dose C2D1-C17D1 is equivalent in amount to the C1D3.

In one aspect, the invention features a method of treating a subject having a previously untreated DLBCL comprising intravenously administering to the subject, as a monotherapy, mosunetuzumab in a dosing regimen comprising eight 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab administered on Day 1 (±1 day) of each dosing cycle, wherein each single dose C2D1-C8D1 is equivalent in amount to the C1D3.

In one aspect, the invention features a method of treating a subject having a previously untreated DLBCL comprising intravenously administering to the subject, as a monotherapy, mosunetuzumab in a dosing regimen comprising eight 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 30 mg; and (b) the second to eighth dosing cycles each comprises a single dose (C2D1-C8D1) of mosunetuzumab administered on Day 1 (±1 day) of each dosing cycle, wherein each single dose C2D1-C8D1 is equivalent in amount to the C1D3.

In one aspect, the invention features a method of treating a subject having a previously untreated DLBCL comprising intravenously administering to the subject, as a monotherapy, mosunetuzumab in a dosing regimen comprising seventeen 21-day (e.g., 21±3 days) dosing cycles, wherein:

(a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 13.5 mg; and (b) the second to seventeenth dosing cycles each comprises a single dose (C2D1-C17D1) of mosunetuzumab administered on Day 1 (±1 day) of each dosing cycle, wherein each single dose C2D1-C17D1 is equivalent in amount to the C1D3.

In one aspect, the invention features a method of treating a subject having a previously untreated DLBCL comprising intravenously administering to the subject, as a monotherapy, mosunetuzumab in a dosing regimen comprising seventeen 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab administered on Day 1 (±1 day) of each dosing cycle, wherein each single dose C2D1-C17D1 is equivalent in amount to the C1D3.

In one aspect, the invention features a method of treating a subject having a previously untreated DLBCL comprising intravenously administering to the subject, as a monotherapy, mosunetuzumab in a dosing regimen comprising eight 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab administered on Day 1 (±1 day) of each dosing cycle, wherein each single dose C2D1-C8D1 is equivalent in amount to the C1D3, wherein the subject is at least 65-years old, and wherein the subject is unfit for treatment with standard R-CHOP therapy.

In one aspect, the invention features a method of treating a subject having a previously untreated DLBCL comprising intravenously administering to the subject, as a monotherapy, mosunetuzumab in a dosing regimen comprising eight 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 30 mg; and (b) the second to eighth dosing cycles each comprises a single dose (C2D1-C8D1) of mosunetuzumab administered on Day 1 (±1 day) of each dosing cycle, wherein each single dose C2D1-C8D1 is equivalent in amount to the C1D3, wherein the subject is at least 65-years old, and wherein the subject is unfit for treatment with standard R-CHOP therapy.

In one aspect, the invention features a method of treating a subject having a previously untreated DLBCL comprising intravenously administering to the subject, as a monotherapy, mosunetuzumab in a dosing regimen comprising seventeen 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 13.5 mg;

and (b) the second to seventeenth dosing cycles each comprises a single dose (C2D1-C17D1) of mosunetuzumab administered on Day 1 (±1 day) of each dosing cycle, wherein each single dose C2D1-C17D1 is equivalent in amount to the C1D3, wherein the subject is at least 65-years old, and wherein the subject is unfit for treatment with standard R-CHOP therapy.

In one aspect, the invention features a method of treating a subject having a previously untreated DLBCL comprising intravenously administering to the subject, as a monotherapy, mosunetuzumab in a dosing regimen comprising seventeen 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab administered on Day 1 (±1 day) of each dosing cycle, wherein each single dose C2D1-C17D1 is equivalent in amount to the C1D3, wherein the subject is at least 65-years old, and wherein the subject is unfit for treatment with standard R-CHOP therapy.

In one aspect, the invention features a method of treating an elderly subject having a previously untreated DLBCL comprising intravenously administering to the subject, as a monotherapy, mosunetuzumab in a dosing regimen comprising eight 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab administered on Day 1 (±1 day) of each dosing cycle, wherein each single dose C2D1-C8D1 is equivalent in amount to the C1D3, wherein the subject is at least 80-years old.

In one aspect, the invention features a method of treating an elderly subject having a previously untreated DLBCL comprising intravenously administering to the subject, as a monotherapy, mosunetuzumab in a dosing regimen comprising eight 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 30 mg; and (b) the second to eighth dosing cycles each comprises a single dose (C2D1-C8D1) of mosunetuzumab administered on Day 1 (±1 day) of each dosing cycle, wherein each single dose C2D1-C8D1 is equivalent in amount to the C1D3, wherein the subject is at least 80-years old.

In one aspect, the invention features a method of treating an elderly subject having a previously untreated DLBCL comprising intravenously administering to the subject, as a monotherapy, mosunetuzumab in a dosing regimen comprising seventeen 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 13.5 mg; and (b) the second to seventeenth dosing cycles each comprises a single dose (C2D1-C17D1) of mosunetuzumab administered on Day 1 (±1 day) of each dosing cycle, wherein each single dose C2D1-C17D1 is equivalent in amount to the C1D3, wherein the subject is at least 80-years old.

In one aspect, the invention features a method of treating an elderly subject having a previously untreated DLBCL comprising intravenously administering to the subject, as a monotherapy, mosunetuzumab in a dosing regimen comprising seventeen 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab administered on Day 1 (±1 day) of each dosing cycle, wherein each single dose C2D1-C17D1 is equivalent in amount to the C1D3, wherein the subject is at least 80-years old.

In one aspect, the invention features a method of treating an unfit subject having a previously untreated DLBCL comprising intravenously administering to the subject, as a monotherapy, mosunetuzumab in a dosing regimen comprising eight 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab administered on Day 1 (±1 day) of each dosing cycle, wherein each single dose C2D1-C8D1 is equivalent in amount to the C1D3, wherein the subject is at least 60-years old, and wherein the subject exhibits: (i) an impairment in at least ADL component (Katz et al., 1970); (ii) an impairment in at least one IADL component (Lawton and Brody, 1969); (iii) an impairment in at least one of cardiac function, vascular function, renal function, and/or liver function; and/or (iv) diabetes.

In one aspect, the invention features a method of treating an unfit subject having a previously untreated DLBCL comprising intravenously administering to the subject, as a monotherapy, mosunetuzumab in a dosing regimen comprising eight 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 30 mg; and (b) the second to eighth dosing cycles each comprises a single dose (C2D1-C8D1) of mosunetuzumab administered on Day 1 (±1 day) of each dosing cycle, wherein each single dose C2D1-C8D1 is equivalent in amount to the C1D3, wherein the subject is at least 60-years old, and wherein the subject exhibits: (i) an impairment in at least ADL component; (ii) an impairment in at least one IADL component; (iii) an impairment in at least one of cardiac function, vascular function, renal function, and/or liver function; and/or (iv) diabetes.

In one aspect, the invention features a method of treating an unfit subject having a previously untreated DLBCL comprising intravenously administering to the subject, as a monotherapy, mosunetuzumab in a dosing regimen comprising seventeen 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15

(±1 day), respectively, of the first dosing cycle, wherein the C1D1 is 1 mg, the C1D2 is 2 mg, and the C1D3 is 13.5 mg; and (b) the second to seventeenth dosing cycles each comprises a single dose (C2D1-C17D1) of mosunetuzumab administered on Day 1 (±1 day) of each dosing cycle, wherein each single dose C2D1-C17D1 is equivalent in amount to the C1D3, wherein the subject is at least 60-years old, and wherein the subject exhibits: (i) an impairment in at least ADL component; (ii) an impairment in at least one IADL component; (iii) an impairment in at least one of cardiac function, vascular function, renal function, and/or liver function; and/or (iv) diabetes.

In one aspect, the invention features a method of treating an unfit subject having a previously untreated DLBCL comprising intravenously administering to the subject, as a monotherapy, mosunetuzumab in a dosing regimen comprising seventeen 21-day (e.g., 21±3 days) dosing cycles, wherein: (a) the first dosing cycle comprises a first dose (C1D1), a second dose (C1D2), and a third dose (C1D3) of mosunetuzumab administered on Days 1, 8 (±1 day), and 15 (±1 day), respectively, of the first dosing cycle, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab administered on Day 1 (±1 day) of each dosing cycle, wherein each single dose C2D1-C17D1 is equivalent in amount to the C1D3, wherein the subject is at least 60-years old, and wherein the subject exhibits: (i) an impairment in at least ADL component; (ii) an impairment in at least one IADL component; (iii) an impairment in at least one of cardiac function, vascular function, renal function, and/or liver function; and/or (iv) diabetes.

In some embodiments, the subject is human.

In some instances, treating a population of subjects having previously untreated (1 L) B cell proliferative disorder using a dosing regimen provided by the methods of the present invention results in the population of subjects having an overall response rate (ORR) of greater than 56% (e.g., greater than 57%, 58%, 59%, 60%, 61%, 62%, 63%, 64%, 65%, 66%, 67%, 68%, 69%, 70%, 71%, 72%, 73%, 74%, 75%, 76%, 77%, 78%, 80%, 85%, 90%, 95%, 97%, 98%, 99%, or 100%; e.g., between 56%-100%, 56%-90%, 56%-80%, 56%-70%, 56%-68%, 56%-67%, 56%-66%, 56%-65%, 56%-64%, 56%-63%, 56%-62%, 56%-61%, 56%-60%, 56%-59%, 56%-58%, 56%-57%, 57%-61%, 58%-61%, 59%-61%, 60%-61%, 57%-60%, 58%-59%, 57%-59%, 61%-65%, 61%-70%, 61%-75%, 61%-80%, 61%-90%, 70%-90%, 65%-80%, 60%-90%, 75%-85%, 85%-100%, 56%-66%, 56%-71%, 59%-63%, or 60%-65%; e.g., 56%, 57%, 58%, 59%, 60%, 61%, 62%, 63%, 64%, 65%, 66%, 67%, 68%, 69%, 70%, 75%, 80%, 85%, 90%, 95%, 97%, 98%, 99%, or 100%). In some instances, the ORR is greater than 56%. In some instances, the ORR is greater than 61%. In some instances, the ORR is 61%.

In some instances, treating a population of subjects having previously untreated (1 L) diffuse large B-cell lymphoma using a dosing regimen provided by the methods of the present invention results in the population of subjects having an overall response rate (ORR) of greater than 56% (e.g., greater than 57%, 58%, 59%, 60%, 61%, 62%, 63%, 64%, 65%, 66%, 67%, 68%, 69%, 70%, 71%, 72%, 73%, 74%, 75%, 76%, 77%, 78%, 80%, 85%, 90%, 95%, 97%, 98%, 99%, or 100%; e.g., between 56%-100%, 56%-90%, 56%-80%, 56%-70%, 56%-68%, 56%-67%, 56%-66%, 56%-65%, 56%-64%, 56%-63%, 56%-62%, 56%-61%, 56%-60%, 56%-59%, 56%-58%, 56%-57%, 57%-61%, 58%-61%, 59%-61%, 60%-61%, 57%-60%, 58%-59%, 57%-59%, 61%-65%, 61%-70%, 61%-75%, 61%-80%, 61%-90%, 70%-90%, 65%-80%, 60%-90%, 75%-85%, 85%-100%, 56%-66%, 56%-71%, 59%-63%, or 60%-65%; e.g., 56%, 57%, 58%, 59%, 60%, 61%, 62%, 63%, 64%, 65%, 66%, 67%, 68%, 69%, 70%, 75%, 80%, 85%, 90%, 95%, 97%, 98%, 99%, or 100%). In some instances, the ORR is greater than 56%. In some instances, the ORR is greater than 61%. In some instances, the ORR is 61%.

In some instances, treating a population of subjects having previously untreated (1 L) high grade B-cell lymphoma using a dosing regimen provided by the methods of the present invention results in the population of subjects having an overall response rate (ORR) of greater than 56% (e.g., greater than 57%, 58%, 59%, 60%, 61%, 62%, 63%, 64%, 65%, 66%, 67%, 68%, 69%, 70%, 71%, 72%, 73%, 74%, 75%, 76%, 77%, 78%, 80%, 85%, 90%, 95%, 97%, 98%, 99%, or 100%; e.g., between 56%-100%, 56%-90%, 56%-80%, 56%-70%, 56%-68%, 56%-67%, 56%-66%, 56%-65%, 56%-64%, 56%-63%, 56%-62%, 56%-61%, 56%-60%, 56%-59%, 56%-58%, 56%-57%, 57%-61%, 58%-61%, 59%-61%, 60%-61%, 57%-60%, 58%-59%, 57%-59%, 61%-65%, 61%-70%, 61%-75%, 61%-80%, 61%-90%, 70%-90%, 65%-80%, 60%-90%, 75%-85%, 85%-100%, 56%-66%, 56%-71%, 59%-63%, or 60%-65%; e.g., 56%, 57%, 58%, 59%, 60%, 61%, 62%, 63%, 64%, 65%, 66%, 67%, 68%, 69%, 70%, 75%, 80%, 85%, 90%, 95%, 97%, 98%, 99%, or 100%). In some instances, the ORR is greater than 56%. In some instances, the ORR is greater than 61%. In some instances, the ORR is 61%.

In some instances, treating a population of subjects having previously untreated (1 L) B cell proliferative disorder using a dosing regimen provided by the methods of the present invention results in the population of subjects having a complete response (CR) rate of greater than 38% (e.g., greater than 39%, 40%, 41%, 42%, 43%, 44%, 45%, 46%, 47%, 48%, 49%, 50%, 51%, 52%, 53%, 54%, 55%, 56%, 57%, 58%, 59%, 60%, 65%, 70%, 75%, 80%, 85%, 90%, 95%, 97%, 98%, 99%, or 100%; e.g., between 38%-100%, 38%-90%, 38%-80%, 38%-70%, 38%-65%, 38%-60%, 38%-55%, 38%-50%, 38%-48%, 38%-47%, 38%-46%, 38%-45%, 38%-44%, 38%-43%, 38%-42%, 38%-41%, 38%-40%, 38%-39%, 39%-43%, 40%-43%, 41%-43%, 42%-43%, 39%-42%, 43%-45%, 43%-48%, 43%-50%, 43%-55%, 43%-60%, 43%-70%, 43%-80%, 43%-90%, 43%-100%, 50%-90%, 60%-80%, 55%-70%, 85%-100%, 39%-50%, 41%-50%, 39%-55%, or 41%-55%; e.g., 38%, 39%, 40%, 41%, 42%, 43%, 44%, 45%, 46%, 47%, 48%, 49%, 50%, 52%, 54%, 55%, 57%, 60%, 65%, 70%, 75%, 80%, 85%, 90%, 95%, 97%, 98%, 99%, or 100%). In some instances, the CR rate is greater than 38%. In some instances, the CR rate is greater than 43%. In some instances, the CR rate is 43%.

In some instances, treating a population of subjects having previously untreated (1 L) diffuse large B-cell lymphoma (DLBCL) using a dosing regimen provided by the methods of the present invention results in the population of subjects having a complete response (CR) rate of greater than 38% (e.g., greater than 39%, 40%, 41%, 42%, 43%, 44%, 45%, 46%, 47%, 48%, 49%, 50%, 51%, 52%, 53%, 54%, 55%, 56%, 57%, 58%, 59%, 60%, 65%, 70%, 75%, 80%, 85%, 90%, 95%, 97%, 98%, 99%, or 100%; e.g., between 38%-100%, 38%-90%, 38%-80%, 38%-70%, 38%-65%, 38%-60%, 38%-55%, 38%-50%, 38%-48%, 38%-47%, 38%-46%, 38%-45%, 38%-44%, 38%-43%, 38%-42%, 38%-41%, 38%-40%, 38%-39%, 39%-43%, 40%-43%, 41%-43%, 42%-43%, 39%-42%, 43%-45%, 43%-48%, 43%-50%, 43%-55%, 43%-60%, 43%-70%, 43%-

80%, 43%-90%, 43%-100%, 50%-90%, 60%-80%, 55%-70%, 85%-100%, 39%-50%, 41%-50%, 39%-55%, or 41%-55%; e.g., 38%, 39%, 40%, 41%, 42%, 43%, 44%, 45%, 46%, 47%, 48%, 49%, 50%, 52%, 54%, 55%, 57%, 60%, 65%, 70%, 75%, 80%, 85%, 90%, 95%, 97%, 98%, 99%, or 100%). In some instances, the CR rate is greater than 38%. In some instances, the CR rate is greater than 43%. In some instances, the CR rate is 43%.

In some instances, treating a population of subjects having previously untreated (1 L) high grade B-cell lymphoma using a dosing regimen provided by the methods of the present invention results in the population of subjects having a complete response (CR) rate of greater than 38% (e.g., greater than 39%, 40%, 41%, 42%, 43%, 44%, 45%, 46%, 47%, 48%, 49%, 50%, 51%, 52%, 53%, 54%, 55%, 56%, 57%, 58%, 59%, 60%, 65%, 70%, 75%, 80%, 85%, 90%, 95%, 97%, 98%, 99%, or 100%; e.g., between 38%-100%, 38%-90%, 38%-80%, 38%-70%, 38%-65%, 38%-60%, 38%-55%, 38%-50%, 38%-48%, 38%-47%, 38%-46%, 38%-45%, 38%-44%, 38%-43%, 38%-42%, 38%-41%, 38%-40%, 38%-39%, 39%-43%, 40%-43%, 41%-43%, 42%-43%, 39%-42%, 43%-45%, 43%-48%, 43%-50%, 43%-55%, 43%-60%, 43%-70%, 43%-80%, 43%-90%, 43%-100%, 50%-90%, 60%-80%, 55%-70%, 85%-100%, 39%-50%, 41%-50%, 39%-55%, or 41%-55%; e.g., 38%, 39%, 40%, 41%, 42%, 43%, 44%, 45%, 46%, 47%, 48%, 49%, 50%, 52%, 54%, 55%, 57%, 60%, 65%, 70%, 75%, 80%, 85%, 90%, 95%, 97%, 98%, 99%, or 100%). In some instances, the CR rate is greater than 38%. In some instances, the CR rate is greater than 43%. In some instances, the CR rate is 43%.

In some instances, greater than 42% (e.g., greater than 43%, 44%, 45%, 46%, 47%, 48%, 49%, 50%, 51%, 52%, 53%, 54%, 55%, 56%, 57%, 58%, 59%, 60%, 65%, 70%, 75%, 80%, 85%, 90%, 95%, 97%, 98%, 99%, or 100%; e.g., between 42%-100%, 45%-100%, 50%-100%, 55%-100%, 60%-100%, 65%-100%, 70%-100%, 80%-100%, 90%-100%, 42%-47%, 42%-50%, 42%-55%, 42%-60%, 42%-65%, 42%-70%, 42%-80%, 42%-90%, 47%-55%, 47%-60%, 47%-70%, 45%-55%, or 45%-60%; e.g., 43%, 44%, 45%, 46%, 47%, 48%, 49%, 50%, 51%, 52%, 53%, 54%, 55%, 56%, 57%, 58%, 59%, 60%, 65%, 70%, 75%, 80%, 85%, 90%, 95%, 97%, 98%, 99%, or 100%) of subjects of the population of subjects described herein who exhibit a complete response maintained complete remission for 12 months. In some instances, greater than 42% of subjects of the population of subjects described herein who exhibit a complete response maintained complete remission for 12 months. In some instances, greater than 47% of subjects of the population of subjects described herein who exhibit a complete response maintained complete remission for 12 months. In some instances, 47% of subjects of the population of subjects described herein who exhibit a complete response maintained complete remission for 12 months.

In any of the methods described herein, the population of subjects may comprise elderly subjects, unfit subjects, or subjects unsuitable for treatment with standard chemotherapy or chemoimmunotherapy (CIT).

In some instances, the population of subjects comprises elderly subjects. In some instances, elderly subjects comprise subjects older than 60-years of age. In some instances, the population of subjects comprise elderly subjects. In some instances, elderly subjects comprise subjects older than 65-years of age. In some instances, elderly subjects comprise subjects older than 80-years of age.

In some instances, the population of subjects comprises unfit subjects. In some instances, unfit subjects comprise subjects older than 60-years of age. In some instances, unfit subjects comprise subjects between 60-years and 79-years of age. In some instances, unfit subjects exhibit an impairment in at least one activity of daily living (ADL) component (Katz et al., 1970); an impairment in at least one instrumental activity of daily living (IADL) component (Lawton and Brody, 1969); an impairment in at least one of cardiac function, vascular function, renal function, and/or liver function; and/or (iv) diabetes. In some instances, the unfit subjects exhibit an impairment in at least one ADL component (Katz et al., 1970). In some instances, the unfit subjects exhibit an impairment in at least one IADL component (Lawton and Brody, 1969). In some instances, the unfit subjects exhibit an impairment in cardiac function comprisapproach is not always successful, especially in the case of late intervention. The CRS grading criteria used by the methods described herein are published by the American Society for Transplantation and Cellular Therapy® (ASTCT®) to define mild, moderate, severe, or life-threatening CRS and harmonize reporting across clinical trials to allow rapid recognition and treatment of CRS (Lee et al. *Biology of Blood and Marrow Transplantation.* 25(4): 625-638, 2019). The ASTCT® criteria is intended to be objective, easy to apply, and more accurately categorize the severity of CRS. This CRS grading system is shown below in Table 1.

TABLE 1

| CRS Grading System | | | | |
|---|---|---|---|---|
| CRS Parameter | Grade 1 | Grade 2 | Grade 3 | Grade 4 |
| Fever | Temperature ≥38° C. | Temperature ≥38° C. | Temperature ≥38° C. with | Temperature ≥38° C. |
| Hypotension | None | Not requiring vasopressors | Requiring a vasopressor with or without vasopressin and/or | Requiring multiple vasopressors (excluding vasopressin) |
| Hypoxia | None | Requiring low-glow nasal cannula or blow-by | Requiring high-flow nasal cannula, facemask, nonrebreather mask or Venturi mask | Requiring positive pressure (e.g., CPAP, BiPAP, intubation and mechanical ventilation) |

ASTCT ® = American Society for Transplantation and Cellular Therapy ®;
BiPAP = bilevel positive airway pressure;
CPAP = continuous positive airway pressure;
CRS = cytokine release syndrome;
CTCAE = Common Terminology Criteria for Adverse Events.

ing heart arrhythmia, congestive heart failure (CHF), myocardial infarction, and/or cardiac-related symptoms of hypothyroidism. In some instances, the unfit subjects exhibit an impairment in vascular function comprising anemia, cerebrovascular accident (CVA), cerebrovascular disease (CVD), chronic obstructive pulmonary disease not otherwise specified (COPD: NOS), hyperlipidemia, peripheral vascular disease, stroke, and/or ischemic attack (TIA). In some instances, the unfit subjects exhibit an impairment in renal function comprising acute kidney disease and/or chronic kidney disease. In some instances, the unfit subjects exhibit an impairment in in liver function. In some instances, the unfit subjects exhibit diabetes, comprising type 2 diabetes, diabetes with end organ damage (EOD), and/or diabetes without EOD.

In some instances, the population of subjects comprises subjects who are unsuitable for treatment with R-CHOP therapy. In some instances, the R-CHOP therapy comprises rituximab, cyclophosphamide, doxorubicin, vincristine, and prednisone, and further wherein the rituximab is administered to the subject at a dose of 375 mg/m² every three weeks.

In some instances, the subjects comprising the population of subjects are human.

Any of the methods described herein may involve monitoring a subject for cytokine release syndrome (CRS), e.g., a CRS event following commencement of any of the methods described above. Current clinical management focuses on treating the individual signs and symptoms, providing supportive care, and attempting to dampen the inflammatory response using a high dose of corticosteroids. However, this Fever is defined as a temperature ≥38° C. not attributable to any other cause. In subjects who have CRS then receive antipyretic or anticytokine therapy such as tocilizumab or steroids, fever is no longer required to grade subsequent CRS severity. In this case, CRS grading is determined by hypotension and/or hypoxia.

CRS grade is determined by the more severe event, hypotension or hypoxia not attributable to any other cause. For example, a subject with temperature of 39.5° C., hypotension requiring 1 vasopressor, and hypoxia requiring low-flow nasal cannula is classified as Grade 3 CRS.

Low-flow nasal cannula is defined as oxygen delivered at ≤6 L/minute. Low flow also includes blow-by oxygen delivery, sometimes used in pediatrics. High-flow nasal cannula is defined as oxygen delivered at >6 L/minute.

CRS is associated with elevations in a wide array of cytokines, including marked elevations in IFN-γ, IL-6, and TNF-α levels. Emerging evidence implicates IL-6, in particular, as a central mediator in CRS. IL-6 is a proinflammatory, multi-functional cytokine produced by a variety of cell types, which has been shown to be involved in a diverse array of physiological processes, including T cell activation. Regardless of the inciting agent, CRS is associated with high IL-6 levels (Nagorsen et al. *Cytokine.* 25(1): 31-5, 2004; Lee et al. *Blood.* 124(2): 188-95, 2014; Doesegger et al. *Clin. Transl. Immunology.* 4(7): e39, 2015), and IL-6 correlates with the severity of CRS, with subjects who experience a Grade 4 or 5 CRS event having much higher IL-6 levels compared to subjects who do not experience CRS or experience milder CRS (Grades 0-3) (Chen et al. *J. Immunol. Methods.* 434:1-8, 2016).

Therefore, blocking the inflammatory action of IL-6 using an agent that inhibits IL-6-mediated signaling to manage CRS observed in subjects during the double-step fractionated, dose-escalation dosing regimen is an alternative to steroid treatment that would not be expected to negatively impact T cell function or diminish the efficacy or clinical benefit of anti-CD20/anti-CD3 bispecific antibody therapy in the treatment of CD20-positive cell proliferative disorders (e.g., a B cell proliferative disorders).

Tocilizumab (ACTEMRA®/RoACTEMRA®) is a recombinant, humanized, anti-human monoclonal antibody directed against soluble and membrane-bound IL-6R, which inhibits IL-6-mediated signaling (see, e.g., WO 1992/019579, which is incorporated herein by reference in its entirety).

If the subject has a cytokine release syndrome (CRS) event following administration of the bispecific antibody, the method may further involve administering to the subject an effective amount of an interleukin-6 receptor (IL-6R) antagonist (e.g., an anti-IL-6R antibody, e.g., tocilizumab (ACTEMRA®/RoACTEMRA®)) to manage the event. In some instances, tocilizumab is administered intravenously to the subject as a single dose of about 8 mg/kg. In some instances, each dose of tocilizumab does not exceed 800 mg/dose. Other anti-IL-6R antibodies that could be used instead of, or in combination with, tocilizumab include sarilumab, vobarilizumab (ALX-0061), satralizumab (SA-237), and variants thereof.

If the subject has a CRS event that does not resolve or worsens within 24 hours of administering the IL-6R antagonist to treat the symptoms of the CRS event, and the method may further comprise administering to the subject one or more additional doses of the IL-6R antagonist (e.g., an anti-IL-6R antibody, e.g., tocilizumab) to manage the CRS event. The subject may be administered a corticosteroid, such as methylprednisolone or dexamethasone if CRS event is not managed through administration of the IL-6R antagonist.

Management of the CRS events may be tailored based on the Stage of the CRS and the presence of comorbidities. For example, if the subject has a Grade 2 cytokine release syndrome (CRS) event in the absence of comorbidities or in the presence of minimal comorbidities following administration of the bispecific antibody, the method may further include treating the symptoms of the Grade 2 CRS event while suspending treatment with the bispecific antibody. If the Grade 2 CRS event then resolves to a Grade≤1 CRS event for at least three consecutive days, the method may further include resuming treatment with the bispecific antibody without altering the dose. On the other hand, if the Grade 2 CRS event does not resolve or worsens to a Grade≥3 CRS event within 24 hours of treating the symptoms of the Grade 2 CRS event, the method may further involve administering to the subject an effective amount of an interleukin-6 receptor (IL-6R) antagonist (e.g., an anti-IL-6R antibody, e.g., tocilizumab (ACTEMRA® D/Ro-ACTEMRA®)) to manage the Grade 2 or Grade≥3 CRS event. In some instances, tocilizumab is administered intravenously to the subject as a single dose of about 8 mg/kg. In some instances, each dose of tocilizumab does not exceed 800 mg/dose. Other anti-IL-6R antibodies that could be used instead of, or in combination with, tocilizumab include sarilumab, vobarilizumab (ALX-0061), satralizumab (SA-237), and variants thereof.

If the subject has a grade 2, 3, or 4 CRS event in the presence of extensive comorbidities following administration of the bispecific antibody, the method may further include methods understood in the art to mitigate the CRS event, such as administering to the subject a first dose of an IL-6R antagonist (e.g., an anti-IL-6R antibody, e.g., tocilizumab (ACTEMRA®/RoACTEMRA®)) to manage the CRS event while suspending treatment with the bispecific antibody. Other anti-IL-6R antibodies that could be used instead of, or in combination with, tocilizumab include sarilumab, vobarilizumab (ALX-0061), satralizumab (SA-237), and variants thereof. In some instances, the method further includes administering to the subject an effective amount of a corticosteroid, such as methylprednisolone or dexamethasone.

In some instances, treating a population of subjects having previously untreated (1 L) diffuse large B-cell lymphoma using a dosing regimen provided by the methods of the present invention results in the population of subjects having a rate of cytokine release syndrome having a grade of 3 or higher (as defined by the American Society for Transplantation and Cellular Therapy®, 2018; ASTCT®) less than 5% (e.g., less than 4%, less than 3%, less than 2%, or less than 1%; e.g., 4%, 3%, 2%, 1%, or 0%). In some instances, the rate of cytokine release syndrome having a grade of 3 or higher (as defined by the ASTCT®) is less than 3%. In some instances, the rate of cytokine release syndrome having a grade of 3 or higher (as defined by the ASTCT®) is less than 1%. In some instances, the rate of cytokine release syndrome having a grade of 3 or higher (as defined by the ASTCT®) is 5%. In some instances, the rate of cytokine release syndrome having a grade of 3 or higher (as defined by the ASTCT®) is 3%. In some instances, the rate of cytokine release syndrome having a grade of 3 or higher (as defined by the ASTCT®) is 1%. In some instances, the rate of cytokine release syndrome having a grade of 3 or higher (as defined by the ASTCT®) is 0%.

B. Bispecific Antibodies that Bind to CD20 and CD3

The invention provides bispecific antibodies that bind to CD20 and CD3 (i.e., anti-CD20/anti-CD3 antibodies) useful for treating a previously untreated (1 L) B cell proliferative disorder (e.g., 1 L non-Hodgkin's lymphoma (NHL) (e.g., 1 L diffuse-large B cell lymphoma (DLBCL)) or 1 L high grade B-cell lymphoma).

In some instances, the invention provides a bispecific antibody that includes an anti-CD20 arm having a first binding domain comprising at least one, two, three, four, five, or six hypervariable regions (HVRs) selected from (a) an HVR-H1 comprising the amino acid sequence of GYTFTSYNMH (SEQ ID NO: 1); (b) an HVR-H2 comprising the amino acid sequence of AIYPGNGDTSYN-QKFKG (SEQ ID NO: 2); (c) an HVR-H3 comprising the amino acid sequence of VVYYSNSYWYFDV (SEQ ID NO: 3); (d) an HVR-L1 comprising the amino acid sequence of RASSSVSYMH (SEQ ID NO: 4); (e) an HVR-L2 comprising the amino acid sequence of APSNLAS (SEQ ID NO: 5); and (f) an HVR-L3 comprising the amino acid sequence of QQWSFNPPT (SEQ ID NO: 6). In some instances, the anti-CD20/anti-CD3 bispecific antibody comprises at least one (e.g., 1, 2, 3, or 4) of heavy chain framework regions FR-H1, FR-H2, FR-H3, and FR-H4 comprising the sequences of SEQ ID NOs: 17-20, respectively, and/or at least one (e.g., 1, 2, 3, or 4) of the light chain framework regions FR-L1, FR-L2, FR-L3, and FR-L4 comprising the sequences of SEQ ID NOs: 21-24, respectively. In some instances, the bispecific antibody comprises an anti-CD20 arm comprising a first binding domain comprising (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 7; (b) a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 8; or (c) a VH domain as in (a) and a VL domain as in (b). Accordingly, in some instances, the first binding domain comprises a VH domain comprising an amino acid sequence of SEQ ID NO: 7 and a VL domain comprising an amino acid sequence of SEQ ID NO: 8.

In some instances, the invention provides a bispecific antibody that includes an anti-CD3 arm having a second binding domain comprising at least one, two, three, four, five, or six HVRs selected from (a) an HVR-H1 comprising the amino acid sequence of NYYIH (SEQ ID NO: 9); (b) an HVR-H2 comprising the amino acid sequence of WIYPGDGNTKYNEKFKG (SEQ ID NO: 10); (c) an HVR-H3 comprising the amino acid sequence of DSYS-NYYFDY (SEQ ID NO: 11); (d) an HVR-L1 comprising the amino acid sequence of KSSQSLLNSRTRKNYLA (SEQ ID NO: 12); (e) an HVR-L2 comprising the amino acid sequence of WASTRES (SEQ ID NO: 13); and (f) an HVR-L3 comprising the amino acid sequence of TQSFILRT (SEQ ID NO: 14). In some instances, the anti-CD20/anti-CD3 bispecific antibody comprises at least one (e.g., 1, 2, 3, or 4) of heavy chain framework regions FR-H1, FR-H2, FR-H3, and FR-H4 comprising the sequences of SEQ ID NOs: 25-28, respectively, and/or at least one (e.g., 1, 2, 3, or 4) of the light chain framework regions FR-L1, FR-L2, FR-L3, and FR-L4 comprising the sequences of SEQ ID NOs: 29-32, respectively. In some instances, the bispecific antibody comprises an anti-CD3 arm comprising a second binding domain comprising (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 15; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 16; or (c) a VH domain as in (a) and a VL domain as in (b). Accordingly, in some instances, the second binding domain comprises a VH domain comprising an amino acid sequence of SEQ ID NO: 15 and a VL domain comprising an amino acid sequence of SEQ ID NO: 16.

In some instances, the invention provides a bispecific antibody that includes (1) an anti-CD20 arm having a first binding domain comprising at least one, two, three, four, five, or six HVRs selected from (a) an HVR-H1 comprising the amino acid sequence of GYTFTSYNMH (SEQ ID NO: 1); (b) an HVR-H2 comprising the amino acid sequence of AIYPGNGDTSYNQKFKG (SEQ ID NO: 2); (c) an HVR-H3 comprising the amino acid sequence of VVYYSN-SYWYFDV (SEQ ID NO: 3); (d) an HVR-L1 comprising the amino acid sequence of RASSSVSYMH (SEQ ID NO: 4); (e) an HVR-L2 comprising the amino acid sequence of APSNLAS (SEQ ID NO: 5); and (f) an HVR-L3 comprising the amino acid sequence of QQWSFNPPT (SEQ ID NO: 6); and (2) an anti-CD3 arm having a second binding domain comprising at least one, two, three, four, five, or six HVRs selected from (a) an HVR-H1 comprising the amino acid sequence of NYYIH (SEQ ID NO: 9); (b) an HVR-H2 comprising the amino acid sequence of WIYPGDGNT-KYNEKFKG (SEQ ID NO: 10); (c) an HVR-H3 comprising the amino acid sequence of DSYSNYYFDY (SEQ ID NO: 11); (d) an HVR-L1 comprising the amino acid sequence of KSSQSLLNSRTRKNYLA (SEQ ID NO: 12); (e) an HVR- L2 comprising the amino acid sequence of WASTRES (SEQ ID NO: 13); and (f) an HVR-L3 comprising the amino acid sequence of TQSFILRT (SEQ ID NO: 14). In some instances, the anti-CD20/anti-CD3 bispecific antibody comprises (1) at least one (e.g., 1, 2, 3, or 4) of heavy chain framework regions FR-H1, FR-H2, FR-H3, and FR-H4 comprising the sequences of SEQ ID NOs: 17-20, respectively, and/or at least one (e.g., 1, 2, 3, or 4) of the light chain framework regions FR-L1, FR-L2, FR-L3, and FR-L4 comprising the sequences of SEQ ID NOs: 21-24, respectively, and (2) at least one (e.g., 1, 2, 3, or 4) of heavy chain framework regions FR-H1, FR-H2, FR-H3, and FR-H4 comprising the sequences of SEQ ID NOs: 25-28, respectively, and/or at least one (e.g., 1, 2, 3, or 4) of the light chain framework regions FR-L1, FR-L2, FR-L3, and FR-L4 comprising the sequences of SEQ ID NOs: 29-32, respectively. In some instances, the anti-CD20/anti-CD3 bispecific antibody comprises (1) an anti-CD20 arm comprising a first binding domain comprising (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 7; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 8; or (c) a VH domain as in (a) and a VL domain as in (b), and (2) an anti-CD3 arm comprising a second binding domain comprising (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 15; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 16; or (c) a VH domain as in (a) and a VL domain as in (b). In some instances, the anti-CD20/anti-CD3 bispecific antibody comprises (1) a first binding domain comprising a VH domain comprising an amino acid sequence of SEQ ID NO: 7 and a VL domain comprising an amino acid sequence of SEQ ID NO: 8 and (2) a second binding domain comprising a VH domain comprising an amino acid sequence of SEQ ID NO: 15 and a VL domain comprising an amino acid sequence of SEQ ID NO: 16.

In some instances, the anti-CD20/anti-CD3 bispecific antibody is mosunetuzumab, having the International Non-proprietary Names for Pharmaceutical Substances (INN) List 117 (WHO Drug Information, Vol. 31, No. 2, 2017, p. 303), or CAS Registry® No. 1905409-39-3, and having (1) an anti-CD20 arm comprising the heavy chain and light chain sequences of SEQ ID NOs: 33 and 34, respectively; and (2) an anti-CD3 arm comprising the heavy chain and light chain sequences of SEQ ID NOs: 35 and 36, respectively. In some instances, the anti-CD20/anti-CD3 bispecific antibody comprises (1) an anti-CD20 arm comprising a first binding domain comprising (a) a heavy chain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 33; (b) a light chain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 34; or (c) a heavy chain as in (a) and a light chain as in (b), and (2) an anti-CD3 arm comprising a second binding domain comprising (a) a heavy chain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 35; (b) a light chain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 36; or (c) a heavy chain as in (a) and a light chain as in (b). In some instances, the anti-CD20/anti-CD3 bispecific antibody comprises (1) an anti-CD20 arm comprising a first binding domain comprising a heavy chain comprising an amino acid sequence of SEQ ID NO: 33 and a light chain comprising an amino acid sequence of SEQ ID NO: 34 and (2) an anti-CD3 arm comprising a second binding domain comprising a heavy chain comprising an amino acid sequence of SEQ ID NO: 35 and a light chain comprising an amino acid sequence of SEQ ID NO: 36.

Amino acid sequences of mosunetuzumab are summarized in Table 2 below.

TABLE 2

| Sequence IDs for Mosunetuzumab | | | |
|---|---|---|---|
| CD3 Arm | | CD20 Arm | |
| SEQ ID NO: | Description | SEQ ID NO: | Description |
| 9 | CD3 HVR-H1 | 1 | CD20 HVR-H1 |
| 10 | CD3 HVR-H2 | 2 | CD20 HVR-H2 |
| 11 | CD3 HVR-H3 | 3 | CD20 HVR-H3 |
| 12 | CD3 HVR-L1 | 4 | CD20 HVR-L1 |
| 13 | CD3 HVR-L2 | 5 | CD20 HVR-L2 |
| 14 | CD3 HVR-L3 | 6 | CD20 HVR-L3 |
| 15 | CD3 VH | 7 | CD20 VH |
| 16 | CD3 VL | 8 | CD20 VL |
| 35 | CD3 heavy chain | 33 | CD20 heavy chain |
| 36 | CD3 light chain | 34 | CD20 light chain |

The anti-CD20/anti-CD3 bispecific antibody may be produced using recombinant methods and compositions, for example, as described in U.S. Pat. No. 4,816,567.

In some instances, the anti-CD20/anti-CD3 bispecific antibody according to any of the above embodiments described above may incorporate any of the features, singly or in combination, as described in Section C below.

C. Antibody Formats and Properties

The methods described herein may further include any of the antibodies described above, wherein the antibody comprises any of the features, singly or in combination, as described below.

1. Antibody Affinity

In certain instances, an anti-CD20/anti-CD3 bispecific antibody has a dissociation constant ($K_D$) of $\leq 1$ µM, $\leq 100$ nM, $\leq 10$ nM, $<1$ nM, $\leq 0.1$ nM, $\leq 0.01$ nM, or $\leq 0.001$ nM (e.g., $10^{-8}$ M or less, e.g., from $10^{-8}$ M to $10^{-13}$ M, e.g., from $10^{-9}$ M to $10^{-13}$ M).

In one instance, $K_D$ is measured by a radiolabeled antigen binding assay (RIA). In one instance, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another instance, $K_D$ is measured using a BIACORE® surface plasmon resonance assay. For example, an assay using a BIACORE®-2000 or a BIACORE®-3000 (BIACORE®, Inc., Piscataway, NJ) is performed at 25° C. with immobilized antigen CM5 chips at ~10 response units (RU). In one instance, carboxymethylated dextran biosensor chips (CM5, BIACORE®, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20®) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$. See, for example, Chen et al., *J. Mol. Biol.* 293:865-881 (1999). If the on-rate exceeds $10^6$ $M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain instances, an anti-CD20/anti-CD3 bispecific antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al. *Nat. Med.* 9:129-134 (2003); and Hollinger et al. *Proc. Nat. Acad. Sci. USA* 90: 6444-6448 (1993). Triabodies and tetrabodies are also described in Hudson et al. *Nat. Med.* 9:129-134 (2003).

Single-domain antibodies are antibody fragments comprising all or a portion of the heavy chain variable domain or all or a portion of the light chain variable domain of an antibody. In certain instances, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In certain instances, an anti-CD20/anti-CD3 bispecific antibody provided herein is a chimeric antibody. Certain chimeric antibodies are described, e.g., in U.S. Pat. No. 4,816,567; and Morrison et al. *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain instances, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some instances, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Natl Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285

(1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain instances, an anti-CD20/anti-CD3 bispecific antibody is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Anti-CD20/anti-CD3 bispecific antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, NJ, 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, NJ, 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and U.S. Patent Publication Nos. 2005/0079574, 2005/0119455, 2005/0266000, 2007/0117126, 2007/0160598, 2007/0237764, 2007/0292936, and 2009/0002360.

Anti-CD20/anti-CD3 bispecific antibodies or antibody fragments isolated from human antibody libraries are considered human antibodies or human antibody fragments herein.

6. Antibody Variants

In certain instances, amino acid sequence variants of anti-CD20/anti-CD3 bispecific antibodies of the invention are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

a. Substitution, Insertion, and Deletion Variants

In certain instances, anti-CD20/anti-CD3 bispecific antibody variants having one or more amino acid substitutions are provided. Sites of interest for substitutional mutagenesis include the HVRs and FRs. Conservative substitutions are shown in Table 3 under the heading of "preferred substitutions." More substantial changes are provided in Table 3 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved ADCC or CDC.

TABLE 3

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, lie;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some instances of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain instances, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain instances of the variant VH and VL sequences provided above, each HVR either is unaltered, or includes no more than one, two, or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b. Glycosylation Variants

In certain instances, anti-CD20/anti-CD3 bispecific antibodies of the invention can be altered to increase or decrease the extent to which the antibody is glycosylated. Addition or deletion of glycosylation sites to anti-CD20/anti-CD3 bispecific antibodies of the invention may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some instances, modifications of the oligosaccharide in an antibody of the invention are made in order to create antibody variants with certain improved properties.

In one instance, anti-CD20/anti-CD3 bispecific antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., U.S. Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); U.S. Patent Application No. US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

In view of the above, in some instances, the methods of the invention involve administering to the subject in the context of a fractionated, dose-escalation dosing regimen an anti-CD20/anti-CD3 bispecific antibody variant that comprises an aglycosylation site mutation. In some instances, the aglycosylation site mutation reduces effector function of the antibody. In some instances, the aglycosylation site mutation is a substitution mutation. In some instances, the antibody comprises a substitution mutation in the Fc region that reduces effector function. In some instances, the substitution mutation is at amino acid residue N297, L234, L235, and/or D265 (EU numbering). In some instances, the substitution mutation is selected from the group consisting of N297G, N297A, L234A, L235A, D265A, and P329G (EU numbering). In some instances, the substitution mutation is at amino acid residue N297 (EU numbering). In a preferred instance, the substitution mutation is N297A (EU numbering). In some embodiments the anti-CD20 arm of the anti-CD20/anti-CD3 bispecific antibody further comprises T366W and N297G substitution mutations (EU numbering). In some embodiments, the anti-CD3 arm of the anti-CD20/anti-CD3 bispecific antibody further comprises T366S, L368A, Y407V, and N297G substitution mutations (EU numbering). In some embodiments, (a) the anti-CD20 arm further comprises T366W and N297G substitution mutations and (b) the anti-CD3 arm further comprises T366S, L368A, Y407V, and N297G substitution mutations (EU numbering).

Anti-CD20/anti-CD3 bispecific antibody variants are further provided with bisected oligosaccharides, for example, in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c. Fc Region Variants

In certain instances, one or more amino acid modifications are introduced into the Fc region of an anti-CD20/anti-CD3 bispecific antibody of the invention, thereby generating an Fc region variant (see e.g., US 2012/0251531). The Fc region variant may comprise a human Fc region sequence (e.g., a human IgG1, IgG2, IgG3 or IgG4 Fc region) comprising an amino acid modification (e.g., a substitution) at one or more amino acid positions.

In certain instances, the invention contemplates an anti-CD20/anti-CD3 bispecific antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII, and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g., Hellstrom, I. et al. *Proc. Natl Acad. Sci. USA* 83:7059-7063 (1986)) and Hellstrom, I. et al., *Proc. Natl Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CYTOTOX 96® non-radioactive cytotoxicity assay (PROMEGA®, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Natl Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al. *J. Immunol. Methods* 202:163 (1996); Cragg, M. S. et al. *Blood.* 101:1045-1052 (2003); and Cragg, M. S. and M. J. Glennie *Blood.* 103:2738-2743 (2004)). FcRn binding and in vivo clearance/half-life determinations can also be performed using methods known in the art (see, e.g., Petkova, S. B. et al. *Int'l. Immunol.* 18(12):1759-1769 (2006)).

Antibodies with reduced effector function include those with substitution of one or more of Fc region residues 238, 265, 269, 270, 297, 327 and 329 (U.S. Pat. Nos. 6,737,056 and 8,219,149). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. Nos. 7,332,581 and 8,219,149).

In certain instances, the proline at position 329 of a wild-type human Fc region in the antibody is substituted with glycine or arginine or an amino acid residue large enough to destroy the proline sandwich within the Fc/Fc.gamma receptor interface that is formed between the proline 329 of the Fc and tryptophan residues Trp 87 and Trp 110 of FcgRIII (Sondermann et al.: *Nature* 406, 267-273 (20 Jul. 2000)). In certain instances, the antibody comprises at least one further amino acid substitution. In one instance, the further amino acid substitution is S228P, E233P, L234A, L235A, L235E, N297A, N297D, or P331S, and still in another instance the at least one further amino acid substitution is L234A and L235A of the human IgG1 Fc region or S228P and L235E of the human IgG4 Fc region (see e.g., US 2012/0251531), and still in another instance the at least one further amino acid substitution is L234A and L235A and P329G of the human IgG1 Fc region.

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain instance, an antibody variant comprises an Fc region with one or more amino acid substitutions which improve ADCC, e.g., substitutions at positions 298, 333, and/or 334 of the Fc region (EU numbering of residues).

In some instances, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424, or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

In some aspects, the anti-CD20/anti-CD3 bispecific antibody comprises an Fc region comprising an N297G mutation (EU numbering).

In some instances, the anti-CD20/anti-CD3 bispecific antibody comprises one or more heavy chain constant domains, wherein the one or more heavy chain constant domains are selected from a first CH1 (CH1[1]) domain, a first CH2 (CH2[1]) domain, a first CH3 (CH3[1]) domain, a second CH1 (CH1[2]) domain, second CH2 (CH2[2]) domain, and a second CH3 (CH3[2]) domain. In some instances, at least one of the one or more heavy chain constant domains is paired with another heavy chain constant domain. In some instances, the CH3$_1$ and CH3$_2$ domains each comprise a protuberance or cavity, and wherein the protuberance or cavity in the CH3$_1$ domain is positionable in the cavity or protuberance, respectively, in the CH3$_2$ domain. In some instances, the CH3$_1$ and CH3$_2$ domains meet at an interface between said protuberance and cavity. In some instances, the CH2$_1$ and CH2$_2$ domains each comprise a protuberance or cavity, and wherein the protuberance or cavity in the CH2$_1$ domain is positionable in the cavity or protuberance, respectively, in the CH2$_2$ domain. In other instances, the CH2$_1$ and CH2$_2$ domains meet at an interface between said protuberance and cavity. In some instances, the anti-CD20/anti-CD3 bispecific antibody is an IgG1 antibody.

d. Cysteine Engineered Antibody Variants

In certain instances, it is desirable to create cysteine engineered anti-CD20/anti-CD3 bispecific antibodies, e.g., "thioMAbs," in which one or more residues of an antibody are substituted with cysteine residues. In particular instances, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain instances, any one or more of the following residues are substituted with cysteine: V205 (Kabat numbering) of the light chain; A118 (EU numbering) of the heavy chain; and S400 (EU numbering) of the heavy chain Fc region. Cysteine engineered antibodies may be generated as described, for example, in U.S. Pat. No. 7,521, 541.

e. Antibody Derivatives

In certain instances, an anti-CD20/anti-CD3 bispecific antibody provided herein is further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another instance, conjugates of an antibody and non-proteinaceous moiety that may be selectively heated by exposure to radiation are provided. In one instance, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

7. Recombinant Production Methods

Anti-CD20/anti-CD3 bispecific antibodies of the invention may be produced using recombinant methods and compositions, for example, as described in U.S. Pat. No. 4,816,567, which is incorporated herein by reference in its entirety.

For recombinant production of an anti-CD20/anti-CD3 bispecific antibody, nucleic acid encoding an antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, NJ, 2003), pp. 245-254, describing expression of antibody fragments in E. coli.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR⁻ CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B. K. C. Lo, ed., Humana Press, Totowa, NJ), pp. 255-268 (2003).

8. Immunoconjugates

The invention also provides immunoconjugates comprising an anti-CD20/anti-CD3 bispecific antibody of the invention conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In some instances, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bloorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another instance, an immunoconjugate comprises an anti-CD20/anti-CD3 bispecific antibody conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another instance, an immunoconjugate comprises an anti-CD20/anti-CD3 bispecific antibody conjugated to a radioactive atom to form a radioconjugate. A variety of radioactive isotopes are available for the production of radioconjugates. Examples include $^{211}$At, $^{131}$I, $^{125}$I, $^{90}$Y, $^{186}$Re, $^{188}$Re, $^{153}$Sm, $^{212}$Bi, $^{32}$P, $^{212}$Pb and radioactive isotopes of Lu. When the radioconjugate is used for detection, it may comprise a radioactive atom for scintigraphic studies, for example $^{99m}$Tc or $^{123}$I, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker, or disulfide-containing linker (Chari et al., *Cancer Res.* 52:127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A).

D. Additional Therapeutic Agents

In some instances, the methods described herein include administering the bispecific anti-CD20/anti-CD3 antibody in combination with one or more additional therapeutic agents.

In some instances, the one or more additional therapeutic agents may reduce the rate or the severity of cytokine release syndrome (CRS). In some instances, the one or more additional therapeutic agents may prevent symptoms associated with CRS. In particular instances, the additional therapeutic agent used to reduce the rate or severity of CRS or prevent symptoms associated with CRS is a corticosteroid (e.g., dexamethasone (CAS #: 50-02-2), prednisone (CAS #: 53-03-2), prednisolone (CAS #50-42-8), or methylprednisolone (CAS #: 83-43-2)) or an IL-6R antagonist (e.g., tocilizumab, sarilumab, vobarilizumab (ALX-0061), satralizumab (SA-237), and variants thereof). In some instances, the additional therapeutic agent is dexamethasone. In some instances, the additional therapeutic agent is prednisone. In some instances, the additional therapeutic agent is tocilizumab.

The methods described herein may result in an improved benefit-risk profile for subjects having a previously untreated (1 L) B cell proliferative disorder (e.g., 1 L non-Hodgkin's lymphoma (NHL) (e.g., 1 L diffuse-large B cell lymphoma (DLBCL)) or 1 L high grade B-cell lymphoma) being treated with an anti-CD20/anti-CD3 bispecific antibody. In some instances, treatment using the methods described herein that result in intravenously administering the anti-CD20/anti-CD3 bispecific antibody in the context of a fractionated, dose-escalation dosing regimen results in a reduction (e.g., by 20% or greater, 25% or greater, 30% or greater, 35% or greater, 40% or greater, 45% or greater, 50% or greater, 55% or greater, 60% or greater, 65% or greater, 70% or greater, 75% or greater, 80% or greater, 85% or greater, 90% or greater, 95% or greater, 96% or greater, 97% or greater, 98% or greater, or 99% or greater; e.g., between 20% and 100%, between 20% and 90%, between 20% and 80%, between 20% and 70%, between 20% and 60%, between 20% and 50%, between 20% and 40%, between 20% and 30%, between 40% and 100%, between 60% and 100%, between 80% and 100%, between 30% and 70%, between 40% and 60%, between 30% and 50%, between 50% and 80%, or between 90% and 100%; e.g., about 20%, about 25%, about 30%, about 35%, about 40%, about 45%, about 50%, about 55%, about 60%, about 65%, about 70%, about 75%, about 80%, about 85%, about 90%, about 95%, about 97%, about 99%, or about 100%) or complete inhibition (100% reduction) of undesirable events, such as cytokine-driven toxicities (e.g., cytokine release syndrome (CRS)), infusion-related reactions (IRRs), macrophage activation syndrome (MAS), neurologic toxicities, severe tumor lysis syndrome (TLS), neutropenia, thrombocytopenia, elevated liver enzymes, and/or hepatotoxicities, following treatment with an anti-CD20/anti-CD3 bispecific antibody using the fractionated, dose-escalation dosing regimen of the invention relative to treatment with an anti-CD20/anti-CD3 bispecific antibody using a non-fractioned dosing regimen.

For all the methods described herein, the anti-CD20/anti-CD3 bispecific antibody is formulated, dosed, and administered in a fashion consistent with good medical practice. Factors for consideration in this context include the particular disorder being treated, the particular mammal being treated, the clinical condition of the individual subject, the cause of the disorder, the site of delivery of the agent, the method of administration, the scheduling of administration, and other factors known to medical practitioners. The anti-CD20/anti-CD3 bispecific antibody need not be, but is optionally formulated with, one or more agents currently used to prevent or treat the disorder in question. The effective amount of such other agents depends on the amount of the anti-CD20/anti-CD3 bispecific antibody present in the formulation, the type of disorder or treatment, and other factors discussed above. The anti-CD20/anti-CD3 bispecific antibody may be suitably administered to the subject over a series of treatments.

In some instances, additional therapeutic agents useful in the present invention include therapeutic antibodies, such as alemtuzumab (CAMPATH®), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (BEXXAR®, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, tafasitamab, talizumab, tefibazumab, tocilizumab, toralizumab, tucotuzumab celmoleukin, tucusituzumab, umavizumab, urtoxazumab, ustekinumab, visilizumab, and briakinumab.

IV. PHARMACEUTICAL COMPOSITIONS AND FORMULATIONS

Any of the antibodies (e.g., anti-CD20/anti-CD3 bispecific antibodies) described herein can be used in pharmaceutical compositions and formulations. Pharmaceutical compositions and formulations of antibodies and/or other agents describe herein can be prepared by mixing one, two, or all three agents having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in U.S. Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171, 586 and WO2006/044908, the latter formulations including a histidine-acetate buffer.

The formulation herein may also contain more than one active ingredient as necessary for the particular indication being treated, preferably those with complementary activities that do not adversely affect each other. For example, it may be desirable to further provide an additional therapeutic agent (e.g., a chemotherapeutic agent, a cytotoxic agent, a growth inhibitory agent, and/or an anti-hormonal agent, such as those recited herein above). Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, for example, films, or microcapsules.

The formulations to be used for in vivo administration are generally sterile. Sterility may be readily accomplished, e.g., by filtration through sterile filtration membranes.

V. KITS AND ARTICLES OF MANUFACTURE

In another aspect of the invention, a kit or an article of manufacture containing materials useful for the treatment, prevention, and/or diagnosis of the disorders described above is provided. The kit or article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be a vial having a stopper pierceable by a hypodermic injection needle). At least one active agent in the composition is an anti-CD20/anti-CD3 bispecific antibody described herein. The label or package insert indicates that the composition is used for treating the previously untreated condition of choice (e.g., a previously untreated B cell proliferation disorder, e.g., a high grade B-cell lymphoma (HGBL) or non-Hodgkin's lymphoma (NHL), e.g., diffuse large B cell lymphoma (DLBCL)) and further includes information related to at least one of the dosing regimens described herein. Moreover, the kit or article of manufacture may comprise (a) a first container with a composition contained therein, wherein the composition comprises an anti-CD20/anti-CD3 bispecific antibody described herein; and (b) a second container with a composition contained therein, wherein the composition comprises a further cytotoxic or otherwise therapeutic agent. Alternatively, or additionally, the kit or article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

VI. EMBODIMENTS

Some embodiments of the technology described herein can be defined according to any of the following numbered embodiments:

1. A method of treating a subject having a previously untreated B cell proliferative disorder comprising intravenously administering to the subject, as a monotherapy, mosunetuzumab in a dosing regimen comprising at least a first dosing cycle and a second dosing cycle, wherein:
   (a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and
   (b) the second dosing cycle comprises a single dose (C2D1) of the mosunetuzumab, wherein the C2D1 is equivalent in amount to the C1D3.

2. Mosunetuzumab for use in treating a subject having a previously untreated B cell proliferative disorder, wherein the mosunetuzumab is formulated as a monotherapy for intravenous administration to the subject in a dosing regimen comprising at least a first dosing cycle and a second dosing cycle, wherein:
   (a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and
   (b) the second dosing cycle comprises a single dose (C2D1) of the mosunetuzumab, wherein the C2D1 is equivalent in amount to the C1D3.

3. Use of mosunetuzumab in treating a subject having a previously untreated B cell proliferative disorder, wherein the mosunetuzumab is formulated as a monotherapy for intravenous administration to the subject in a dosing regimen comprising at least a first dosing cycle and a second dosing cycle, wherein:
   (a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and
   (b) the second dosing cycle comprises a single dose (C2D1) of the mosunetuzumab, wherein the C2D1 is equivalent in amount to the C1D3.

4. Use of mosunetuzumab in the manufacture of a medicament in treating a subject having a previously untreated B cell proliferative disorder, wherein the mosunetuzumab is formulated as a monotherapy for intravenous administration to the subject in a dosing regimen comprising at least a first dosing cycle and a second dosing cycle, wherein:
   (a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and
   (b) the second dosing cycle comprises a single dose (C2D1) of the mosunetuzumab, wherein the C2D1 is equivalent in amount to the C1D3.

5. A method of treating an elderly subject having a previously untreated B cell proliferative disorder comprising intravenously administering to the subject, as a monotherapy, mosunetuzumab in a dosing regimen comprising at least a first dosing cycle and a second dosing cycle, wherein:
   (a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and
   (b) the second dosing cycle comprises a single dose (C2D1) of the mosunetuzumab, wherein the C2D1 is equivalent in amount to the C1D3.

6. Mosunetuzumab for use in treating an elderly subject having a previously untreated B cell proliferative disorder, wherein the mosunetuzumab is formulated as a monotherapy for intravenous administration to the subject in a dosing regimen comprising at least a first dosing cycle and a second dosing cycle, wherein:
   (a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and
   (b) the second dosing cycle comprises a single dose (C2D1) of the mosunetuzumab, wherein the C2D1 is equivalent in amount to the C1D3.

7. Use of mosunetuzumab in treating an elderly subject having a previously untreated B cell proliferative disorder, wherein the mosunetuzumab is formulated as a monotherapy for intravenous administration to the subject in a dosing regimen comprising at least a first dosing cycle and a second dosing cycle, wherein:

(a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and (b) the second dosing cycle comprises a single dose (C2D1) of the mosunetuzumab, wherein the C2D1 is equivalent in amount to the C1D3.

8. Use of mosunetuzumab in the manufacture of a medicament for treating an elderly subject having a previously untreated B cell proliferative disorder comprising intravenously administering to the subject, as a monotherapy, mosunetuzumab in a dosing regimen comprising at least a first dosing cycle and a second dosing cycle, wherein:

(a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and (b) the second dosing cycle comprises a single dose (C2D1) of the mosunetuzumab, wherein the C2D1 is equivalent in amount to the C1D3.

9. The method, mosunetuzumab for use, or use of any one of embodiments 5-8, wherein the elderly subject is at least 60-years old.

10. The method, mosunetuzumab for use, or use of embodiment 9, wherein the elderly subject is at least 65-years old.

11. The method, mosunetuzumab for use, or use of embodiment 10, wherein the elderly subject is at least 80-years old.

12. A method of treating an unfit subject having a previously untreated B cell proliferative disorder comprising intravenously administering to the subject, as a monotherapy, mosunetuzumab in a dosing regimen comprising at least a first dosing cycle and a second dosing cycle, wherein:

(a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and (b) the second dosing cycle comprises a single dose (C2D1) of the mosunetuzumab, wherein the C2D1 is equivalent in amount to the C1D3.

13. Mosunetuzumab for use in treating an unfit subject having a previously untreated B cell proliferative disorder, wherein the mosunetuzumab is formulated as a monotherapy for intravenous administration to the subject in a dosing regimen comprising at least a first dosing cycle and a second dosing cycle, wherein:

(a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and (b) the second dosing cycle comprises a single dose (C2D1) of the mosunetuzumab, wherein the C2D1 is equivalent in amount to the C1D3.

14. Use of mosunetuzumab in treating an unfit subject having a previously untreated B cell proliferative disorder comprising intravenously administering to the subject, as a monotherapy, mosunetuzumab in a dosing regimen comprising at least a first dosing cycle and a second dosing cycle, wherein:

(a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and (b) the second dosing cycle comprises a single dose (C2D1) of the mosunetuzumab, wherein the C2D1 is equivalent in amount to the C1D3.

15. Use of mosunetuzumab in the manufacture of a medicament for treating an unfit subject having a previously untreated B cell proliferative disorder comprising intravenously administering to the subject, as a monotherapy, mosunetuzumab in a dosing regimen comprising at least a first dosing cycle and a second dosing cycle, wherein:

(a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and (b) the second dosing cycle comprises a single dose (C2D1) of the mosunetuzumab, wherein the C2D1 is equivalent in amount to the C1D3.

16. The method, mosunetuzumab for use, or use of any one of embodiments 12-15, wherein the unfit subject is at least 60-years old.

17. The method, mosunetuzumab for use, or use of embodiment 16, wherein the unfit subject is 60-years to 79-years old.

18. The method, mosunetuzumab for use, or use of any one of embodiments 12-17, wherein the unfit subject exhibits:

(i) an impairment in at least one activity of daily living (ADL) component;

(ii) an impairment in at least one instrumental activity of daily living (IADL) component;

(iii) an impairment in at least one of cardiac function, vascular function, renal function, and/or liver function; and/or (iv) diabetes.

19. The method, mosunetuzumab for use, or use of embodiment 18, wherein the unfit subject exhibits an impairment in at least one ADL component.

20. The method, mosunetuzumab for use, or use of embodiment 18, wherein the unfit subject exhibits an impairment in at least one IADL component.

21. The method, mosunetuzumab for use, or use of embodiment 18, wherein the unfit subject exhibits an impairment in cardiac function comprising heart arrhythmia, congestive heart failure (CHF), myocardial infarction, and/or cardiac-related symptoms of hypothyroidism.

22. The method, mosunetuzumab for use, or use of embodiment 18, wherein the unfit subject exhibits an impairment in vascular function comprising anemia, cerebrovascular accident (CVA), cerebrovascular disease (CVD), chronic obstructive pulmonary disease not otherwise specified (COPD: NOS), hyperlipidemia, peripheral vascular disease, stroke, and/or ischemic attack (TIA).

23. The method, mosunetuzumab for use, or use of embodiment 18, wherein the unfit subject exhibits an impairment in renal function comprising acute kidney disease and/or chronic kidney disease.

24. The method, mosunetuzumab for use, or use of embodiment 18, wherein the unfit subject exhibits an impairment in liver function.

25. The method, mosunetuzumab for use, or use of embodiment 18, wherein the unfit subject exhibits diabetes, comprising type 2 diabetes, diabetes with end organ damage (EOD), and/or diabetes without EOD.

26. The method, mosunetuzumab for use, or use of any one of embodiments 1-25, wherein the subject is unsuitable for treatment with R-CHOP therapy.

27. A method of treating a subject having a previously untreated B cell proliferative disorder comprising intravenously administering to the subject, as a monotherapy, mosunetuzumab in a dosing regimen comprising at least a first dosing cycle and a second dosing cycle, wherein:
   (a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and
   (b) the second dosing cycle comprises a single dose (C2D1) of the mosunetuzumab, wherein the C2D1 is equivalent in amount to the C1D3,
wherein the subject is unsuitable for treatment with R-CHOP therapy.

28. Mosunetuzumab for use in treating a subject having a previously untreated B cell proliferative disorder, wherein the mosunetuzumab is formulated as a monotherapy for intravenous administration to the subject in a dosing regimen comprising at least a first dosing cycle and a second dosing cycle, wherein:
   (a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and
   (b) the second dosing cycle comprises a single dose (C2D1) of the mosunetuzumab, wherein the C2D1 is equivalent in amount to the C1D3,
wherein the subject is unsuitable for treatment with R-CHOP therapy.

29. Use of mosunetuzumab in treating a subject having a previously untreated B cell proliferative disorder, wherein the mosunetuzumab is formulated as a monotherapy for intravenous administration to the subject in a dosing regimen comprising at least a first dosing cycle and a second dosing cycle, wherein:
   (a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and
   (b) the second dosing cycle comprises a single dose (C2D1) of the mosunetuzumab, wherein the C2D1 is equivalent in amount to the C1D3,
wherein the subject is unsuitable for treatment with R-CHOP therapy.

30. Use of mosunetuzumab in the manufacture of a medicament for treating a subject having a previously untreated B cell proliferative disorder, wherein the mosunetuzumab is formulated as a monotherapy for intravenous administration to the subject in a dosing regimen comprising at least a first dosing cycle and a second dosing cycle, wherein:
   (a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and
   (b) the second dosing cycle comprises a single dose (C2D1) of the mosunetuzumab, wherein the C2D1 is equivalent in amount to the C1D3,
wherein the subject is unsuitable for treatment with R-CHOP therapy.

31. The method, mosunetuzumab for use, or use of any one of embodiments 26-30, wherein the R-CHOP therapy comprises rituximab, cyclophosphamide, doxorubicin, vincristine, and prednisone, and further wherein the rituximab is administered to the subject at a dose of 375 mg/m$^2$ every three weeks.

32. The method, mosunetuzumab for use, or use of any one of embodiments 1-31, wherein the C1D3 and the C2D1 are each 13.5 mg.

33. The method, mosunetuzumab for use, or use of any one of embodiments 1-31, wherein the C1D3 and the C2D1 are each 30 mg.

34. The method, mosunetuzumab for use, or use of any one of embodiments 1-33, wherein the first and second dosing cycles are 21-day dosing cycles.

35. The method, mosunetuzumab for use, or use of any one of embodiments 1-34, wherein the method comprises administering the C1D1, the C1D2, and the C1D3 on Days 1, 8, and 15, respectively, of the first dosing cycle.

36. The method, mosunetuzumab for use, or use of any one of embodiments 1-35, wherein the method comprises administering the C2D1 on Day 1 of the second dosing cycle.

37. The method, mosunetuzumab for use, or use of any one of embodiments 1-36, wherein the dosing regimen further comprises one or more additional dosing cycles.

38. The method, mosunetuzumab for use, or use of embodiment 37, wherein the dosing regimen comprises six to 15 additional dosing cycles.

39. The method, mosunetuzumab for use, or use of embodiment 38, wherein the dosing regimen comprises six additional dosing cycles.

40. The method, mosunetuzumab for use, or use of embodiment 38, wherein the dosing regimen comprises 15 additional dosing cycles.

41. The method, mosunetuzumab for use, or use of any one of embodiments 37-40, wherein the additional dosing cycles are 21-day dosing cycles.

42. The method, mosunetuzumab for use, or use of any one of embodiments 37-41, wherein one or more of the additional dosing cycles comprise an additional single dose of the mosunetuzumab.

43. The method, mosunetuzumab for use, or use of embodiment 42, wherein the additional single dose of the mosunetuzumab is administered to the subject on Day 1 of each additional dosing cycle.

44. The method, mosunetuzumab for use, or use of embodiment 42 or 43, wherein the additional single dose of the mosunetuzumab is equivalent in amount to the C1D3.

45. The method, mosunetuzumab for use, or use of any one of embodiments 42-45, wherein the additional single dose of the mosunetuzumab is 13.5 mg.

46. The method, mosunetuzumab for use, or use of any one of embodiments 42-45, wherein the additional single dose of the mosunetuzumab is 30 mg.

47. The method of any one of embodiments 1, 5, 9-12, 16-27, and 31-46, wherein the method further comprises administering to the subject one or more additional therapeutic agents.

48. The mosunetuzumab for use or use of any one of embodiments 2-4, 6-11, 13-26, and 28-46, wherein mosunetuzumab is to be administered with one or more additional therapeutic agents.

49. The method, mosunetuzumab for use, or use of embodiment 47 or 48, wherein the one or more additional therapeutic agents is tocilizumab.

50. The method, mosunetuzumab for use, or use of embodiment 47 or 48, wherein the one or more additional therapeutic agents is an antihistamine.

51. The method, mosunetuzumab for use, or use of embodiment 50, wherein the antihistamine is diphenhydramine.

52. The method, mosunetuzumab for use, or use of embodiment 47 or 48, wherein the one or more additional therapeutic agents comprises allopurinol and rasburicase.

53. The method, mosunetuzumab for use, or use of embodiment 47 or 48, wherein the one or more additional therapeutic agents is a corticosteroid.

54. The method, mosunetuzumab for use, or use of embodiment 53, wherein the corticosteroid comprises prednisone, prednisolone, methylprednisolone, and dexamethasone.

55. The method, mosunetuzumab for use, or use of embodiment 54, wherein the corticosteroid comprises prednisone.

56. The method, mosunetuzumab for use, or use of embodiment 55, wherein the prednisone is administered to the subject on each of the seven days prior to the administration of the C1D1.

57. The method, mosunetuzumab for use, or use of embodiment 56, wherein the prednisone is administered at a dose of 100 mg/day.

58. The method, mosunetuzumab for use, or use of embodiment 57, wherein the one or more additional therapeutic agents comprises a single dose of vincristine, and wherein the single dose of vincristine is 1 mg.

59. The method, mosunetuzumab for use, or use of embodiment 58, wherein the single dose of vincristine is administered to the subject seven days prior to the administration of the C1D1.

60. The method, mosunetuzumab for use, or use of any one of embodiments 1-59, wherein the previously untreated B cell proliferative disorder is a previously untreated high grade B-cell lymphoma.

61. The method, mosunetuzumab for use, or use of any one of embodiments 1-59, wherein the previously untreated B cell proliferative disorder is a previously untreated non-Hodgkin's lymphoma (NHL).

62. The method, mosunetuzumab for use, or use of embodiment 61, wherein the previously untreated NHL is a previously untreated DLBCL.

63. A method of treating a population of subjects having a previously untreated DLBCL comprising intravenously administering to the subjects, as a monotherapy, mosunetuzumab in a dosing regimen comprising eight 21-day dosing cycles, wherein:
(a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and
(b) the second to eighth dosing cycles each comprises a single dose (C2D1-C8D1) of the mosunetuzumab, wherein each single dose C2D1-C8D1 is equivalent in amount to the C1D3,
wherein the subjects are at least 65-years old, and wherein the subjects are unfit for treatment with standard R-CHOP therapy.

64. Mosunetuzumab for use in treating a population of subjects having a previously untreated DLBCL, wherein the mosunetuzumab is formulated as a monotherapy for intravenous administration to the subjects in a dosing regimen comprising eight 21-day dosing cycles, wherein:
(a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and
(b) the second to eighth dosing cycles each comprises a single dose (C2D1-C8D1) of the mosunetuzumab, wherein each single dose C2D1-C8D1 is equivalent in amount to the C1D3,
wherein the subjects are at least 65-years old, and wherein the subjects are unfit for treatment with standard R-CHOP therapy.

65. Use of mosunetuzumab in treating a population of subjects having a previously untreated DLBCL, wherein the mosunetuzumab is formulated as a monotherapy for intravenous administration to the subjects in a dosing regimen comprising eight 21-day dosing cycles, wherein:
(a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and
(b) the second to eighth dosing cycles each comprises a single dose (C2D1-C8D1) of the mosunetuzumab, wherein each single dose C2D1-C8D1 is equivalent in amount to the C1D3,
wherein the subjects are at least 65-years old, and wherein the subjects are unfit for treatment with standard R-CHOP therapy.

66. Use of mosunetuzumab in the manufacture of a medicament for treating a population of subjects having a previously untreated DLBCL, wherein the mosunetuzumab is formulated as a monotherapy for intravenous administration to the subjects in a dosing regimen comprising eight 21-day dosing cycles, wherein:
(a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and
(b) the second to eighth dosing cycles each comprises a single dose (C2D1-C8D1) of the mosunetuzumab, wherein each single dose C2D1-C8D1 is equivalent in amount to the C1D3,
wherein the subjects are at least 65-years old, and wherein the subjects are unfit for treatment with standard R-CHOP therapy.

67. A method of treating a population of subjects having a previously untreated DLBCL comprising intravenously administering to the subjects, as a monotherapy, mosunetuzumab in a dosing regimen comprising seventeen 21-day dosing cycles, wherein:
(a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and
(b) the second to seventeenth dosing cycles each comprises a single dose (C2D1-C17D1) of the mosunetuzumab, wherein each single dose C2D1-C17D1 is equivalent in amount to the C1D3,
wherein the subjects are at least 65-years old, and wherein the subjects are unfit for treatment with standard R-CHOP therapy.

68. Mosunetuzumab for use in treating a population of subjects having a previously untreated DLBCL, wherein the mosunetuzumab is formulated as a monotherapy for intravenous administration to the subjects in a dosing regimen comprising seventeen 21-day dosing cycles, wherein:

(a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and (b) the second to seventeenth dosing cycles each comprises a single dose (C2D1-C17D1) of the mosunetuzumab, wherein each single dose C2D1-C17D1 is equivalent in amount to the C1D3, wherein the subjects are at least 65-years old, and wherein the subjects are unfit for treatment with standard R-CHOP therapy.

69. Use of mosunetuzumab in treating a population of subjects having a previously untreated DLBCL, wherein the mosunetuzumab is formulated as a monotherapy for intravenous administration to the subjects in a dosing regimen comprising seventeen 21-day dosing cycles, wherein:

(a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and (b) the second to seventeenth dosing cycles each comprises a single dose (C2D1-C17D1) of the mosunetuzumab, wherein each single dose C2D1-C17D1 is equivalent in amount to the C1D3, wherein the subjects are at least 65-years old, and wherein the subjects are unfit for treatment with standard R-CHOP therapy.

70. Use of mosunetuzumab in the manufacture of a medicament for treating a population of subjects having a previously untreated DLBCL, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and (b) the second to seventeenth dosing cycles each comprises a single dose (C2D1-C17D1) of the mosunetuzumab, wherein each single dose C2D1-C17D1 is equivalent in amount to the C1D3, wherein the subjects are at least 65-years old, and wherein the subjects are unfit for treatment with standard R-CHOP therapy.

71. The method, mosunetuzumab for use, or use of any one of embodiments 63-70, wherein the overall response rate is greater than 56%.

72. The method, mosunetuzumab for use, or use of embodiment 71, wherein the overall response rate is greater than 61%.

73. The method, mosunetuzumab for use, or use of any one of embodiments 63-70, wherein the complete response rate is greater than 38%.

74. The method, mosunetuzumab for use, or use of embodiment 73, wherein the complete response rate is greater than 43%.

75. The method, mosunetuzumab for use, or use of embodiment 73 or 74, wherein greater than 42% of subjects having a complete response maintained complete remission for 12 months.

76. The method, mosunetuzumab for use, or use of embodiment 75, wherein greater than 47% of subjects having a complete response maintained complete remission for 12 months.

77. The method, mosunetuzumab for use, or use of any one of embodiments 63-70, wherein the rate of cytokine release syndrome having a grade of 3 or higher (as defined by the American Society for Transplantation and Cellular Therapy®, 2018; ASTCT®) is less than 5%.

78. The method, mosunetuzumab for use, or use of embodiment 77, wherein the rate of cytokine release syndrome having a grade of 3 or higher (as defined by the ASTCT®) is less than 3%.

79. The method, mosunetuzumab for use, or use of embodiment 78, wherein the rate of cytokine release syndrome having a grade of 3 or higher (as defined by the ASTCT®) is less than 1%.

80. The method, mosunetuzumab for use, or use of embodiment 79, wherein the rate of cytokine release syndrome having a grade of 3 or higher (as defined by the ASTCT®) is 0%, 81. A method of treating a subject having a previously untreated B cell proliferative disorder comprising intravenously administering to the subject, as a monotherapy, mosunetuzumab in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab, wherein each single dose C2D1-C8D1 is equivalent in amount to the C1D3.

82. A method of treating a subject having a previously untreated B cell proliferative disorder comprising intravenously administering to the subject, as a monotherapy, mosunetuzumab in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to eighth dosing cycles each comprises a single dose (C2D1-C8D1) of mosunetuzumab, wherein each single dose C2D1-C8D1 is equivalent in amount to the C1D3.

83. A method of treating a subject having a previously untreated B cell proliferative disorder comprising intravenously administering to the subject, as a monotherapy, mosunetuzumab in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to seventeenth dosing cycles each comprises a single dose (C2D1-C17D1) of mosunetuzumab, wherein each single dose C2D1-C17D1 is equivalent in amount to the C1D3.

84. A method of treating a subject having a previously untreated B cell proliferative disorder comprising intravenously administering to the subject, as a monotherapy, mosunetuzumab in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab, wherein each single dose C2D1-C17D1 is equivalent in amount to the C1D3.

85. A method of treating a subject having a previously untreated DLBCL comprising intravenously administering to the subject, as a monotherapy, mosunetuzumab in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab, wherein each single dose C2D1-C8D1 is equivalent in amount to the C1D3.

86. A method of treating a subject having a previously untreated DLBCL comprising intravenously administering to the subject, as a monotherapy, mosunetuzumab in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to eighth dosing cycles each comprises a single dose (C2D1-C8D1) of mosunetuzumab, wherein each single dose C2D1-C8D1 is equivalent in amount to the C1D3.

87. A method of treating a subject having a previously untreated DLBCL comprising intravenously administering to the subject, as a monotherapy, mosunetuzumab in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to seventeenth dosing cycles each comprises a single dose (C2D1-C17D1) of mosunetuzumab, wherein each single dose C2D1-C17D1 is equivalent in amount to the C1D3.

88. A method of treating a subject having a previously untreated DLBCL comprising intravenously administering to the subject, as a monotherapy, mosunetuzumab in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab, wherein each single dose C2D1-C17D1 is equivalent in amount to the C1D3.

89. A method of treating a subject having a previously untreated DLBCL comprising intravenously administering to the subject, as a monotherapy, mosunetuzumab in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab, wherein each single dose C2D1-C8D1 is equivalent in amount to the C1D3, wherein the subject is at least 65-years old, and wherein the subject is unfit for treatment with standard R-CHOP therapy.

90. A method of treating a subject having a previously untreated DLBCL comprising intravenously administering to the subject, as a monotherapy, mosunetuzumab in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to eighth dosing cycles each comprises a single dose (C2D1-C8D1) of mosunetuzumab, wherein each single dose C2D1-C8D1 is equivalent in amount to the C1D3, wherein the subject is at least 65-years old, and wherein the subject is unfit for treatment with standard R-CHOP therapy.

91. A method of treating a subject having a previously untreated DLBCL comprising intravenously administering to the subject, as a monotherapy, mosunetuzumab in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to seventeenth dosing cycles each comprises a single dose (C2D1-C17D1) of mosunetuzumab, wherein each single dose C2D1-C17D1 is equivalent in amount to the C1D3, wherein the subject is at least 65-years old, and wherein the subject is unfit for treatment with standard R-CHOP therapy.

92. A method of treating a subject having a previously untreated DLBCL comprising intravenously administering to the subject, as a monotherapy, mosunetuzumab in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab, wherein each single dose C2D1-C17D1 is equivalent in amount to the C1D3, wherein the subject is at least 65-years old, and wherein the subject is unfit for treatment with standard R-CHOP therapy.

93. A method of treating an elderly subject having a previously untreated DLBCL comprising intravenously administering to the subject, as a monotherapy, mosunetuzumab in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab, wherein each single dose C2D1-C8D1 is equivalent in amount to the C1D3, wherein the subject is at least 80-years old.

94. A method of treating an elderly subject having a previously untreated DLBCL comprising intravenously administering to the subject, as a monotherapy, mosunetuzumab in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to eighth dosing cycles each comprises a single dose (C2D1-C8D1) of mosunetuzumab, wherein each single dose C2D1-C8D1 is equivalent in amount to the C1D3, wherein the subject is at least 80-years old.

95. A method of treating an elderly subject having a previously untreated DLBCL comprising intravenously administering to the subject, as a monotherapy, mosunetuzumab in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to seventeenth dosing cycles each comprises a single dose (C2D1-C17D1) of mosunetuzumab, wherein each single dose C2D1-C17D1 is equivalent in amount to the C1D3, wherein the subject is at least 80-years old.

96. A method of treating an elderly subject having a previously untreated DLBCL comprising intravenously administering to the subject, as a monotherapy, mosunetuzumab in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab, wherein each single dose C2D1-C17D1 is equivalent in amount to the C1D3, wherein the subject is at least 80-years old.

97. A method of treating an unfit subject having a previously untreated DLBCL comprising intravenously administering to the subject, as a monotherapy, mosunetuzumab in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab, wherein each single dose C2D1-C8D1 is equivalent in amount to the C1D3, wherein the subject is at least 60-years old, and wherein the subject exhibits:

(i) an impairment in at least ADL component (Katz et al., 1970);

(ii) an impairment in at least one IADL component (Lawton and Brody, 1969);

(iii) an impairment in at least one of cardiac function, vascular function, renal function, and/or liver function; and/or (iv) diabetes.

98. A method of treating an unfit subject having a previously untreated DLBCL comprising intravenously administering to the subject, as a monotherapy, mosunetuzumab in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to eighth dosing cycles each comprises a single dose (C2D1-C8D1) of mosunetuzumab, wherein each single dose C2D1-C8D1 is equivalent in amount to the C1D3, wherein the subject is at least 60-years old, and wherein the subject exhibits:

(i) an impairment in at least ADL component;

(ii) an impairment in at least one IADL component;

(iii) an impairment in at least one of cardiac function, vascular function, renal function, and/or liver function; and/or (iv) diabetes.

99. A method of treating an unfit subject having a previously untreated DLBCL comprising intravenously administering to the subject, as a monotherapy, mosunetuzumab in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to seventeenth dosing cycles each comprises a single dose (C2D1-C17D1) of mosunetuzumab, wherein each single dose C2D1-C17D1 is equivalent in amount to the C1D3, wherein the subject is at least 60-years old, and wherein the subject exhibits:

(i) an impairment in at least ADL component;

(ii) an impairment in at least one IADL component;

(iii) an impairment in at least one of cardiac function, vascular function, renal function, and/or liver function; and/or (iv) diabetes.

100. A method of treating an unfit subject having a previously untreated DLBCL comprising intravenously administering to the subject, as a monotherapy, mosunetuzumab in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab, wherein each single dose C2D1-C17D1 is equivalent in amount to the C1D3, wherein the subject is at least 60-years old, and wherein the subject exhibits:

(i) an impairment in at least ADL component;

(ii) an impairment in at least one IADL component;

(iii) an impairment in at least one of cardiac function, vascular function, renal function, and/or liver function; and/or (iv) diabetes.

101. Mosunetuzumab for use in treating a subject having a previously untreated B cell proliferative disorder, wherein the mosunetuzumab is formulated as a monotherapy for intravenous administration to the subject in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab, wherein each single dose C2D1-C8D1 is equivalent in amount to the C1D3.

102. Mosunetuzumab for use in treating a subject having a previously untreated B cell proliferative disorder, wherein the mosunetuzumab is formulated as a monotherapy for intravenous administration to the subject in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to eighth dosing cycles each comprises a single dose (C2D1-C8D1) of mosunetuzumab, wherein each single dose C2D1-C8D1 is equivalent in amount to the C1D3.

103. Mosunetuzumab for use in treating a subject having a previously untreated B cell proliferative disorder, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to seventeenth dosing cycles each comprises a single dose (C2D1-C17D1) of mosunetuzumab, wherein each single dose C2D1-C17D1 is equivalent in amount to the C1D3.

104. Mosunetuzumab for use in treating a subject having a previously untreated B cell proliferative disorder, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab, wherein each single dose C2D1-C17D1 is equivalent in amount to the C1D3.

105. Mosunetuzumab for use in treating a subject having a previously untreated DLBCL, wherein the mosunetuzumab is formulated as a monotherapy for intravenous administration to the subject in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab, wherein each single dose C2D1-C8D1 is equivalent in amount to the C1D3.

106. Mosunetuzumab for use in treating a subject having a previously untreated DLBCL, wherein the mosunetuzumab is formulated as a monotherapy for intravenous administration to the subject in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to eighth dosing cycles each comprises a single dose (C2D1-C8D1) of mosunetuzumab, wherein each single dose C2D1-C8D1 is equivalent in amount to the C1D3.

107. Mosunetuzumab for use in treating a subject having a previously untreated DLBCL, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to seventeenth dosing cycles each comprises a single dose (C2D1-C17D1) of mosunetuzumab, wherein each single dose C2D1-C17D1 is equivalent in amount to the C1D3.

108. Mosunetuzumab for use in treating a subject having a previously untreated DLBCL, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab, wherein each single dose C2D1-C17D1 is equivalent in amount to the C1D3.

109. Mosunetuzumab for use in treating a subject having a previously untreated DLBCL, wherein the mosunetuzumab is formulated as a monotherapy for intravenous administration to the subject in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab, wherein each single dose C2D1-C8D1 is equivalent in amount to the C1D3, wherein the subject is at least 65-years old, and wherein the subject is unfit for treatment with standard R-CHOP therapy.

110. Mosunetuzumab for use in treating a subject having a previously untreated DLBCL, wherein the mosunetuzumab is formulated as a monotherapy for intravenous administration to the subject in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to eighth dosing cycles each comprises a single dose (C2D1-C8D1) of mosunetuzumab, wherein each single dose C2D1-C8D1 is equivalent in amount to the C1D3, wherein the subject is at least 65-years old, and wherein the subject is unfit for treatment with standard R-CHOP therapy.

111. Mosunetuzumab for use in treating a subject having a previously untreated DLBCL, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to seventeenth dosing cycles each comprises a single dose (C2D1-C17D1) of mosunetuzumab, wherein each single dose C2D1-C17D1 is equivalent in amount to the C1D3, wherein the subject is at least 65-years old, and wherein the subject is unfit for treatment with standard R-CHOP therapy.

112. Mosunetuzumab for use in treating a subject having a previously untreated DLBCL, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab, wherein each single dose C2D1-C17D1 is equivalent in amount to the C1D3, wherein the subject is at least 65-years old, and wherein the subject is unfit for treatment with standard R-CHOP therapy.

113. Mosunetuzumab for use in treating an elderly subject having a previously untreated DLBCL, wherein the mosunetuzumab is formulated as a monotherapy for intravenous administration to the subject in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab, wherein each single dose C2D1-C8D1 is equivalent in amount to the C1D3, wherein the subject is at least 80-years old.

114. Mosunetuzumab for use in treating an elderly subject having a previously untreated DLBCL, wherein the mosunetuzumab is formulated as a monotherapy for intravenous administration to the subject in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to eighth dosing cycles each comprises a single dose (C2D1-C8D1) of mosunetuzumab, wherein each single dose C2D1-C8D1 is equivalent in amount to the C1D3, wherein the subject is at least 80-years old.

115. Mosunetuzumab for use in treating an elderly subject having a previously untreated DLBCL, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to seventeenth dosing cycles each comprises a single dose (C2D1-C17D1) of mosunetuzumab, wherein each single dose C2D1-C17D1 is equivalent in amount to the C1D3, wherein the subject is at least 80-years old.

116. Mosunetuzumab for use in treating an elderly subject having a previously untreated DLBCL, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab, wherein each single dose C2D1-C17D1 is equivalent in amount to the C1D3, wherein the subject is at least 80-years old.

117. Mosunetuzumab for use in treating an unfit subject having a previously untreated DLBCL, wherein the mosunetuzumab is formulated as a monotherapy for intravenous administration to the subject in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab, wherein each single dose C2D1-C8D1 is equivalent in amount to the C1D3, wherein the subject is at least 60-years old, and wherein the subject exhibits:

(i) an impairment in at least ADL component (Katz et al., 1970);

(ii) an impairment in at least one IADL component (Lawton and Brody, 1969);

(iii) an impairment in at least one of cardiac function, vascular function, renal function, and/or liver function; and/or (iv) diabetes.

118. Mosunetuzumab for use in treating an unfit subject having a previously untreated DLBCL, wherein the mosunetuzumab is formulated as a monotherapy for intravenous administration to the subject in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to eighth dosing cycles each comprises a single dose (C2D1-C8D1) of mosunetuzumab, wherein each single dose C2D1-C8D1 is equivalent in amount to the C1D3, wherein the subject is at least 60-years old, and wherein the subject exhibits:

(i) an impairment in at least ADL component;

(ii) an impairment in at least one IADL component;

(iii) an impairment in at least one of cardiac function, vascular function, renal function, and/or liver function; and/or (iv) diabetes.

119. Mosunetuzumab for use in treating an unfit subject having a previously untreated DLBCL, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to seventeenth dosing cycles each comprises a single dose (C2D1-C17D1) of mosunetuzumab, wherein each single dose C2D1-C17D1 is equivalent in amount to the C1D3, wherein the subject is at least 60-years old, and wherein the subject exhibits:

(i) an impairment in at least ADL component;

(ii) an impairment in at least one IADL component;

(iii) an impairment in at least one of cardiac function, vascular function, renal function, and/or liver function; and/or (iv) diabetes.

120. Mosunetuzumab for use in treating an unfit subject having a previously untreated DLBCL, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab, wherein each single dose C2D1-C17D1 is equivalent in amount to the C1D3, wherein the subject is at least 60-years old, and wherein the subject exhibits:

(i) an impairment in at least ADL component;

(ii) an impairment in at least one IADL component;

(iii) an impairment in at least one of cardiac function, vascular function, renal function, and/or liver function; and/or (iv) diabetes.

121. Use of mosunetuzumab in treating a subject having a previously untreated B cell proliferative disorder, wherein the mosunetuzumab is formulated as a monotherapy for intravenous administration to the subject in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab, wherein each single dose C2D1-C8D1 is equivalent in amount to the C1D3.

122. Use of mosunetuzumab in treating a subject having a previously untreated B cell proliferative disorder, wherein the mosunetuzumab is formulated as a monotherapy for intravenous administration to the subject in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to eighth dosing cycles each comprises a single dose (C2D1-C8D1) of mosunetuzumab, wherein each single dose C2D1-C8D1 is equivalent in amount to the C1D3.

123. Use of mosunetuzumab in treating a subject having a previously untreated B cell proliferative disorder, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to seventeenth dosing cycles each comprises a single dose (C2D1-C17D1) of mosunetuzumab, wherein each single dose C2D1-C17D1 is equivalent in amount to the C1D3.

124. Use of mosunetuzumab in treating a subject having a previously untreated B cell proliferative disorder, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab, wherein each single dose C2D1-C17D1 is equivalent in amount to the C1D3.

125. Use of mosunetuzumab in treating a subject having a previously untreated DLBCL, wherein the mosunetuzumab is formulated as a monotherapy for intravenous administration to the subject in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab, wherein each single dose C2D1-C8D1 is equivalent in amount to the C1D3.

126. Use of mosunetuzumab in treating a subject having a previously untreated DLBCL, wherein the mosunetuzumab is formulated as a monotherapy for intravenous administration to the subject in a dosing regimen comprising eight 21-day dosing cycles, wherein:
    (a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and
    (b) the second to eighth dosing cycles each comprises a single dose (C2D1-C8D1) of mosunetuzumab, wherein each single dose C2D1-C8D1 is equivalent in amount to the C1D3.

127. Use of mosunetuzumab in treating a subject having a previously untreated DLBCL, wherein the mosunetuzumab is formulated as a monotherapy for intravenous administration to the subject in a dosing regimen comprising seventeen 21-day dosing cycles, wherein:
    (a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and
    (b) the second to seventeenth dosing cycles each comprises a single dose (C2D1-C17D1) of mosunetuzumab, wherein each single dose C2D1-C17D1 is equivalent in amount to the C1D3.

128. Use of mosunetuzumab in treating a subject having a previously untreated DLBCL, wherein the mosunetuzumab is formulated as a monotherapy for intravenous administration to the subject in a dosing regimen comprising seventeen 21-day dosing cycles, wherein:
    (a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and
    (b) the second to seventeenth dosing cycles each comprises a single dose (C2D1-C17D1) of mosunetuzumab, wherein each single dose C2D1-C17D1 is equivalent in amount to the C1D3.

129. Use of mosunetuzumab in treating a subject having a previously untreated DLBCL, wherein the mosunetuzumab is formulated as a monotherapy for intravenous administration to the subject in a dosing regimen comprising eight 21-day dosing cycles, wherein:
    (a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and
    (b) the second to eighth dosing cycles each comprises a single dose (C2D1-C8D1) of mosunetuzumab, wherein each single dose C2D1-C8D1 is equivalent in amount to the C1D3,
    wherein the subject is at least 65-years old, and wherein the subject is unfit for treatment with standard R-CHOP therapy.

130. Use of mosunetuzumab in treating a subject having a previously untreated DLBCL, wherein the mosunetuzumab is formulated as a monotherapy for intravenous administration to the subject in a dosing regimen comprising eight 21-day dosing cycles, wherein:
    (a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to eighth dosing cycles each comprises a single dose (C2D1-C8D1) of mosunetuzumab, wherein each single dose C2D1-C8D1 is equivalent in amount to the C1D3,
    wherein the subject is at least 65-years old, and wherein the subject is unfit for treatment with standard R-CHOP therapy.

131. Use of mosunetuzumab in treating a subject having a previously untreated DLBCL, wherein the mosunetuzumab is formulated as a monotherapy for intravenous administration to the subject in a dosing regimen comprising seventeen 21-day dosing cycles, wherein:
    (a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and
    (b) the second to seventeenth dosing cycles each comprises a single dose (C2D1-C17D1) of mosunetuzumab, wherein each single dose C2D1-C17D1 is equivalent in amount to the C1D3,
    wherein the subject is at least 65-years old, and wherein the subject is unfit for treatment with standard R-CHOP therapy.

132. Use of mosunetuzumab in treating a subject having a previously untreated DLBCL, wherein the mosunetuzumab is formulated as a monotherapy for intravenous administration to the subject in a dosing regimen comprising seventeen 21-day dosing cycles, wherein:
    (a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and
    (b) the second to seventeenth dosing cycles each comprises a single dose (C2D1-C17D1) of mosunetuzumab, wherein each single dose C2D1-C17D1 is equivalent in amount to the C1D3,
    wherein the subject is at least 65-years old, and wherein the subject is unfit for treatment with standard R-CHOP therapy.

133. Use of mosunetuzumab in treating an elderly subject having a previously untreated DLBCL, wherein the mosunetuzumab is formulated as a monotherapy for intravenous administration to the subject in a dosing regimen comprising eight 21-day dosing cycles, wherein:
    (a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and
    (b) the second to eighth dosing cycles each comprises a single dose (C2D1-C8D1) of mosunetuzumab, wherein each single dose C2D1-C8D1 is equivalent in amount to the C1D3,
    wherein the subject is at least 80-years old.

134. Use of mosunetuzumab in treating an elderly subject having a previously untreated DLBCL, wherein the mosunetuzumab is formulated as a monotherapy for intravenous administration to the subject in a dosing regimen comprising eight 21-day dosing cycles, wherein:
    (a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to eighth dosing cycles each comprises a single dose (C2D1-C8D1) of mosunetuzumab, wherein each single dose C2D1-C8D1 is equivalent in amount to the C1D3, wherein the subject is at least 80-years old.

135. Use of mosunetuzumab in treating an elderly subject having a previously untreated DLBCL, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to seventeenth dosing cycles each comprises a single dose (C2D1-C17D1) of mosunetuzumab, wherein each single dose C2D1-C17D1 is equivalent in amount to the C1D3, wherein the subject is at least 80-years old.

136. Use of mosunetuzumab in treating an elderly subject having a previously untreated DLBCL, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab, wherein each single dose C2D1-C17D1 is equivalent in amount to the C1D3, wherein the subject is at least 80-years old.

137. Use of mosunetuzumab in treating an unfit subject having a previously untreated DLBCL, wherein the mosunetuzumab is formulated as a monotherapy for intravenous administration to the subject in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab, wherein each single dose C2D1-C8D1 is equivalent in amount to the C1D3, wherein the subject is at least 60-years old, and wherein the subject exhibits:

(i) an impairment in at least ADL component (Katz et al., 1970);

(ii) an impairment in at least one IADL component (Lawton and Brody, 1969);

(iii) an impairment in at least one of cardiac function, vascular function, renal function, and/or liver function; and/or (iv) diabetes.

138. Use of mosunetuzumab in treating an unfit subject having a previously untreated DLBCL, wherein the mosunetuzumab is formulated as a monotherapy for intravenous administration to the subject in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to eighth dosing cycles each comprises a single dose (C2D1-C8D1) of mosunetuzumab, wherein each single dose C2D1-C8D1 is equivalent in amount to the C1D3, wherein the subject is at least 60-years old, and wherein the subject exhibits:

(i) an impairment in at least ADL component;

(ii) an impairment in at least one IADL component;

(iii) an impairment in at least one of cardiac function, vascular function, renal function, and/or liver function; and/or (iv) diabetes.

139. Use of mosunetuzumab in treating an unfit subject having a previously untreated DLBCL, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to seventeenth dosing cycles each comprises a single dose (C2D1-C17D1) of mosunetuzumab, wherein each single dose C2D1-C17D1 is equivalent in amount to the C1D3, wherein the subject is at least 60-years old, and wherein the subject exhibits:

(i) an impairment in at least ADL component;

(ii) an impairment in at least one IADL component;

(iii) an impairment in at least one of cardiac function, vascular function, renal function, and/or liver function; and/or (iv) diabetes.

140. Use of mosunetuzumab in treating an unfit subject having a previously untreated DLBCL, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab, wherein each single dose C2D1-C17D1 is equivalent in amount to the C1D3, wherein the subject is at least 60-years old, and wherein the subject exhibits:

(i) an impairment in at least ADL component;

(ii) an impairment in at least one IADL component;

(iii) an impairment in at least one of cardiac function, vascular function, renal function, and/or liver function; and/or (iv) diabetes.

141. Use of mosunetuzumab in the manufacture of a medicament for treating a subject having a previously untreated B cell proliferative disorder, wherein the mosunetuzumab is formulated as a monotherapy for intravenous administration to the subject in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab, wherein each single dose C2D1-C8D1 is equivalent in amount to the C1D3.

142. Use of mosunetuzumab in the manufacture of a medicament for treating a subject having a previously untreated B cell proliferative disorder, wherein the mosunetuzumab is formulated as a monotherapy for intravenous administration to the subject in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to eighth dosing cycles each comprises a single dose (C2D1-C8D1) of mosunetuzumab, wherein each single dose C2D1-C8D1 is equivalent in amount to the C1D3.

143. Use of mosunetuzumab in the manufacture of a medicament for treating a subject having a previously untreated B cell proliferative disorder, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to seventeenth dosing cycles each comprises a single dose (C2D1-C17D1) of mosunetuzumab, wherein each single dose C2D1-C17D1 is equivalent in amount to the C1D3.

144. Use of mosunetuzumab in the manufacture of a medicament for treating a subject having a previously untreated B cell proliferative disorder, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab, wherein each single dose C2D1-C17D1 is equivalent in amount to the C1D3.

145. Use of mosunetuzumab in the manufacture of a medicament for treating a subject having a previously untreated DLBCL, wherein the mosunetuzumab is formulated as a monotherapy for intravenous administration to the subject in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab, wherein each single dose C2D1-C8D1 is equivalent in amount to the C1D3.

146. Use of mosunetuzumab in the manufacture of a medicament for treating a subject having a previously untreated DLBCL, wherein the mosunetuzumab is formulated as a monotherapy for intravenous administration to the subject in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to eighth dosing cycles each comprises a single dose (C2D1-C8D1) of mosunetuzumab, wherein each single dose C2D1-C8D1 is equivalent in amount to the C1D3.

147. Use of mosunetuzumab in the manufacture of a medicament for treating a subject having a previously untreated DLBCL, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to seventeenth dosing cycles each comprises a single dose (C2D1-C17D1) of mosunetuzumab, wherein each single dose C2D1-C17D1 is equivalent in amount to the C1D3.

148. Use of mosunetuzumab in the manufacture of a medicament for treating a subject having a previously untreated DLBCL, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab, wherein each single dose C2D1-C17D1 is equivalent in amount to the C1D3.

149. Use of mosunetuzumab in the manufacture of a medicament for treating a subject having a previously untreated DLBCL, wherein the mosunetuzumab is formulated as a monotherapy for intravenous administration to the subject in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab, wherein each single dose C2D1-C8D1 is equivalent in amount to the C1D3, wherein the subject is at least 65-years old, and wherein the subject is unfit for treatment with standard R-CHOP therapy.

150. Use of mosunetuzumab in the manufacture of a medicament for treating a subject having a previously untreated DLBCL, wherein the mosunetuzumab is formulated as a monotherapy for intravenous administration to the subject in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to eighth dosing cycles each comprises a single dose (C2D1-C8D1) of mosunetuzumab, wherein each single dose C2D1-C8D1 is equivalent in amount to the C1D3, wherein the subject is at least 65-years old, and wherein the subject is unfit for treatment with standard R-CHOP therapy.

151. Use of mosunetuzumab in the manufacture of a medicament for treating a subject having a previously untreated DLBCL, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to seventeenth dosing cycles each comprises a single dose (C2D1-C17D1) of mosunetuzumab, wherein each single dose C2D1-C17D1 is equivalent in amount to the C1D3, wherein the subject is at least 65-years old, and wherein the subject is unfit for treatment with standard R-CHOP therapy.

152. Use of mosunetuzumab in the manufacture of a medicament for treating a subject having a previously untreated DLBCL, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab, wherein each single dose C2D1-C17D1 is equivalent in amount to the C1D3, wherein the subject is at least 65-years old, and wherein the subject is unfit for treatment with standard R-CHOP therapy.

153. Use of mosunetuzumab in the manufacture of a medicament for treating an elderly subject having a previously untreated DLBCL, wherein the mosunetuzumab is formulated as a monotherapy for intravenous administration to the subject in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab, wherein each single dose C2D1-C8D1 is equivalent in amount to the C1D3, wherein the subject is at least 80-years old.

154. Use of mosunetuzumab in the manufacture of a medicament for treating an elderly subject having a previously untreated DLBCL, wherein the mosunetuzumab is formulated as a monotherapy for intravenous administration to the subject in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to eighth dosing cycles each comprises a single dose (C2D1-C8D1) of mosunetuzumab, wherein each single dose C2D1-C8D1 is equivalent in amount to the C1D3, wherein the subject is at least 80-years old.

155. Use of mosunetuzumab in the manufacture of a medicament for treating an elderly subject having a previously untreated DLBCL, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to seventeenth dosing cycles each comprises a single dose (C2D1-C17D1) of mosunetuzumab, wherein each single dose C2D1-C17D1 is equivalent in amount to the C1D3, wherein the subject is at least 80-years old.

156. Use of mosunetuzumab in the manufacture of a medicament for treating an elderly subject having a previously untreated DLBCL, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab, wherein each single dose C2D1-C17D1 is equivalent in amount to the C1D3, wherein the subject is at least 80-years old.

157. Use of mosunetuzumab in the manufacture of a medicament for treating an unfit subject having a previously untreated DLBCL, wherein the mosunetuzumab is formulated as a monotherapy for intravenous administration to the subject in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to eighth dosing cycles each comprises a single dose (C2D1-C8D1) of mosunetuzumab, wherein each single dose C2D1-C8D1 is equivalent in amount to the C1D3, wherein the subject is at least 60-years old, and wherein the subject exhibits:

(i) an impairment in at least ADL component (Katz et al., 1970);

(ii) an impairment in at least one IADL component (Lawton and Brody, 1969);

(iii) an impairment in at least one of cardiac function, vascular function, renal function, and/or liver function; and/or (iv) diabetes.

158. Use of mosunetuzumab in the manufacture of a medicament for treating an unfit subject having a previously untreated DLBCL, wherein the mosunetuzumab is formulated as a monotherapy for intravenous administration to the subject in a dosing regimen comprising eight 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to eighth dosing cycles each comprises a single dose (C2D1-C8D1) of mosunetuzumab, wherein each single dose C2D1-C8D1 is equivalent in amount to the C1D3, wherein the subject is at least 60-years old, and wherein the subject exhibits:

(i) an impairment in at least ADL component;

(ii) an impairment in at least one IADL component;

(iii) an impairment in at least one of cardiac function, vascular function, renal function, and/or liver function; and/or (iv) diabetes.

159. Use of mosunetuzumab in the manufacture of a medicament for treating an unfit subject having a previously untreated DLBCL, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 13.5 mg; and (b) the second to seventeenth dosing cycles each comprises a single dose (C2D1-C17D1) of mosunetuzumab, wherein each single dose C2D1-C17D1 is equivalent in amount to the C1D3, wherein the subject is at least 60-years old, and wherein the subject exhibits:

(i) an impairment in at least ADL component;

(ii) an impairment in at least one IADL component;

(iii) an impairment in at least one of cardiac function, vascular function, renal function, and/or liver function; and/or (iv) diabetes.

160. Use of mosunetuzumab in the manufacture of a medicament for treating an unfit subject having a previously untreated DLBCL, wherein the mosunetuzumab is formulated as a monotherapy for intravenous administration to the subject in a dosing regimen comprising seventeen 21-day dosing cycles, wherein:

(a) the first dosing cycle comprises a first dose (C1D1), a second dose (C1D2), and a third dose (C1D3) of mosunetuzumab, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab, wherein each single dose C2D1-C17D1 is equivalent in amount to the C1D3, wherein the subject is at least 60-years old, and wherein the subject exhibits:

(i) an impairment in at least ADL component;

(ii) an impairment in at least one IADL component;

(iii) an impairment in at least one of cardiac function, vascular function, renal function, and/or liver function; and/or (iv) diabetes.

161. The method, mosunetuzumab for use, or use of any one of embodiments 1-160, wherein the subject is human.

VII. EXAMPLES

The following are examples of methods and compositions of the invention. It is understood that various other embodiments may be practiced, given the general description provided above.

Example 1. A Phase I/II Trial of Mosunetuzumab (BTCT4465A) as Monotherapy in Elderly/Unfit Patients with Previously Untreated Diffuse Large B-Cell Lymphoma A. Objectives This Phase I/II, multicenter, open-label study evaluates the safety, pharmacokinetics, and preliminary efficacy of mosunetuzumab in elderly/unfit patients with previously untreated DLBCL. Subjects of the study complete two safety evaluations with approximately 6 patients in each cohort, to clear the recommended dose. The specific objectives and endpoints are listed below in Table 4.

TABLE 4

| Safety, Pharmacokinetic, and Efficacy Objectives | |
| --- | --- |
| Safety Objectives | Corresponding Endpoints |
| To evaluate the safety and tolerability of mosunetuzumab in elderly/unfit patients with previously untreated DLBCL | Occurrence and severity of adverse events including DLTs (Cohort A only), with severity determined according to NCI ® CTCAE v5.0; for CRS, severity determined according to the ASTCT ® CRS Consensus Grading Change from baseline in targeted vital signs Change from baseline in targeted clinical laboratory test results |
| Pharmacokinetic Objectives | Correspinding Endpoints |
| To characterize the pharmacokinetics of mosunetuzumab when administered in the absence of prior rituximab-containing therapy | $C_{max}$ $C_{min}$ Total exposure (AUC), clearance, and volume of distribution, as estimated by population PK modeling, as appropriate and supported by data |

TABLE 4-continued

| Safety, Pharmacokinetic, and Efficacy Objectives | |
|---|---|
| Exploratory Pharmacokinetic Objectives | Correspinding Endpoints |
| To characterize the relationship between serum pharmacokinetics, safety, biomarkers, and efficacy | Relationship between serum pharmacokinetics and safety, biomarkers, or efficacy endpoints, as appropriate |
| Primary Efficacy Objectives | Corresponding Endpoint |
| To make a preliminary assessment of anti-tumor activity of mosunetuzumab in elderly/unfit patients with previously untreated DLBCL | PET-CT CR rate, defined as the proportion of patients with CR according to the Lugano 2014 criteria at PRA as determined by the investigator |
| Secondary Efficacy Objective | Corresponding Endpoints |
| To make a preliminary assessment of efficacy of mosunetuzumab as a single agent sing measures other than PET-CT CR rate | All radiographic assessments are according to the Lugano 2014 criteria. ORR, defined as the proportion of patients with a CR or PR, at PRA based on PET-CT as determined by the investigator Best ORR (CR or PR at any time) during the study, based on PET-CT and/or CT scans as determined by the investigator DOR, defined as the time from the first occurrence of a documented objective response (CR or PR) to disease progression or relapse, or death from any cause, whichever occurs first, as determined by the investigator PFS, defined as the time from the first study treatment to the first occurrence of disease progression or relapse, or death from any cause, whichever occurs first, as determined by the investigator OS, defined as the time from first study treatment to death from any cause Time to deterioration in physical functioning according to the EORTC QLQ-C30 and EORTC IL17; time to deterioration in fatigue as per the EORTC-QLQ-C30; and time to deterioration in lymphoma symptoms according to the FACT-Lym subscale Proportion of patients achieving a clinically meaningful improvement in physical functioning as measured by EORTC QLQ-C30 and EORTC IL17 |
| Exploratory Efficacy Objective | Corresponding Endpoints |
| To make a preliminary assessment of efficacy of mosunetuzumab as a single agent using EORTC QLQ-C30, EORTC IL17 | Proportion of patients reporting treatment-related symptoms according to EORTC QLQ-C30 All remaining scales of the EORTC QLQ-C30 and the EORTC IL17 |
| Immunogenicity Objectives | Corresponding Endpoints |
| To assess the immune response to mosunetuzumab To assess the potential effect of mosunetuzumab ADA incidence on relevant clinical outcomes | To assess the incidence of ADAs to mosunetuzumab as single agent Relationship between ADAs and pharmacokinetics, safety, efficacy, and biomarkers may be explored as appropriate |
| Exploratory Biomarker Objectives | Corresponding Endpoints |
| To identify biomarkers that are predictive of response to mosunetuzumab single agent, are associated with progression to a more severe disease state (i.e., prognostic biomarkers), are associated with acquired resistance to mosunetuzumab single agent, are associated with susceptibility to developing adverse events, can provide evidence of mosunetuzumab activity, or can increase the knowledge and understanding of disease biology To make a preliminary assessment of response to mosunetuzumab single agent in different clinical and biologic prognostic subgroups of NHL | Relationship between exploratory biomarkers (including cytokines, T-cell and B-cell counts, and T-cell activation) and efficacy, safety, PK, immunogenicity, or other biomarker endpoints Association between prognostic subtypes, exploratory biomarkers, and PET-CT CR, ORR, DOR, and PFS endpoints Relationship over time between ctDNA and tumor burden as measured by imaging |

TABLE 4-continued

| Safety, Pharmacokinetic, and Efficacy Objectives |
|---|
| To make a preliminary assessment of MRD status following mosunetuzumab single agent |

ADA = anti-drug antibody;
ADL = activities of daily living;
AUC = area under the concentration-time curve;
ASTCT ® = American Society for Transplantation and Cellular Therapy ®;
CCI = Charlson Comorbidity Index;
$C_{max}$ = maximum serum concentration;
$C_{min}$ = minimum serum concentration;
CR = complete response;
CRS = cytokine release syndrome;
CT = computed tomography (scan);
ctDNA = circulating tumor DNA;
DLBCL = diffuse large B-cell lymphoma;
DOR = duration of response;
EORTC IL17 = European Organization for Research and Treatment of Cancer Item Library;
EORTC QLQ-C30 = European Organization for Research and Treatment of Cancer Quality of Life Questionnaire Core 30;
FACT-Lym = Functional Assessment of Cancer Therapy-Lymphoma;
HRQoL = health-related quality of life;
IADL = instrumental activities of daily living;
IRC = Independent Review Committee;
MNA ®-SF = Mini Nutritional Assessment-Short Form;
MRD = minimal residual disease;
NALT = new anti-lymphoma therapy;
NCI ® CTCAE v5.0 = National Cancer Institute Common Terminology Criteria for Adverse Events, Version 5.0;
NHL = non-Hodgkin's lymphoma;
ORR = objective response rate;
PET-CT = positron emission tomography-computed tomography (scan);
PFS = progression-free survival;
PK = pharmacokinetic
PRA = primary response assessment;
PRO = patient-reported outcome;
$T_{max}$ = time to maximum concentration.
"Lugano 2014 criteria" refers to Lugano Response Criteria for Malignant Lymphoma (Cheson et al. 2014).
PRA is 6 to 8 weeks after C8D1 or final dose of study treatment.

B. Study Design

Figure 1:
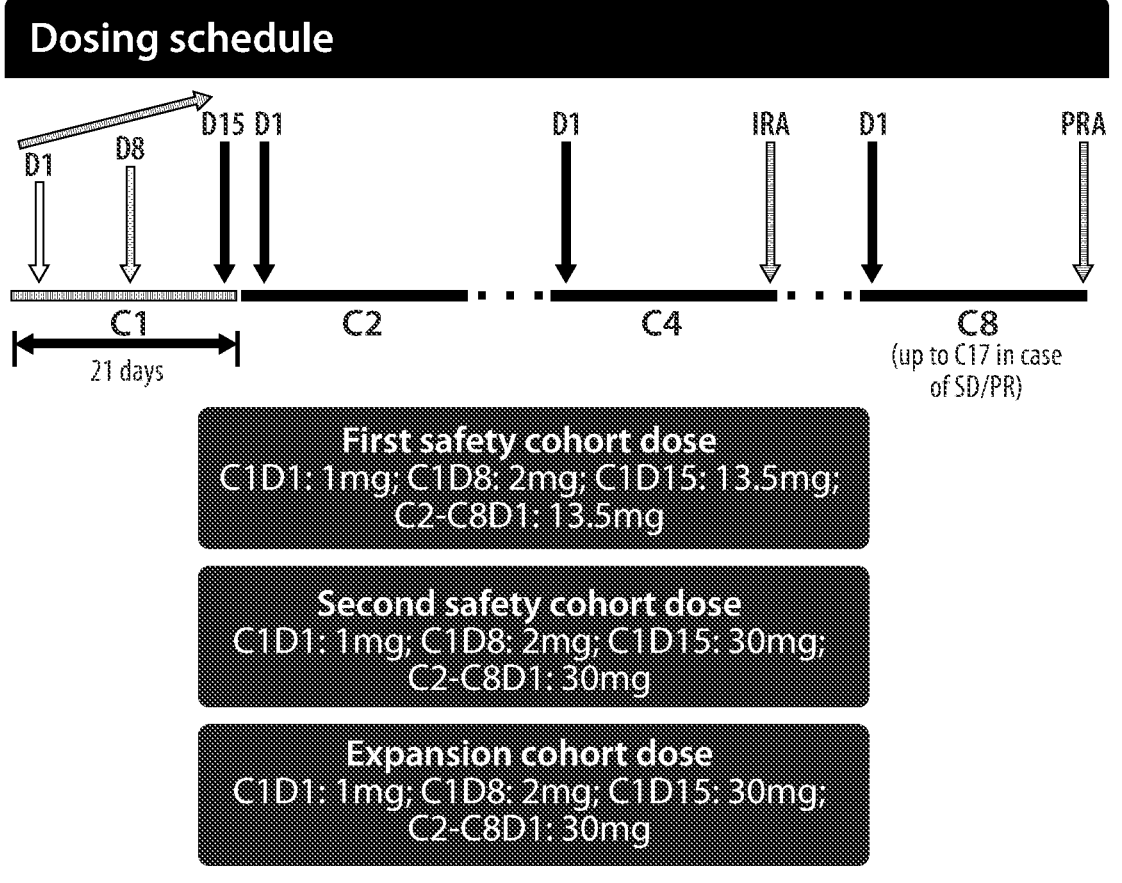
FIG. 1 is a schematic describing the overview of the dosing schedule of the study described in Example 1.

This is a Phase I/I1 study to assess mosunetuzumab as a monotherapy in elderly/unfit patients with previously untreated DLBCL that receive mosunetuzumab intravenously (IV). See FIG. 1 for an overview of the study design. Approximately 52 patients are enrolled.

A safety cohort of approximately 6 patients with previously untreated DLBCL receive mosunetuzumab to assess safety and tolerability of this regimen in the front-line setting at the 13.5 mg dose (1 mg on Day 1 of Cycle 1 (Cycle 1 Dose 1; C1D1); 2 mg on Day 8 of Cycle 1 (Cycle 1 Dose 2; C1D2); 13.5 mg on Day 15 of Cycle 1 (Cycle 1 Dose 3; C1D3). An IMC review takes place after all patients have completed 1 cycle of treatment. If mosunetuzumab is determined to be safe at the 13.5 mg dose, the internal monitoring committee (IMC) can recommend dose escalation to enroll an additional approximately 6 patients at the 30 mg target dose. An additional IMC review takes place after these patients have been evaluated for at least 1 cycle. Upon recommendation by the IMC, an additional approximately 40 patients are enrolled in the expansion stage at the recommended dose (RD). Patients with a response of SD or PR after 8 cycles may continue with mosunetuzumab treatment for up to 17 cycles or until disease progression. After 8 (or 17) cycles of treatment, patients with CR are in follow up. In those patients, at the time of disease progression, patients may receive re-treatment with an additional 8 cycles of mosunetuzumab. Patients undergo interim response assessment (IRA) between Cycles 4 and 5, and undergo primary response assessment (PRA) after Cycle 8.

After PRA, patients continue to be evaluated every 6 months (±2 weeks) by positron emission tomography-computed tomography (PET-CT) scan at the first 6 month post primary response assessment (PRA) visit, and then by computed tomography (CT) scan with or without PET-CT scan during follow-up for 2 years after PRA until disease progression, death, or withdrawal of consent. Tumor assessments should also be performed to confirm clinical suspicion of disease progression.

Study enrollment takes place in two stages: safety-evaluation stage at 2 dose levels followed by an expansion stage. Initially, the patients receive 8 cycles of mosunetuzumab in 21-day cycles. See Additionally, patients with disease progression after achieving a CR after 8 cycles may be re-treated with additional 8 cycles of mosunetuzumab. If patients are re-treated after more than 6 weeks following their previous dose of mosunetuzumab, patients must receive a new step-up load dosing schedule in their re-treatment, in a similar dosing regimen to their first dosing cycle. Additional details on re-treatment is provided below.
Safety-Evaluation Stages (First Approximately 12 Patients)

Experience with mosunetuzumab to date includes patients who have received prior treatment(s), typically including CD20-directed treatments, while the current study enrolls patients with previously untreated DLBCL. Differences in baseline characteristics, including peripheral B- and T-cell numbers, tumor volume, and comorbidities, in study patients compared with prior patients evaluated in Study G029781 (ClinicalTrials.gov Identifier: NCT02500407) may result in differences in the kinetics of T-cell activation and associated safety profile. Therefore, the safety of mosunetuzumab is initially assessed in this study for 1 cycle in approximately 6 patients with previously untreated DLBCL at each dose level to confirm this regimen has acceptable safety in this patient population through the following measures:

Enrollment into this study is staggered such that there is at least 72 hours between each patient enrolled in the safety-evaluation stages and administration of the first dose of mosunetuzumab to assess for any severe and unexpected acute drug or infusion-related toxicities. The Sponsor must receive confirmation on the status of the prior patient before the next patient receives mosunetuzumab.

In each safety cohort, enrollment is paused after 6 patients, until all 6 patients have received Cycle 1 step-up doses of mosunetuzumab and the 21-day safety evaluation stage has been completed. Patients who withdraw prior to 21 days are replaced.

Inpatient monitoring is required, and the mandatory hospitalization is for at least 24 hours following the first mosunetuzumab dose in Cycle 1 (1 mg on Day 1).

Pre-phase treatment with prednisone 100 mg daily for 7 days immediately preceding Day 1 of Cycle 1 of study treatment and vincristine 1 mg are allowed in this study per investigator discretion and per local standard of care (SOC).

An IMC reviews the all patients who have completed the safety evaluation stage(s) prior to making recommendations for the expansion stage.

After IMC review of the safety-evaluation stage, if no unmanageable or unexpected acute and severe toxicities are identified, subsequent patients in the expansion stage are staggered such that their C1D1 treatments are administered ≥24 hours apart.

If the frequency (e.g., ≥2 out of 6 patients) of Grade 3 or higher toxicities or other unacceptable toxicities in the safety cohort suggest that the dose level is not tolerable for patients with previously untreated DLBCL, accrual to this cohort is halted. Consideration is then given to enrolling patients with one or more of the following modifications:

If acute toxicity is generally observed before the first mosunetuzumab C1D15 dose (i.e., after 1-mg infusion given on Day 1 of Cycle 1 (C1D1) or 2-mg infusion on Day 8 of Cycle 1 (C1D2)), the following adjustments to dose schedule and/or other mitigation strategies may be tested, including:

Mandating pre-phase treatment with prednisone 100 mg daily for 7 days immediately preceding C1D1 of study treatment This modification is prioritized, as it is consistent with recommendations for patients with DLBCL at risk for early treatment related toxicities with R-CHOP treatment (Pfreundschuh et al. 2010; Tilly et al. 2015).

Pretreatment with 1 mg vincristine on Day 1 of pre-phase and prednisone 100 mg daily for 7 days immediately preceding Day 1 of Cycle 1 of study treatment If toxicity generally occurs after the C1D3 mosunetuzumab dose on Day 15 of Cycle 1:

Reduction of mosunetuzumab to a dose level ≥25% lower (e.g., 9 mg) than initially tested may be evaluated in an additional cohort of 3 to 6 patients. If this dose level is again not tolerable, further C1D15 dose reductions of ≥25% of the preceding C1D15 dose may be assessed in subsequent cohorts of 3-6 patients.

Expansion Stage

If the mosunetuzumab dose and schedule is well tolerated at 30 mg in the second safety evaluation stage, the dose schedule recommended by the IMC is then tested in an additional approximately 40 patient dose expansion cohort in patients with previously untreated DLBCL who are unfit to receive full-dose chemotherapy (same patient population as in the safety-evaluation stage).

No intra-patient dose escalation is permitted in this study cohort. Initially, patients receive 8 cycles of mosunetuzumab in 21-day cycles. See below for additional details and information for the continuation of mosunetuzumab.

Continuation of Mosunetuzumab IV in Case of Partial Response or Stable Disease at Primary Response Assessment (PRA)

Patients with response of SD or PR are eligible to receive additional doses of mosunetuzumab IV (up to 9 additional cycles, for a total of 17 cycles) at the dose level that was demonstrated to be safe in the safety evaluation, as determined by the IMC, provided that they meet the following criteria for acceptable toxicity and ongoing clinical benefit:

Acceptable toxicity: All adverse events experienced with prior infusions that were not attributed to constitutional symptoms of the patient's cancer or intercurrent illness must have decreased to Grade 1 or baseline grade on or before the day of the next infusion. Exceptions on the basis of ongoing clinical benefit may be allowed after a careful assessment and discussion of benefit versus risk with the patient by the investigator and approval from the Medical Monitor. In addition, delay of therapy because of toxicities not attributed to study drug may not require discontinuation from the study but must be approved by the Medical Monitor.

Ongoing clinical benefit: Patients must demonstrate improvement/stabilization in tumor burden, according to the Lugano 2014 Criteria or demonstrate clinical signs or symptoms of benefit, as judged by the investigator, independent of the radiographic assessment (per the Lugano 2014 criteria).

Re-Treatment with Mosunetuzumab IV in case of Disease Progression after Complete Response Based on results from Study GO29781 (ClinicalTrials.gov Identifier: NCT02500407), patients who experience disease recurrence after achieving a response of CR to mosunetuzumab after 8 cycles of mosunetuzumab dosing may benefit from additional cycles of study treatment. Therefore, these patients may be re-treated with an additional 8 cycles of mosunetuzumab (8 cycles+8 cycles). The 8 cycles of the re-treatment dosing regimen (Cycles 9-16) mirror the 8 cycles of the initial mosunetuzumab treatment, including a step-up dosing cycle during Cycle 1 of retreatment (1 mg on Day 1 of Cycle 9 (Cycle 9 Dose 1; C9D1); 2 mg on Day 8 of Cycle 9 (Cycle 9 Dose 2; C9D2); 13.5 or 30 mg on Day 15 of Cycle 9 (Cycle 9 Dose 3; C9D3).

The study re-treatment dose and schedule is determined based on what was previously demonstrated to be safe in the safety evaluation, as determined by the IMC.

Patients may be eligible to receive re-treated with an additional 8 cycles of mosunetuzumab, provided the following criteria are met:

Written informed consent to acknowledge patient deferral of any standard treatment options that may exist in favor of reinitiating study treatment. Written informed consent is provided to acknowledge to undergoing a biopsy of recurrent or progressing tumor tissue, if clinically feasible.

No intervening systemic anti-cancer therapy administered between the completion of initial study treatment and re-initiation of study treatment.

Pertinent eligibility criteria must be met at the time that mosunetuzumab treatment is re-initiated, with the following exceptions:

Prior therapy with mosunetuzumab is allowed.

Manageable and reversible immune-related adverse events with initial study treatment are allowed and do not constitute an exclusionary history of autoimmune disease.

Serology tests to demonstrate HIV, hepatitis C virus (HCV), and hepatitis B virus (HBV) status do not need to be repeated unless clinically indicated. EBV and cytomegalovirus (CMV) quantitative polymerase chain reaction (PCR) must be repeated.

Patients may require hospitalization following the first re-treatment administration. The need for hospitalization following the first re treatment administration is made in consultation with study investigators.

Patients who experienced Grade 2 or Grade 3 adverse events that were not considered by the investigator to be attributable to another clearly identifiable cause during initial treatment, must have resolved these toxicities to Grade<1.

Patients must not have experienced Grade 4 non-hematologic adverse events that were not considered by the investigator to be attributable to another clearly identifiable cause during initial study treatment, with the possible exception of tumor lysis syndrome (TLS) and CRS.

Following disease progression, patients proceeding to re-treatment are strongly encouraged to undergo a repeat tumor biopsy from a safely accessible site to assess: 1) CD20 expression status and 2) changes/status of the tumor and immune microenvironment.

End of Study and Length of Study

The end of this study is defined as the date when the last patient, last visit occurs, including survival follow-up visits conducted by telephone or on-site visits. The end of the study is approximately 30 months after the last patient is enrolled to allow all patients to have up to 2 years of follow-up after the PRA.

The total length of the study, from screening of the first patient to the end of the study, is approximately 75 months.

In addition, the Sponsor may decide to terminate the study at any time.

Mosunetuzumab IV Dose and Schedule

Mosunetuzumab is administered intravenously on a 21-day cycle with pre-medications (steroids, anti-pyretic, anti-histamines as described herein) and on a Cycle 1 step-up dose schedule (see FIG. 1) to mitigate the risk of acute toxicities (e.g., CRS, TLS, CNS toxicity). Using the Cycle 1 step-up dose schedule, the overall safety profile of mosunetuzumab has been manageable, and the MTD has not been exceeded to date.

The starting dose for mosunetuzumab in this study is 1 mg (Day 1 of Cycle 1; C1D1) and 2 mg (Day 8 of Cycle 1; C1D2). The dose is 13.5 mg on Day 15 of Cycle 1 (C1D3), followed by 13.5 mg on Day 1 of all subsequent 21-day cycles (CXD1) of mosunetuzumab treatment in the first safety-evaluation phase, and 30 mg on Day 15 of Cycle 1 (C1D3) and on Day 1 of all subsequent cycles (CXD1) in the second safety-evaluation phase. Expansion dose is determined upon recommendation by the IMC after review of safety data.

Administration of mosunetuzumab may be continued after completion of 8 cycles of treatment in patients who have either a response of SD or PR at the end of the induction treatment for up to an additional 9 cycles or progression of disease, whichever occurs first (see above section on Continuation of Mosunetuzumab). Additionally, patients who achieved a CR after 8 cycles of mosunetuzumab and had disease progression during the follow-up period may receive re treatment with an additional 8 cycles of mosunetuzumab, or until progression of disease (see above section on Re-Treatment of Mosunetuzumab). After the primary response assessment (PRA) if more than 6 weeks elapsed after their final dose of mosunetuzumab (e.g., in the case of re-treatment), patients eligible for continued treatment have mosunetuzumab administered as step up doses on C9D1, C9D2, and C9D3 on Days 1, 8, and 15, respectively, of Cycle 9 (i.e., first cycle of re-treatment).

C. Inclusion Criteria

Patients meet the following criteria for study entry:

Signed Informed Consent Form(s)

Age≥18 years at time of signing Informed Consent Form (s)

At least one bi-dimensionally measurable nodal lesion, defined as >1.5 cm in its longest dimension, or one bi-dimensionally measurable extranodal lesion, defined as >1.0 cm in its longest diameter.

Ability and willingness to comply with the study protocol procedures, in the investigator's judgment Confirmed availability of archival tumor tissue before study enrollment:

The specimen must have an associated pathology report.

The specimen must contain adequate evaluable tumor cells (>20% for excisional biopsy and >50% for core biopsy).

Formalin-fixed, paraffin-embedded tissue blocks are preferred over slides. For core biopsies, it is recommended that 3-5 cores are aligned and embedded into a single block. Tissue blocks that are not formalin-fixed are accepted in countries that use a fixative other than paraformaldehyde, but information on the type of fixative should be included. If a tissue block is not available, a minimum of 20 serial, freshly cut, unstained slides may be sent. Tumor tissue from bone metastases that have been decalcified is not acceptable.

For samples that do not meet the minimum requirements for size or slide number, contact the Medical Monitor via site contact with tissue size, tumor content, and number of slides to determine eligibility.

The sample should be shipped according to instructions provided in the laboratory manual.

Bone marrow aspirates collected as part of optional study assessments do not need to be sent to the central laboratory; however, the associated hematopathology report should be submitted when available.

If archival tissue is unavailable or is determined to be unsuitable for required testing, tumor tissue must be obtained from a biopsy performed at screening. For patients who have inadequate or inaccessible tumor tissue for biopsy, the patient may still be eligible for the study after Medical Monitor approval has been obtained.

Life expectancy of at least 24 weeks

Adequate hematologic function (unless inadequate function is due to underlying disease, as established by extensive bone marrow involvement or is due to hypersplenism secondary to the involvement of the spleen by lymphoma per the investigator) defined as follows:

Hemoglobin≥9 g/dL

ANC≥1.0×10⁹/L

Platelet count≥75×10⁹/L

ECOG Performance Status of 0, 1, or 2; or an ECOG Performance Status of 3 after discussion with and approval from the Medical Monitor (see Table 5 below)

Previously untreated, histologically confirmed DLBCL according to WHO 2016 classification (pathology report must provide WHO 2016 diagnosis) expected to express the CD20 antigen (Swerdlow et al. 2016). Exception: diagnosis of primary mediastinal DLBCL Age≥80 years, or age 60-79 years with at least one of the following:

Impairment in at least one ADL component (Katz et al. 1970)

Impairment in at least one IADL component (Lawton and Brody 1969)

Impairment in cardiac function, renal function, or liver function such that the patient is unfit for full-dose immunochemotherapy, such as R-CHOP Adequate end-organ function:

Pulmonary function: no significant pulmonary comorbidities (e.g., severe chronic obstructive pulmonary disease [COPD])

Cardiac function: left ventricular ejection fraction (LVEF)≥40%

Renal function: creatinine clearance ≥40 mL/min. Exceptions may be made for patients with creatinine clearance <40 mL/min, provided creatinine is within normal range and after discussion with and approval from the Medical Monitor.

For men: agreement to remain abstinent (refrain from heterosexual intercourse) or use a condom, and agreement to refrain from donating sperm, as defined below:

With a female partner of childbearing potential or pregnant female partner, men must remain abstinent or use a condom during the treatment period and for 60 days after the final dose of mosunetuzumab, 60 days after the final dose of tocilizumab, as applicable, to avoid exposing the embryo. Men must refrain from donating sperm during this same period. The reliability of sexual abstinence should be evaluated in relation to the duration of the clinical trial and the preferred and usual lifestyle of the patient. Periodic abstinence (e.g., calendar, ovulation, symptothermal, or post-ovulation methods) and withdrawal are not acceptable methods of preventing drug exposure.

TABLE 5

| ECOG Performance Status Scale | |
| --- | --- |
| Grade | Description |
| 0 | Fully active; able to carry on all pre-disease performance without restriction. |
| 1 | Restricted in physically strenuous activity but ambulatory and able to carry out work of a light or sedentary nature (e.g., light housework or office work). |
| 2 | Ambulatory and capable of all self-care but unable to carry out any work activities. Up and about >50% of waking hours. |
| 3 | Capable of only limited self-care; confined to a bed or chair >50% of waking hours. |
| 4 | Completely disabled. Cannot carry on any self-care. Totally confined to bed or chair. |
| 5 | Dead. |

D. Exclusion Criteria

Patients meet any of the following criteria are excluded from the study:

Prior treatment for DLBCL with chemotherapy, immunotherapy, and biologic therapy. Exception: patients who are treated with vincristine and prednisone as part of pre-phase treatment Transformed lymphoma CNS lymphoma Prior treatment with mosunetuzumab Prior stem cell transplant (autologous and allogeneic)

History of severe allergic or anaphylactic reactions to humanized or murine monoclonal antibodies or known sensitivity or allergy to murine products History of confirmed progressive multifocal leukoencephalopathy (PML)

Known or suspected chronic active Epstein-Barr virus (CAEBV) infection

Patients with history of hemophagocytic lymphohistiocytosis (HLH)

Positive test results for chronic hepatitis B infection (defined as positive hepatitis B surface antigen (HBsAg) serology)

Patients with occult or prior hepatitis B infection (defined as positive total hepatitis B core antibody (HBcAb) and negative HBsAg) may be included if HBV DNA is undetectable at the time of screening. These patients must be willing to undergo monthly DNA testing and appropriate antiviral therapy as indicated.

Acute or Chronic HCV Infection

Patients who are positive for HCV antibody must be negative for HCV by PCR.

HIV seropositivity

Administration of a live, attenuated vaccine within 4 weeks before first mosunetuzumab administration or anticipation that such a live, attenuated vaccine is required during the study Live vaccines should be avoided during study treatment and after the last study treatment until B-cell recovery to normal ranges.

Influenza vaccination should be given during influenza season only. Patients must not receive live, attenuated influenza vaccine (e.g., FLUMIST®) at any time during the study treatment period.

Investigators should review the vaccination status of potential study patients being considered for this study and follow the U.S. Centers for Disease Control and Prevention guidelines for adult vaccination or similar national guidelines with any other non-live vaccines intended to prevent infectious diseases prior to study.

Prior solid organ transplantation

History of autoimmune disease, including, but not limited to myasthenia gravis, myositis, autoimmune hepatitis, systemic lupus erythematosus, rheumatoid arthritis, inflammatory bowel disease, vascular thrombosis associated with anti-phospholipid syndrome, Wegener granulomatosis, Sjogren syndrome, Guillain-Barré syndrome, multiple sclerosis, vasculitis, or glomerulonephritis Exceptions may be made for patients with a remote history of or well controlled autoimmune disease, excluding patients on systemic immunosuppression for autoimmune disease, or patients who received such immunosuppression within 1 year prior. Patients with a history of autoimmune-related hypothyroidism on a stable dose of thyroid replacement hormone may be eligible for this study.

Patients with controlled Type 1 diabetes mellitus who are on a stable insulin regimen are eligible for the study.

Patients with a history of disease-related immune thrombocytopenic purpura or autoimmune hemolytic anemia may be eligible after review and approval by the Medical Monitor.

Patients with eczema, psoriasis, lichen simplex chronicus, or vitiligo with dermatologic manifestations only (e.g., patients with psoriatic arthritis are excluded) are eligible for the study provided all of following conditions are met:

Rash must cover <10% of body surface area.

Disease is well controlled at baseline and requires only low-potency topical corticosteroids.

No occurrence of acute exacerbations of the underlying condition requiring psoralen plus ultraviolet A radiation, methotrexate, retinoids, biologic agents, oral calcineurin inhibitors, or high potency oral corticosteroids within the previous 12 months.

Received systemic immunosuppressive medications (including, but not limited to, cyclophosphamide, azathioprine, methotrexate, thalidomide, and anti-tumor necrosis factor agents) with the exception of corticosteroid treatment ≤10 mg/day prednisone or equivalent within 2 weeks prior to the first dose of mosunetuzumab and with the exception of patients treated with pre-phase prednisone and pre-phase vincristine in Cohort B Patients who received acute, low-dose, systemic immunosuppressant medications (e.g., single dose of dexamethasone for nausea or B-symptoms) may be enrolled in the study after discussion with and with the approval of the Medical Monitor.

The use of inhaled corticosteroids is permitted.

The use of mineralocorticoids for management of orthostatic hypotension is permitted.

The use of physiologic doses of corticosteroids for management of adrenal insufficiency is permitted.

Current or past history of CNS disease, such as stroke, epilepsy, CNS vasculitis, or neurodegenerative disease Patients with a history of stroke who have not experienced a stroke or transient ischemic attack in the past 2 years and have no significant residual neurologic deficits as judged by the investigator are allowed.

Patients with a history of epilepsy who have had no seizures in the past 2 years while not receiving any anti-epileptic medications are allowed in the expansion cohorts only.

History of other malignancy that could affect compliance with the protocol or interpretation of results Patients with a history of curatively treated basal or squamous cell carcinoma or melanoma of the skin or in situ carcinoma of the cervix, or early-stage localized prostate cancer (Gleason score≤6 or below, Stage I or II) with no requirement for therapy at any time prior to study are eligible.

Patients with a malignancy that has been treated with curative intent are also excluded unless the malignancy has been in documented remission without treatment for ≥2 years before enrollment. Exception are made for patients with history of breast cancer that is estrogen receptor-/progesterone receptor-positive for more than 2 years before enrollment who are treated with adjuvant hormonal therapy.

Evidence of significant, uncontrolled concomitant diseases that could affect compliance with the protocol or interpretation of results or that could increase risk to the patient Known active bacterial, viral, fungal, mycobacterial, parasitic, or other infection (excluding fungal infections of nail beds) at study enrollment or any major episode of infection requiring treatment with IV antibiotics or hospitalization (relating to the completion of the course of antibiotics) within 4 weeks before C1D1

Clinically significant history of liver disease, including viral or other hepatitis, current alcohol abuse, or cirrhosis Recent major surgery within 4 weeks before the start of C1D1, other than superficial lymph node biopsies for diagnosis Any of the following abnormal laboratory values within 14 days of initiation of study treatment:

AST or ALT>3×ULN

Total bilirubin≥2×ULN

Patients with a documented history of Gilbert syndrome and in whom total bilirubin elevations are accompanied by elevated indirect bilirubin are eligible.

INR>1.5×ULN in the absence of therapeutic anticoagulation

PTT or aPTT>1.5×ULN in the absence of a lupus anticoagulant or therapeutic anticoagulant Prior treatment with radiotherapy within 2 weeks prior to C1D1. If patients have received radiotherapy within 4 weeks prior to the initiation of study treatment, patients must have at least one measurable lesion outside of the radiation field.

Patients who have only one measurable lesion that was previously irradiated but subsequently progressed are eligible.

Adverse events from prior anti-cancer therapy not resolved to ≤Grade 1 (with the exception of alopecia, anorexia, nausea, vomiting, and fatigue)

Grade 2 toxicities that are manageable and improving may be allowed following approval of the Medical Monitor.

Significant cardiovascular disease (such as New York Heart Association Class III or IV cardiac disease, congestive heart failure, myocardial infarction within the previous 6 months, unstable arrhythmias, or unstable angina) or significant pulmonary disease (including obstructive pulmonary disease and history of bronchospasm)

E. Study Treatments

Mosunetuzumab

Flat dosing independent of body weight is used for mosunetuzumab. The dose of mosunetuzumab for each patient depends on the dose level assignment as detailed herein.

Mosunetuzumab is administered to patients by IV infusion using standard medical syringes and syringe pumps or IV bags where applicable. Compatibility testing has shown that mosunetuzumab is stable in extension sets and polypropylene syringes. Mosunetuzumab is delivered by syringe pump via an IV infusion set or IV bag with a final mosunetuzumab volume determined by the dose. Mosunetuzumab is administered in a setting with immediate access to trained critical care personnel and facilities equipped to respond to and manage medical emergencies. Neurology consultation services is readily available to address any neurologic adverse events that may arise as a result of mosunetuzumab treatment, and nephrology consultation with acute dialysis capabilities should be readily available to address any renal toxicity that might accompany TLS.

Mosunetuzumab is administered to well-hydrated patients. Corticosteroid premedication consisting of dexamethasone 20 mg IV or methylprednisolone 80 mg IV must be administered at least 1 hour prior to the administration of each mosunetuzumab dose. The administration of corticosteroid premedication may be optional from Cycle 3 and beyond, based on investigator's assessment. However, if the patient experiences CRS in earlier doses, premedication with steroids must be administered for subsequent doses until no additional CRS events are observed. In addition, premedication with oral acetaminophen or paracetamol (e.g., 500-1,000 mg) and/or 50-100 mg diphenhydramine may be administered per standard institutional practice prior to administration of mosunetuzumab.

Initially, mosunetuzumab is infused over 4 hours (±15 minutes). The infusion may be slowed or interrupted for patients experiencing infusion-associated symptoms.

Following each mosunetuzumab dose, patients will be observed at least 90 minutes for fever, chills, rigors, hypotension, nausea, or other signs and symptoms of IRRs or CRS. In the absence of infusion-related adverse events, the infusion time of mosunetuzumab in Cycle 2 and beyond may be reduced to 2 hours (±15 minutes).

The recommended guidelines for the management of CRS and infusion-related reactions (IRRs) are detailed in Table 6.

TABLE 6

Management of Cytokine Release Syndrome and Infusion-Related Reactions for Patients Receiving Mosunetuzumab

| CRS Grade[a] | Action with Current Mosunetuzumab Infusion | Supportive Care | Anti-IL-6/Corticosteroid Therapy | Action for Next Mosunetuzumab Dose |
|---|---|---|---|---|
| Grade 1 Fever ≥38° C. | Slow infusion to ≤50% or interrupt infusion until symptoms resolve; re-start at same rate. If symptoms recur with rechallenge, interrupt study treatment, do not resume, and manage per Grade 2. | Symptomatic management of constitutional symptoms. Consider empiric broad-spectrum antibiotics. Consider G-CSF if neutropenic. Maintenance IV fluids for hydration. Consider hospitalization until symptoms completely resolve. | For prolonged CRS (>2 days) in patients with significant symptoms and/or comorbidities (per investigator discretion, e.g., impaired cardiovascular function, reduced pulmonary reserve), consider tocilizumab and corticosteroids as per Grade 2. | Administer premedications for next dose. Consider 50% (or lower) rate of infusion for next step-up dose in Cycle 1 or 50% rate of infusion if next dose is same dose level (beyond Cycle 1). Consider hospitalization for next dose |
| Grade 2 Fever ≥38° C. with hypotension not requiring vasopressors and/or hypoxia requiring low-flow oxygen[b] by nasal cannula or blow-by | Hold further study treatment until symptoms resolved; consider re-starting infusion at 50% rate. If symptoms recur with rechallenge at decreased infusion rate, interrupt study treatment, do not resume, and manage per Grade 3. | Symptomatic management of constitutional symptoms and organ toxicities. Consider ICU admission for hemodynamic monitoring. For hypotension: IV fluid bolus as needed; for persistent refractory hypotension (e.g., after two fluid boluses and anti-IL-6 therapy), start vasopressors and manage per Grade 3. Rule out other inflammatory conditions which can mimic severe CRS (e.g., infections/ sepsis). Consider empiric broad-spectrum antibiotics. If no improvement within 24 hours, initiate work up and assess for signs and symptoms of HLH. | Consider tocilizumab.[c] For persistent refractory hypotension after 1-2 doses of anti-IL-6 therapy, consider dexamethasone 10 mg IV every 6 hours (or equivalent). Manage per Grade 3 if no improvement within 24 hours after starting tocilizumab. | May receive the next dose of mosunetuzumab if symptoms resolve to Grade ≤1 for 3 consecutive days with approval of Medical Monitor. Consider enhanced premedications for next dose. Consider 50% (or lower) rate of infusion for next step-up dose in Cycle 1 or 50% rate of infusion if next dose is same dose level (beyond Cycle 1). Consider hospitalization for next dose. |
| Grade 3 Fever ≥38° C. with hypotension requiring a vasopressor (with or without vasopressin) and/or hypoxia requiring high-flow oxygen by nasal cannula or blow-by | Stop infusion, do not resume. | Symptomatic management of organ toxicities, admit to ICU for hemodynamic monitoring. For hypotension: IV fluid bolus and vasopressors PRN. Rule out other inflammatory conditions which can mimic severe CRS (e.g., infections/sepsis). Consider empiric broad-spectrum antibiotics. If no improvement within 24 hours, initiate work up and assess for signs and symptoms of HLH. | Administer tocilizumab.[c] Dexamethasone 10 mg IV every 6 hours (or equivalent). If refractory, manage as per Grade 4.[d] Manage per Grade 4 if no improvement within 18-24 hours after second dose of tocilizumab. | May receive the next dose of mosunetuzumab if CRS event was responsive to treatment (i.e., clinical improvement within 8-12 hours following tocilizumab/corticosteroids administration) and symptoms resolve to Grade ≤1 for 3 consecutive days with approval of Medical Monitor: Enhanced premedications for next dose Decrease to 50% (or lower) rate of infusion for next step-up dose in Cycle 1, or 50% rate of infusion if |

TABLE 6-continued

Management of Cytokine Release Syndrome and Infusion-Related Reactions for Patients Receiving Mosunetuzumab

| CRS Grade[a] | Action with Current Mosunetuzumab Infusion | Supportive Care | Anti-IL-6/Corticosteroid Therapy | Action for Next Mosunetuzumab Dose |
|---|---|---|---|---|
| | | | | next dose is same dose level (beyond Cycle 1) Hospitalization for next dose The next dose should be reduced to the next lower dose level that has been previously cleared during dose escalation. [g] Subsequent doses may not be re-escalated with signs/symptoms of Grade 3 or higher CRS at the reduced dose. If the reduced dose is tolerated with no signs/symptoms of Grade 3 or higher CRS, the patient may return to the next higher dose that has been previously cleared during dose escalation. If Grade 3 CRS recurs with subsequent doses, permanently discontinue mosunetuzumab. [h] |
| Grade 4 Fever ≥38° C. with hypotension requiring multiple vasopressors (excluding vasopressin) and/or hypoxia requiring oxygen by positive pressure (e.g., CPAP, BiPAP, intubation and mechanical ventilation) | Stop infusion, do not resume. | ICU admission and hemodynamic monitoring. Mechanical ventilation PRN. IV fluids and vasopressors PRN. Symptomatic management of organ toxicities. Rule out other inflammatory conditions which can mimic severe CRS (e.g., infections/sepsis) Consider empiric broad-spectrum antibiotics. If no improvement within 24 hours, initiate work up and assess for signs and symptoms of HLH. | Administer tocilizumab.[c] For patients refractory to tocilizumab, consider siltuximab, anakinra, and emapalumab, based on discretion of the investigator; management should be discussed with the Medical Monitor.[d] Dexamethasone 10 mg IV every 6 hours (or equivalent). If refractory, consider methylprednisolone 1000 mg/day IV. [e, f] | Permanently discontinue mosunetuzumab. |

ASTCT ® = American Society for Transplantation and Cellular Therapy ®;

BiPAP = bilevel positive airway pressure;

CPAP = continuous positive airway pressure;

CRS = cytokine release syndrome;

G-CSF = granulocyte colony stimulating factor;

HLH = hemophagocytic lymphohistiocytosis;

PRN = pro re nata, i.e., taken as needed.

[a]CRS grading per ASTCT ® (Lee et al. 2019). Fever is defined as temperature ≥38° C. not attributable to any other cause. In patients who have CRS and then receive anti-pyretic or anti-cytokine therapy such as tocilizumab or steroids, fever is no longer required to grade subsequent CRS severity. CRS grade is determined by the more severe event: hypotension or hypoxia not attributable to any other cause.

[b]Low-flow nasal cannula is defined as oxygen delivered at ≤6 L/minute. Low flow also includes blow-by oxygen delivery. High-flow nasal cannula is defined as oxygen delivered at >6 L/minute.

[c]Tocilizumab should be administered at a dose of 8 mg/kg IV (8 mg/kg for participants at a weight of ≥30 kg only; 12 mg/kg for participants at a weight of <30 kg; doses exceeding 800 mg per infusion are not recommended); repeat every 8 hours as necessary (up to a maximum of 4 doses).

[d]Riegler et al. 2019.

[e] Anti-fungal prophylaxis should be strongly considered in patients receiving steroids for treatment of CRS.

[f] For example, methylprednisolone IV 1000 mg/day for 3 days, followed by rapid taper at 250 mg every 12 hours for 2 days, 125 mg every 13 hours for 2 days, and 60 mg every 12 hours for 2 days.

[g] If Grade 3 CRS occurs in the step-up dosing cohorts following mosunetuzumab administration on Days 1 or 8 of Cycle 1, the next mosunetuzumab dose should be discussed with the Medical Monitor and a dose reduction should be considered. Exceptions may be considered to repeat the same step-up dose based on individual benefit-risk assessment.

[h] Resumption of mosunetuzumab may be considered in patients who are deriving benefit and have fully recovered from the adverse event. Patients can be re-challenged with mosunetuzumab only after approval has been documented by both the investigator (or an appropriate delegate) and the Medical Monitor. Further treatment are not considered unless all the criteria below are met:

Individual benefit-risk assessment by Principal Investigator/treating physician favors continued treatment;

The patient has recovered from previous toxicities and has sufficient organ function/reserve to receive subsequent doses;

The patient has been adequately consented for risks associated with continued treatment and decides to receive subsequent doses;

The above risk-benefit assessment and evaluation of patient's are discussed with the Sponsor;

Subsequent doses are well planned with precautionary measures, including dose reduction, slow infusion rate at 50% or lower, mandatory hospitalizations, enhanced premedications, and administration of tocilizumab at first sign of CRS recurrence.

Corticosteroid with or without Vincristine Pre-treatment Prior to Initiation of Study Treatment For patients with previously untreated DLBCL or patients considered to be at high risk for TLS or acute toxicity with the first cycle of study treatment, a pre-phase treatment of prednisone at a dose of up to 100 mg by mouth every day for up to 7 days prior to C1D1 is permitted, at the discretion of the investigator (Pfreundschuh 2010; Tilly et al. 2015).

Vincristine 1 mg is permitted in only as part of the pre-phase treatment. The pre-phase treatment is not considered part of study treatment but is recorded in the electronic Case Report Form (eCRF). The purpose of the pre-phase treatment is to prevent TLS in patients with extensive disease and to reduce toxicity of the first cycle of study treatment (e.g., CRS). Staging study assessments (i.e., CT/MRI, PET-CT scan) must be performed prior to initiation of pre-phase treatment.

Tocilizumab

Tocilizumab should be administered when necessary as described herein. Tocilizumab is supplied by the Sponsor, where required by local health authority regulations. Please refer to the pharmacy manual for administration instructions for tocilizumab.

F. Concomitant Therapy

Concomitant therapy consists of any medication (e.g., prescription drugs, over-the-counter drugs, vaccines, herbal or homeopathic remedies, nutritional supplements) used by a patient in addition to protocol-mandated treatment from 7 days prior to initiation of study drug, including any pre-phase treatment for patients, to the study drug completion/discontinuation visit.

Anti-infective prophylaxis for viral, fungal, bacterial, or *Pneumocystis* infections is permitted and should be instituted per institutional practice or investigator preference based on individual patient risk factors. Patients in countries where prophylactic anti-viral medications for hepatitis B reactivation are the SOC may be treated prophylactically (Flowers et al. 2013; NCCN 2017).

CNS prophylaxis with intrathecal chemotherapy should only be given according to institutional practice and its use documented in the eCRF. CNS prophylaxis using high dose IV methotrexate (e.g., 1 g/m2 per cycle) is not permitted and would be considered a new anti-lymphoma therapy.

Pre-planned radiotherapy (i.e., radiation that was planned before enrollment to be given at the end of study treatment) may be administered to initial sites of bulky or extranodal disease according to institutional practice. If indicated, pre-planned radiotherapy should be administered within 8 weeks after the last study drug treatment and should start after the PRA when PET-CT scans are completed. Any radiotherapy should be pre-planned by the center and documented prior to enrollment (if applicable) and then entered in the eCRF once the patient is enrolled. All unplanned radiotherapy administered to patients is considered as a new anti-lymphoma treatment.

Given the expected pharmacology of mosunetuzumab, the transient release of cytokines may suppress CYP enzymes and cause drug-drug interactions. Preliminary clinical data indicate that mosunetuzumab induced a transient elevation in plasma IL-6, with peak levels occurring in the majority of patients within 4-6 hours of the C1D1 dose, and returning to baseline by 24 hours. Patients who may be of highest risk of a drug-drug interaction are those receiving concomitant medications that are CYP substrates and have a narrow therapeutic index (see Table 7 below).

CYP enzymes in the liver are down-regulated by infection and inflammation stimuli including cytokines such as IL-6. Inhibition of IL-6 signaling in rheumatoid arthritis patients treated with tocilizumab may restore CYP activities to higher levels than those in the absence of tocilizumab leading to increased metabolism of drugs that are CYP substrates. In vitro studies showed that tocilizumab has the potential to affect expression of multiple CYP enzymes, including CYP1 A2, CY2B6, CYP2C9, CYP2C19, CYP2D6, and CYP3A4. Its effects on CYP2C8 or transporters are unknown. In vivo studies with omeprazole, metabolized by CYP2C19 and CYP3A4, and simvastatin, metabolized by CYP3A4, showed up to a 28% and 57% decrease in exposure 1 week following a single dose of tocilizumab, respectively. The effect of tocilizumab on CYP enzymes may be clinically relevant for CYP substrates with narrow therapeutic index, where the dose is individually adjusted. Upon initiation or discontinuation of tocilizumab in patients being treated with these types of medicinal products, therapeutic monitoring of effect (e.g., warfarin) or drug concentration (e.g., cyclosporine or theophylline) should be performed, and the individual dose of the medicinal product adjusted PRN. Prescribers should exercise caution when tocilizumab is co-administered with CYP3A4 substrate drugs where decrease in effectiveness is undesirable (e.g., oral contraceptives, lovastatin, and atorvastatin). The effect of tocilizumab on CYP enzyme activity may persist for several weeks after stopping therapy (see Table 7 below).

TABLE 7

Examples of Sensitive In Vivo CYP Substrates and
CYP Substrates with Narrow Therapeutic Range

| CYP Enzymes [a] | Sensitive Substrates [b] | Substrates With Narrow Therapeutic Range [c] |
|---|---|---|
| CYP1A2 | Alosetron, caffeine, duloxetine, melatonin, ramelteon, tacrine, tizanidine | Theophylline, tizanidine |
| CYP2B6 [d] | Bupropion, efavirenz | |
| CYP2C8 | Repaglinide [e] | Paclitaxel |
| CYP2C9 | Celecoxib | Warfarin, phenytoin |
| CYP2C19 | Lansoprazole, omeprazole, S-mephenytoin | S-mephenytoin |
| CYP3A [f] | Alfentanil, aprepitant, budesonide, buspirone, conivaptan, darifenacin, darunavir, dasatinib, dronedarone, eletriptan, eplerenone, everolimus, felodipine, indinavir, fluticasone, lopinavir, lovastatin, lurasidone, maraviroc, midazolam, nisoldipine, quetiapine, saquinavir, sildenafil, simvastatin, sirolimus, tolvaptan, tipranavir, triazolam, vardenafil | Alfentanil, astemizole [g], cisapride [g], cyclosporine, dihydroergotamine, ergotamine, fentanyl, pimozide, quinidine, sirolimus, tacrolimus, terfenadine [g] |

TABLE 7-continued

Examples of Sensitive In Vivo CYP Substrates and
CYP Substrates with Narrow Therapeutic Range

| CYP Enzymes [a] | Sensitive Substrates [b] | Substrates With Narrow Therapeutic Range [c] |
|---|---|---|
| CYP2D6 | Atomoxetine, desipramine, dextromethorphan, metoprolol, nebivolol, perphenazine, tolterodine, venlafaxine | Thioridazine |

[a] Note that this is not an exhaustive list. For an updated list, see the following link: link: https://www.fda.gov/Drugs/DevelopmentApprovalProcess/DevelopmentResources/DrugInteractionsLabeling/ucm080499.htm.
b Sensitive CYP substrates refer to drugs whose plasma AUC values have been shown to increase 5-fold or higher when co-administered with a known CYP inhibitor.
[c] CYP substrates with narrow therapeutic range refers to drugs whose exposure-response relationship indicates that small increases in their exposure levels by the concomitant use of CYP inhibitors may lead to serious safety concerns (e.g., Torsades de Pointes).
[d] The AUC of these substrates were not increased by 5-fold or more with a CYP2B6 inhibitor, but they represent the most sensitive substrates studied with available inhibitors evaluated to date.
[e] Repaglinide is also a substrate for OATP1B1, and it is only suitable as a CYP2C8 substrate if the inhibition of OATP1B1 by the investigational drug has been ruled out.
[f] Because a number of CYP3A substrates (e.g., darunavir, maraviroc) are also substrates of P-gp, the observed increase in exposure could be due to inhibition of both CYP3A and P-gp.
[g] Withdrawn from the United States market because of safety reason.

G. Safety Concerns and Management

Measures are taken to ensure the safety of patients participating in this trial, including the use of stringent inclusion and exclusion criteria and close monitoring, as described below. All patients are monitored closely for toxicity. Patients are assessed clinically for toxicity prior to each dose using the NCI® CTCAE v5.0 grading scale unless otherwise stated. CRS severity is graded according to the ASTCT® CRS Consensus Grading. Specific anticipated or potential toxicities associated with administration of mosunetuzumab, as well as the measures taken intended to avoid or minimize such toxicities in this trial, are described in the following sections.

Mosunetuzumab Administration and Hospitalization

Based on available clinical safety data and the recommendation of the IMC, for patient in expansion, hospitalization is not mandatory after any dosing day. Instead, the investigator assesses the need for hospitalization for individual patients, and patients is hospitalized after mosunetuzumab administration whenever clinically indicated. Examples where such hospitalization may be warranted include, but are not limited to, prior observed Grade>2 adverse events potentially attributable to mosunetuzumab at the same or similar dose, lack of social support, patients at high risk for CRS (risk factors may include high Ann Arbor stage, bulky disease, bone marrow involvement, etc.), and TLS monitoring and prophylaxis.

Cytokine Release Syndrome

To minimize the risk and sequelae of IRRs and CRS, mosunetuzumab is administered over a minimum of 4 hours in Cycle 1 in a clinical setting, as described herein. Corticosteroid premedication is also administered as described herein.

Mild to moderate presentations of IRRs and/or CRS may include symptoms such as fever, headache, and myalgia, and may be treated symptomatically with analgesics, anti-pyretics, and anti-histamines as indicated.

Severe or life-threatening presentations of IRRs and/or CRS, such as hypotension, tachycardia, dyspnea, or chest discomfort, should be treated aggressively with supportive and resuscitative measures as indicated, including the use of tocilizumab and/or high-dose corticosteroids, IV fluids, and other supportive measures per local institutional practice. Severe CRS may be associated with other clinical sequelae, such as disseminated intravascular coagulation and capillary leak syndrome, or may manifest as HLH.

Management guidelines for CRS following mosunetuzumab are summarized in Table 6, with the grading of CRS following ASTCT® CRS Consensus Grading described in Table 1. Management of Grade≥3 IRR and/or CRS should be immediately discussed between the treating investigator and the Medical Monitor.

Infusion-Related Reactions

For IV mosunetuzumab administration, the recommended management of infusion-related reactions (IRRs), which may be indistinguishable from CRS, is described above. Management guidelines for IRRs are the same as those described for the management of CRS in Table 6.

Neutropenia

Neutropenia is a known class effect associated with other CD20-directed therapies as well as blinatumomab (Blincyto USPI). Reversible neutropenia has been observed following mosunetuzumab treatment. Some patients developing neutropenia have received growth factor support and/or temporary treatment holds. Patients who experience Grade 3-4 neutropenia should be closely monitored with more frequent assessments as applicable. Mosunetuzumab step doses should not be held for uncomplicated neutropenia without associated fever or for thrombocytopenia without associated bleeding in Cycle 1.

Macrophage Activation Syndrome (MAS)/Hemophagocytic lymphohistiocytosis (HLH)

While severe CRS and secondary HLH have overlapping presentation and symptoms, secondary HLH may be precipitated by other conditions including infections, autoimmune disease, and malignancies (Ramos-Casals 2014). The prevalence of these conditions in the study patient population makes the distinction between severe CRS and secondary HLH and identification of inciting factors challenging. For example, in one series, B-cell malignancies were the most common malignancy associated with secondary HLH (Riviere et al. 2014). Furthermore, active infection with EBV is one of the most common infectious causes of secondary HLH (Hashemi-Sadraei et al. 2015; Schram and Berliner 2015), while reactivation of latent EBV may occur in patients with CLL (Rath et al. 2008), which in turn may lead to HLH (Lim et al. 2014). It remains unknown whether mosunetuzumab treatment may further increase the risk of developing HLH in patients who have additional risk factors.

In the setting of T-cell engaging therapies including mosunetuzumab, CRS is much more likely to occur compared with secondary HLH; considering the overlapping presentation of symptoms, management of these patients should be primarily focused on treatment of CRS. In "atypical" cases, such as late-onset CRS (past Cycle 1) or CRS that is refractory to treatment, workup for HLH should be initiated.

Treatment options of HLH in cases where tocilizumab with or without high-dose corticosteroids fail to induce the desired response is based on published guidelines (La Rosée 2015; Schram and Berliner 2015) and considered between the Sponsor and investigator on a case-by-case basis, given that there is no SOC for HLH in these clinical situations.

Neurologic Adverse Events

Encephalopathy has been observed in in the setting of CRS and/or elevation in liver function tests (LFTs) following mosunetuzumab treatment. Neurologic AEs are monitored closely during the trial. All patients are required to undergo a baseline complete neurologic examination prior to the first mosunetuzumab administration; the examination includes an evaluation of mental status, cranial nerves, motor strength, sensation, and coordination. Patients are routinely assessed for any signs or symptoms of neurologic toxicity as part of the on-treatment clinical examination. If new or worsening neurologic toxicity is suspected, the patient should be referred to a neurologist for further evaluation of potential drug-related neurotoxicity. Corticosteroids should be considered to treat suspected neurologic toxicity.

Decisions on whether to continue or to hold mosunetuzumab treatment for any Grade 1 neurotoxicity is at the discretion of the study investigator and with the approval of the Medical Monitor. For Grade≥2 neurologic toxicity, treatment with mosunetuzumab should be held until the toxicity returns to baseline for at least 3 days without any medication. For Grade 3 neurologic toxicity lasting >7 days, the overall benefit-risk of continued treatment with mosunetuzumab should be assessed by the study investigator in consultation with and approval of the Medical Monitor. If Grade 3 neurologic toxicity recurs in any subsequent cycles, mosunetuzumab should be permanently discontinued.

Mosunetuzumab should be permanently discontinued for Grade≥3 seizures.

Tumor Lysis Syndrome

TLS is a known progressive disease (PD) effect of anti-tumor therapy in hematologic malignancies including NHL. There is the theoretical risk of TLS if treatment with mosunetuzumab results in the rapid destruction of a large number of tumor cells. The risk of TLS with mosunetuzumab in patients with NHL is predicted to be highest for those with bulky disease (defined in the context of TLS as any lesion ≥10 cm on the screening CT scan) and elevated pretreatment lactic acid dehydrogenase (LDH) levels, particularly in the presence of dehydration or compromised renal function. While DLBCL, transformed lymphomas, and mantle cell lymphomas may be at higher risk of TLS as compared with follicular, marginal, and small cell lymphomas (Cairo et al. 2010), any risk stratification based on tumor type must be considered along with the effectiveness of therapy (Howard et al. 2011). As mosunetuzumab has the potential for potent B-cell killing, all patients receive prophylaxis for TLS.

Prior to each mosunetuzumab treatment given during Cycles 1 and 2, the patient's serum chemistry and hematology laboratory samples are obtained and reviewed, and prophylactic measures initiated according to the guidelines described herein. Access to nephrologist and acute dialysis services must be available in the event of clinically significant TLS.

All patients receive prophylaxis for TLS prior to each mosunetuzumab administration during Cycles 1 and 2. Prophylaxis guidelines include the following:

Hydration, consisting of a fluid intake of approximately 2-3 L/day starting 24-48 hours prior to the first dose of mosunetuzumab; followed by IV hydration at a rate of 150-200 mL/hour beginning at the conclusion of first administration of mosunetuzumab and continued for at least 24 hours thereafter. Modification of fluid rate should be considered for individuals with specific medical needs. Continuation of supportive hydration may be extended beyond 24 hours per investigator discretion.

Administration of an agent to reduce uric acid:

Allopurinol (e.g., 300 mg/day orally beginning 72 hours prior to dose and continuing for 3-7 days afterward) should be administered for those patients judged to be of low or intermediate risk of developing TLS per investigator's judgment.

For patients with elevated uric acid levels prior to mosunetuzumab treatment, or considered to be at high risk for TLS: Rasburicase (e.g., 0.2 mg/kg IV over 30 minutes prior to the first dose mosunetuzumab and daily for up to 5 days thereafter) should be administered, unless contraindicated (ELITEK® USPI).

Treatment with allopurinol/rasburicase should continue as specified above, or if laboratory evidence of TLS is observed until normalization of serum uric acid or other laboratory parameters.

Infections

Due to its anticipated mode of action resulting in profound B-cell depletion, mosunetuzumab may be associated with an increased risk of infections. Mosunetuzumab should not be administered in the presence of active severe infections. Hepatitis B reactivation has been reported with other CD20-directed therapies. Patients with HIV infection are excluded from participation in the study because signs and symptoms of HIV may confound assessment of the safety profile of mosunetuzumab.

Elevated Liver Enzymes and Hepatotoxicity

Transient Grade 3 AST elevation in the setting of Grade 2 CRS, as well as Grade 3 hepatic encephalopathy/Grade 4 elevation in LTs, have been observed following mosunetuzumab treatment. Patients who do not meet eligibility criteria for LFTs at screening are excluded from this trial. LTs are assessed regularly during study and managed according to Table 8 below.

TABLE 8

| Management Guidelines for Liver Function Test Abnormalities and Hepatotoxicity for Patients Receiving Mosunetuzumab | |
|---|---|
| LFT Abnormality | Management |
| Grade 1 AST or ALT elevation - OR - | Continue mosunetuzumab Monitor LFTs (including AST, ALT, and bilirubin) weekly. |

TABLE 8-continued

Management Guidelines for Liver Function Test Abnormalities
and Hepatotoxicity for Patients Receiving Mosunetuzumab

| LFT Abnormality | Management |
| --- | --- |
| AST/ALT ≥3 × baseline value | For AST/ALT ≥3 × baseline value but < Grade 1, notify Medical Monitor prior to subsequent study treatment. |
| Grade 2 AST or ALT elevation | All events:<br>Withhold mosunetuzumab<br>Monitor LFTs at least weekly and as clinically indicated until values resolve to normal or baseline.<br>Resume mosunetuzumab when resolved to Grade ≤1 or baseline.<br>Consider hepatology consultation.<br>Events >5 days' duration:<br>Obtain hepatology consultation; evaluate etiology. |
| Grade 3 AST or ALT elevation | All events:<br>Withhold mosunetuzumab.<br>Monitor LFTs every 24-48 hours until decreasing, and then follow weekly.<br>Obtain hepatology consultation; consider liver biopsy to assess hepatic injury. [a]<br>Resume mosunetuzumab when resolved to Grade ≤1 or baseline.<br>Events >5 days' duration<br>Resume mosunetuzumab when resolved to Grade ≤1 or baseline, following approval of Medical Monitor. [a] |
| Grade 4 AST or ALT elevation | Permanently discontinue mosunetuzumab. [b]<br>Follow management guidelines as described for Grade 3 events. |

CRS = cytokine release syndrome; LFT = liver function test; HLH = hemophagocytic lymphohistiocytosis.
[a] Immune-related event should be considered when concurrent clinical and laboratory manifestations of CRS or HLH are present, or in instances where no alternative etiology (e.g., viral, neoplastic) can account for observed LFT abnormalities.
[b] Resumption of mosunetuzumab may be considered in patients who are deriving benefit and have fully recovered from the immune-related event. Patients may resume dosing with mosunetuzumab only after documented approval by the investigator and the Medical Monitor.

Immunogenicity

As with any recombinant antibody, mosunetuzumab may elicit an immune response, and patients may develop antibodies against the molecule. Patients are closely monitored for any potential immune response to mosunetuzumab in the first-line treatment setting, which may have an impact on the benefit-risk profile of the agent. Therefore, a risk-based strategy (Rosenberg and Worobec 2004a, 2004b, 2005; Koren et al. 2008) is utilized to detect and characterize anti-drug antibodies (ADA) responses to mosunetuzumab. Because mosunetuzumab is a B-cell-depleting agent and has demonstrated low immunogenicity rates in the Phase I study, the frequency of ADA sampling times for mosunetuzumab has been reduced in this study.

Tumor Inflammation/Flare

Consistent with the mechanism of action of mosunetuzumab, tumor flare is likely due to the influx of T cells into tumor sites following mosunetuzumab administration. Reported tumor flare-associated adverse events generally have a short time to onset following mosunetuzumab administration. On the basis of safety data collected to date, tumor flare has manifested as new or worsening pleural effusions, local swelling, and tumor pain. In addition, depending on tumor size and anatomic location, tumor flare may potentially result in mass effects on vital structures including airways, major blood vessels, gastrointestinal tract (risk of perforation and hemorrhage), and/or major organs. Patients with tumors at critical anatomic locations should be closely monitored for tumor flare, and the treating physician/study investigator should contact the Medical Monitor to discuss risk assessment and mitigation strategies prior to mosunetuzumab treatment.

Dose Delays and Dose Modifications

No intrapatient dose reductions of mosunetuzumab are allowed, but dose delays and modifications are allowed. If toxicity occurs after the C1D3 dose mosunetuzumab dose on Day 15 of Cycle 1, then a cohort dose de-escalation may be considered after implementing specific mitigation factors.

Treatment Interruption

Study treatment may be temporarily suspended in patients who experience toxicity considered to be related to study drug. Study drug withheld for ≥14 days because of toxicity should be discontinued unless resumption of treatment is approved following investigator discussion with the Medical Monitor.

Study treatment may be suspended for reasons other than toxicity (e.g., surgical procedures) with Medical Monitor approval. The investigator and the Medical Monitor determine the acceptable length of treatment interruption. If scheduled dosing coincides with a holiday that precludes dosing, dosing should commence on the nearest following date, with subsequent dosing continuing on a 21-day schedule as applicable.

Specific guidelines around schedule modifications are detailed below. Patients who are receiving study treatment and experience toxicities should undergo dose interruptions and reductions per instructions disclosed herein.

In general, patients who experience a Grade 4 non-hematological adverse event should discontinue all study treatment and may not be re-treated. An exception to this relates to TLS. Because TLS represents a PD effect of study treatment that may result in clinical benefit, patients who experience Grade 4 TLS may be considered for continuation on study. To be considered for subsequent study treatment, all toxicities and laboratory abnormalities related to TLS should be resolved within 2 weeks. The decision to continue study treatment should only be made after consultation with the study investigator and approval by the Medical Monitor. Patients must be hospitalized for TLS prophylaxis and monitoring with the next study treatment dose.

For patients who experience IRRs or CRS with the first dose of mosunetuzumab or are at increased risk of recurrent IRRs/CRS with subsequent doses, the time of infusion may be extended to up to 8 hours. Modifications to infusion time in these circumstances should be discussed with the Medical Monitor.

Patients who experience a Grade 3 adverse event or a serious adverse event are allowed to delay mosunetuzumab dosing for up to 2 weeks in order to recover from the toxicity.

For those adverse events that are not considered by the investigator to be attributable to another clearly identifiable cause, (e.g., documented disease progression, concomitant medication, or preexisting medical condition), patients may continue to receive additional doses of mosunetuzumab, provided that the toxicity has resolved to Grade≤1 within the time period stated above.

For decreased laboratory values, the abnormality should have resolved to the lower limit of Grade≤1, or return to ≥80% of the baseline value, whichever is lower.

For increased laboratory values, the abnormality should have resolved to the upper limit of Grade≤1, or return to ≥120% of the baseline value, whichever is higher.

Patients who do not fulfill the criteria for dosing after the additional 2 weeks have elapsed are discontinued from study treatment and be followed for safety outcomes. Exceptions to this on the basis of ongoing clinical benefit may be allowed following investigator assessment of risk versus benefit with approval from the Medical Monitor. Delay of therapy because of toxicities not attributed to mosunetuzumab may not require discontinuation following investigator assessment of risk versus benefit with approval from the Medical Monitor.

If a serious adverse event or adverse event of special interest occurs following C1D1, C1D2, and/or C1D3 dosing, a treatment delay of mosunetuzumab up to 14 days and/or modification of the subsequent mosunetuzumab dose may occur at the discretion of the Medical Monitor following consultation with the treating investigator physician. In the event that a patient has a non-hematologic toxicity prior to C1D3 dose that necessitates mosunetuzumab interruption for >7 days, the patient is required to repeat mosunetuzumab at the highest dose previously tolerated prior to resuming planned treatment schedule.

Patients who discontinue study treatment for reasons other than progressive disease should continue to be followed.

H. Analyses

This Phase I/I1 study is designed to assess the safety and tolerability of mosunetuzumab as monotherapy. The efficacy and safety analyses will be based on the safety-evaluable population (i.e., patients who received any amount of any study treatment), according to the actual treatment received. The primary endpoint is safety and the primary efficacy endpoint is PET-CT CR rate at the end of the initial treatment per Lugano 2014 criteria as assessed by the investigator.

Efficacy Analyses

The analysis population for the efficacy analyses consist of all treated patients, with patients.

The primary efficacy endpoint is the CR rate at the PRA (6-8 weeks after C8D1 or final dose of study treatment) as measured by PET-CT scan. The CR rate, defined as the proportion of patients with CR is estimated and the corresponding Clopper-Pearson exact 95% CI is constructed. Response assessment is determined using the Lugano 2014 criteria (Cheson et al. 2014).

Secondary efficacy endpoints are described below. Patients without a post-baseline tumor assessment are considered non-responders. Analyses of these endpoints are identical to those described above for the primary efficacy endpoint.

ORR, defined as the proportion of patients with a CR or PR, at PRA based on PET-CT as determined by the investigator.

Best ORR (CR or PR at any time) in study based on PET-CT and/or CT scans as determined by the investigator.

DOR, defined as the time from the first occurrence of a documented objective response (CR or PR) to disease progression, relapse, or death from any cause, whichever occurs first.

For patients who do not experience death or disease progression, DOR is censored at the date of last evaluable tumor assessment. DOR is assessed by the investigator using the Lugano 2014 criteria (Cheson et al. 2014). Analyses of DOR includes only patients with objective responses (CR or PR) at any time in the study. The Kaplan-Meier method (Kaplan and Meier 1958) is used to estimate the distribution of DOR and median DOR (if analytically possible) for each cohort, with 95% CI for the median DOR constructed using the Brookmeyer-Crowley method (Brookmeyer and Crowley 1982). DOR is also summarized for the subgroups of patients whose best objective response is PR and patients whose best objective response is CR.

PFS, defined as the time from the first study treatment to the first occurrence of disease progression, relapse, or death from any cause, whichever occurs first.

For patients who do not experience disease progression, relapse or death, PFS is censored at the date of last evaluable tumor assessment. For patients who do not have a post-baseline evaluable tumor assessment, PFS is censored at the date of first study treatment plus 1 day. PFS is assessed by the investigator, using the Lugano 2014 criteria (Cheson et al. 2014). The Kaplan-Meier method (Kaplan and Meier 1958) is used to estimate the distribution of PFS, median (if analytically possible), 6-month and 1-year PFS for each cohort, with 95% CI for the median PFS constructed using the Brookmeyer-Crowley method (Brookmeyer and Crowley 1982). The Greenwood's formula is used to provide standard errors and the corresponding 95% Cis for 6-month PFS and 1-year PFS.

OS, defined as the time from first study treatment, to the date of death from any cause.

Patients who have not died are censored at the last date known to be alive. Analyses of OS are identical to those outlined previously for PFS.

Time to deterioration in physical functioning according to the EORTC QLQ-C30 and EORTC IL17; time to deterioration in fatigue as per the EORTC-QLQ-C30; and time to deterioration in lymphoma symptoms according to the FACT-Lym subscale Proportion of patients achieving a clinically meaningful improvement in physical functioning as measured by EORTC QLQ-C30 and EORTC IL17

Time to deterioration is summarized in descriptive statistics. For both physical functioning (EORTC QLQ-C30 and EORTC IL17) and fatigue (EORTC QLQ-C30), deterioration is defined as a ≥10-point worsening from baseline (Osoba et al. 1998). For lymphoma symptoms (FACT Lym subscale), deterioration is defined as ≥3-point worsening from baseline (Carter et al. 2008; Hlubocky et al. 2013). Kaplan-Meier methodology is used to estimate the median time to deterioration f, and Kaplan-Meier curves will be produced. Patients without occurrence of deterioration at the CCOD are censored at the last available assessment.

Safety Analyses

All safety analyses are based on the safety-evaluable population (i.e., patients who received any study treatment), according to the actual treatment received. Safety will be assessed through summaries of adverse events, summaries of changes from screening assessments in laboratory test results, ECGs, and changes in vital signs. All collected adverse event data are summarized by stage of the study and treatment cohort. All adverse events occurring on or after first study treatment are summarized by mapped term, appropriate thesaurus levels, CRS by ASTCT® CRS Consensus Grading, and NCI® CTCAE v5.0 toxicity grade. All serious adverse events are listed separately and summarized. Deaths reported during the study treatment period and those reported during follow-up after treatment discontinuation are listed. Relevant laboratory and vital sign (temperature, pulse rate, respiratory rate, pulse oximetry, and blood pressure) data are displayed by time, with NCI® CTCAE v5.0 Grade 3 and 4 values identified where appropriate.

Pharmacokinetic Analyses

Individual and mean serum concentration of mosunetuzumab versus time data are tabulated and plotted by dose level. The $C_{max}$ and $C_{min}$ of mosunetuzumab and are summarized. For patients with dense PK sampling scheme, additional PK parameters of mosunetuzumab are calculated including AUC, drug clearance, and volume of distribution at steady state as appropriate for data collected. Estimates for these parameters are tabulated and summarized.

Compartmental, non-compartmental, and/or population methods may be considered. Additional PK analyses are conducted as appropriate.

Relationship between serum pharmacokinetics and safety, biomarkers, and efficacy endpoints are explored, as appropriate.

Biomarker Analyses

Exploratory analyses of biomarkers related to tumor and disease biology as well as the mechanisms of action of mosunetuzumab are conducted.

The association between candidate biomarkers and PET-CT CR rate and other measures of efficacy and safety, with treatment and independent of treatment, is explored to assess potential predictive and prognostic value, respectively. The effects of baseline prognostic characteristics, including DLBCL subtypes (i.e., COO), on efficacy are evaluated using univariate and/or multivariate statistical methods such as Cox regression and logistic regression.

Exploratory PD analyses include assessments of biomarkers in both blood and tumor tissue when available.

Example 2. Rationale for Treatment Selection, and Comorbidities in Older Patients (Pts) with Previously Untreated (1L) Diffuse Large B-Cell Lymphoma (DLBCL): Insights from Real World Data (RWD)

A. Introduction

DLBCL is a significant source of cancer morbidity and mortality in the United States. Due to concerns of frailty and comorbidities in elderly pts (≥80 years old), not all elderly pts receive standard of care regimens (rituximab plus cyclophosphamide, doxorubicin, vincristine, and prednisone (R-CHOP) or R-miniCHOP) as first-line (1 L) treatment; those who do not may have suboptimal outcomes. There is a lack of data regarding comorbidities or other factors (such as patient preference) that influence 1 L treatment choice and inform best practices. This study aims to use Real World Data (RWD) to describe factors influencing 1 L treatment decisions in elderly pts with DLBCL. Comorbidities include, e.g., anemia, arrhythmias, cerebrovascular accident (CVA), cerebrovascular disease (CVD), chronic obstructive pulmonary disease not otherwise specified (COPD: NOS), congestive heart failure (CHF), type 2 diabetes, diabetes with end organ damage (EOD), diabetes without EOD, hyperlipidemia, hypothyroidism, myocardial infarction, peripheral vascular disease, acute kidney disease, chronic kidney disease, stroke, and transient ischemic attack (TIA).

B. Materials and Methods

This study used the US nationwide Flatiron Health electronic health record-derived de-identified database, a longitudinal database comprising patient-level structured and unstructured data, curated via technology-enabled abstraction. Information on treatment rationale for selection of the first-line treatment and comorbidities up to the time of first-line treatment initiation was extracted by trained clinical reviewers from the unstructured parts in the patients' electronic health record (EHR) such as physician notes, and aggregated using information from structured fields such as diagnostic codes. Patients aged ≥71 years with a DLBCL diagnosis on or after Jan. 1, 2011 and follow-up until May 31, 2020 were included. Selected pts were untreated, or treated with: R-CHOP, reduced-dose R-CHOP (<80% standard dose cyclophosphamide and doxorubicin), rituximab monotherapy (R-mono), rituximab plus bendamustine (R-Benda), rituximab plus cyclophosphamide vincristine prednisolone (R-CVP) or rituximab plus lenalidomide (R-Len). Baseline characteristics including demographic and select clinical characteristics at the time of DLBCL diagnosis, comorbidities and treatment rationale, and outcomes in terms of overall survival (OS) were analyzed. Charlson Comorbidity Index (CCI) was used to summarize comorbidities.

404 pts aged ≥71 years were included in the analysis. Overall, at diagnosis, median age was 79 years, 48% of pts were female, 55% had extranodal disease, 19% and 26% of pts had Ann Arbor stage III and IV, respectively; 36% (n=145) of pts had a CCI score of ≥2. Patient characteristics by treatment arm are shown in FIG. 2.

FIG. 3 shows comorbidities at diagnosis with an incidence of ≥5% Comorbidities affecting the largest numbers of pts included hyperlipidemia (36.6%), anemia (24.8%), arrhythmia (19.6%), hypothyroidism (14.6%) and type 2 diabetes (14.6%). Most pts were treated in a community setting (94%) and had DLBCL—not otherwise specified (90%).

C. Results

Shorter OS was observed for 1 L treatments other than R-CHOP treatments. Median time from diagnosis to 1 L treatment was 24 days (IQR: 12-39). OS by treatment status and OS by 1 L treatment are shown in FIGS. 4A-4B and FIGS. 5A-5B, respectively. Data for R-Len was not included due to small sample size available (N=2). Pts receiving no treatment have worse survival outcomes. Shorter survival was observed for regimens other than R-CHOP as 1 L treatment. A higher comorbidity burden (defined as a CCI score of ≥2) appeared to be associated with a shorter median OS (Table 9).

TABLE 9

OS according to CCI Score Category

| | Median OS, months (95% CI) | | | | |
|---|---|---|---|---|---|
| CCI Score Categories | R-Benda (n = 56) | R-CHOP (n = 59) | R-CVP (n = 58) | R-mono (n = 57) | Reduced-dose R-CHOP (n = 115) |
| 0-1 | 31 (15-NR) | 91 (91-NR) | 26 (15-NR) | 24 (7-NR) | 67 (47-NR) |
| ≥2 | 10 (6-46) | 44 (40-NR) | 29 (11-NR) | 9 (4-31) | 18 (8-NR) |

Data for R-Len-treated pts (n = 2) are not included due to small sample size available.
NR, not reached Age and comorbidity were the most commonly reported rationales influencing 1 L treatment choice. Rationale by 1 L treatment in pts receiving both systemic treatment and radiotherapy is shown in FIG. 6. Age was a reason for attenuated regimen selection in pts receiving reduced-dose R-CHOP (29.5%), R-CVP (28.9%), R-mono (28.7%) and R-Benda (18.8%). Comorbidity was the principal rationale for several pts receiving R-CVP (26.3%), R-Benda (23.4), reduced-dose R-CHOP (15.8%) and R-mono (15.1%). No evidence of a rationale could be found for 83.6% of pts who received the standard-of-care (R-CHOP), potentially indicating that factors related to age or frailty were not significant in the choice of their treatment. In pts not receiving any treatment for whom a rationale was given, patient request accounted for 29%, while age, comorbidities, performance status (PS), or disease burden accounted for most other pts (>50%).

D. Conclusions

Age, comorbidity, and PS are decisive factors in 1 L treatment selection for older pts with DLBCL, with disease burden or IPI rarely stated as the rationale; here, information on rationale is limited to what was recorded in the electronic health record (HER) which could vary among individual physicians or cancer centers. Age and comorbidity were found to be the most frequently documented rationales guiding treatment selection in pts not receiving standard-of-care (R-CHOP). The main reasons for not treating pts appear physician-driven rather than patient-requested, suggesting more pts may receive therapy if physicians have better treatment options. Further analysis of the impact of patient-related factors on treatment decision-making is warranted.

Example 3. Mosunetuzumab Monotherapy for Elderly/Unfit Patients (Pts) with First-Line Diffuse Large B-Cell Lymphoma (DLBCL) Continues to Show Promising Safety and Efficacy with Durable Complete Responses

A. Introduction

Rituximab plus cyclophosphamide, doxorubicin, vincristine, and prednisone (R-CHOP) is standard of care for patients (pts) with previously untreated DLBCL, but it may be unsuitable for some older and/or unfit pts. Real-world data suggest that most elderly pts (aged ≥80 years) with previously untreated DLBCL do not receive R-CHOP at the standard dose, and that the attenuated R-CHOP or other R-based regimens that are often given are associated with inferior outcomes. Better tolerated and more efficacious treatments are needed for these pts. Mosunetuzumab is a CD20×CD3 bispecific antibody that has shown manageable toxicity and promising efficacy in pts with relapsed/refractory DLBCL. An ongoing, multicenter, Phase I/II study (NCT03677154) is evaluating the safety and efficacy of mosunetuzumab monotherapy in elderly and/or unfit pts with previously untreated DLBCL, who are considered unsuitable for standard R-CHOP therapy. The present study is reported with a data cut-off date of Apr. 12, 2021

B. Materials and Methods

Two safety-evaluation cohorts were assessed (mosunetuzumab 13.5 mg and 30 mg), followed by an expansion phase (mosunetuzumab 30 mg). Pts were aged ≥80 years, or 60-79 years with impairment in ≥1 activity of daily living (ADL) or instrumental ADL (IADL), or impaired cardiac, renal or liver function precluding standard full-dose R-CHOP therapy. Pts received optional pre-treatment with prednisone (±vincristine), followed by intravenous mosunetuzumab in step-up doses on Days 1 (Cycle 1 Dose 1, i.e., C1D1; 1 mg), 8 (Cycle 1 Dose 2, i.e., C1D2; 2 mg) and 15 (Cycle 1 Dose 3, i.e., C1D3: 13.5/30 mg) of Cycle (C) 1 and full dose mosunetuzumab (e.g., equivalent in amount to the C1D3) on Day 1 of each subsequent 21-day cycle. Pts with a complete response (CR) stop mosunetuzumab treatment after 8 cycles; pts with a partial response (PR) or stable disease can continue mosunetuzumab treatment for a total of 17 cycles. See FIG. 1 for details.

At data cut-off (Apr. 12, 2021), 48 pts had received mosunetuzumab monotherapy. Eight pts were enrolled into the 13.5 mg safety cohort, seven into the 30 mg safety cohort and 33 into the 30 mg expansion cohort. Patient characteristics are reported below in Table 10. The median number of mosunetuzumab cycles received was 7 (range: 0-16). Most pts were aged ≥80 years, and all pts had an ECOG Performance Status score≤2. Median age was 83 years (range: 65-100), 26 pts (54.2%) had Ann Arbor Stage III-IV disease, and 37 pts (77.1%) had an International Prognostic Index (IPI) score ≥2. Of 12 pts aged <80 years, 5 had impaired renal function, 2 had impaired cardiac function with or without impairment in ≥1 ADL and/or IADL, and 5 had impairment in ≥1 ADL and/or IADL only.

21 pts received pre-phase treatment with prednisone±vincristine.

TABLE 10

Baseline Patient and Disease Characteristics

| n (%) unless stated | 1L DLBCL (N = 48) |
|---|---|
| Median age, years (range) | 83 (65-100) |
| Aged ≥80 years | 36 (75.0) |
| Aged <80 years | 12 (25.0) |
| Female | 31 (64.6) |
| IPI score ≥2 | 37 (77.1) |
| ECOG Performance Status | |
| 0 | 9 (18.8) |
| 1 | 23 (47.9) |
| 2 | 16 (33.3) |
| Ann Arbor Stage | |
| I | 7 (14.6) |
| II | 15 (31.3) |
| III | 6 (12.5) |
| IV | 20 (41.7) |
| Elevated LDH | 23 (47.9) |
| Cell of origin | |
| GCB | 20 (41.7) |
| Non-GCB* | 23 (47.9) |
| WHO subtype | |
| DLBCL | 39 (81.3) |
| DHL/THL | 9 (18.8) |

*Locally assessed by immunohistochemistry.
DHL, double-hit lymphoma;
GCB, germinal centre B-cell;
LDH, lactate dehydrogenase;
THL, triple-hit lymphoma;
WHO, World Health Organization.

C. Results

Mosunetuzumab monotherapy had a manageable safety profile in older pts. Adverse events experienced by patients in the study are summarized below in Table 11. Almost all pts (93.8%) experienced ≥1 adverse event (AE). Most pts (72.9%) had ≥1 AE that was considered treatment-related by investigators. The most common AEs were CRS (29.2% of pts), fatigue (18.8%), and abdominal pain (14.6%). Febrile neutropenia (Grade 3) was observed in one patient only. The most frequently reported Grade 3 or Grade 4 AE was neutropenia (10.4% of pts). One patient discontinued treatment due to AEs (renal failure and disease progression). One Grade 5 (fatal) AE was observed (sudden death, due to natural causes per investigator assessment).

TABLE 11

Summary of Adverse Events

| N (%) | 1L DLBCL (N = 48) |
|---|---|
| AEs with incidence ≥10% by preferred term | 45 (93.8) |
| CRS | 14 (29.2) |

TABLE 11-continued

Summary of Adverse Events

| N (%) | 1L DLBCL (N = 48) |
|---|---|
| Fatigue | 9 (18.8) |
| Abdominal pain | 7 (14.6) |
| Chills | 5 (10.4) |
| Rash maculo-papular | 5 (10.4) |
| Neutropenia | 5 (10.4) |
| Decreased appetite | 5 (10.4) |
| Grade 3-4 AEs with incidence ≥5% by preferred term | 17 (35.4) |
| Neutropenia | 5 (10.4) |
| Serious AEs | 17 (35.4) |
| Grade 5 (fatal) AEs | 1 (2.1) |
| AEs leading to discontinuation | 1 (2.1) |

All CRA events experienced by pts are summarized in Table 12 and FIG. 7. All CR events (Lee et al. 2019 criteria; ASTCT® criteria) were Grade 1 or Grade 2 and only occurred during the first cycle of mosunetuzumab. The most frequent CRS symptoms were pyrexia (11/14 pts, 78.6%) and chills (6/14 pts, 42.9%). Grade 2 CRS events (4/14 pts) were treated with supportive care in all pts and steroids in one patient. No pressors or tocilizumab were used, and no treatment in the intensive care unit was required.

TABLE 12

Summary of CRS Events, as Defined by ASTCT ® Criteria (Lee et al. 2019)

| N (%), unless otherwise stated | 1L DLBCL (N = 48) |
|---|---|
| Any Grade CRS | 14 (29.2) |
| Grade 1 CRS | 10 (20.8) |
| Grade 2 CRS | 4 (8.3) |
| Grade ≥3 CRS | 0 |
| Use of tocilizumab for CRS, N (%) | 0 |
| Median time to onset, days (range) | 1 (1-2) |
| Median duration, days (range) | 1 (1-2) |

Mosunetuzumab monotherapy was efficacious in older and/or unfit pts. Median duration of follow-up was 9.4 months (range: 0.2-22.7 months), although follow-up for some pts in the expansion cohort was very limited. ORRs and CR rates in efficacy-evaluable pts were 61.5% (24/39) and 43.6% (17/39), respectively (Table 13). Duration of responses were analyzed and reported for all patients in the present study. Durations of response were initially analyzed with a data cut-off date of Jan. 15, 2021, and results are shown in FIG. 8A. Data for durations of response were analyzed a second time with a data cut-off date of Apr. 12, 2021, and reported in FIG. 8B. As shown in FIG. 8B, by Apr. 21, 2021, eight of 17 pts with CR had a follow-up of ≥12 months and maintained a complete remission.

TABLE 13

Best Overall Response by Investigator in Efficacy-Evaluable Patients (Assessed by PET-CT After 4 or 8 Cycles Using Lugano 2014 Criteria)

| N (%) | ORR | CR rate | PR rate | SD rate | PD rate |
|---|---|---|---|---|---|
| All patients (N = 39) | 24 (61.5) | 17 (43.6) | 7 (17.9) | 1 (2.6) | 9 (23.1) |
| 13.5 mg cohort (N = 8) | 6 (75.0) | 4 (50.0) | 2 (25.0) | 0 | 2 (25.0) |

TABLE 13-continued

Best Overall Response by Investigator in Efficacy-Evaluable Patients
(Assessed by PET-CT After 4 or 8 Cycles Using Lugano 2014 Criteria)

| N (%) | ORR | CR rate | PR rate | SD rate | PD rate |
|---|---|---|---|---|---|
| 30 mg cohort (N = 31) | 18 (58.1) | 13 (41.9) | 5 (16.1) | 1 (3.2) | 7 (22.6) |

ORR = overall response rate;
CR = complete response;
PR = partial response;
SD = stable disease;
PD = progressive disease.

Pharmacodynamic changes in peripheral blood in Cycle 1, including T-cell activation and cytokine production, were similar between elderly/unfit pts with previously untreated DLBCL who received mosunetuzumab monotherapy in the current study and fit pts with previously untreated DLBCL who received mosunetuzumab-CHOP in an ongoing Phase Ib/II study (NCT03677141). See FIGS. 9A-9C.

D. Conclusions

Mosunetuzumab monotherapy has a favorable toxicity profile in older and/or unfit pts with previously untreated DLBCL. CRS events were Grade 1 or Grade 2 and were limited to Cycle 1. Mosunetuzumab continues to show promising efficacy as monotherapy in previously untreated elderly/unfit pts, with durable CRs observed. These data suggest a potential future role for mosunetuzumab, as monotherapy or in chemotherapy-free or chemotherapy-light combinations, in older and/or unfit pts with previously untreated DLBCL who are considered unsuitable for standard R-CHOP therapy.

OTHER EMBODIMENTS

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method of treating an elderly or unfit subject having a previously untreated B cell proliferative disorder comprising intravenously administering to the subject, as a monotherapy, mosunetuzumab in a dosing regimen comprising at least a first dosing cycle and a second dosing cycle, wherein:

(a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and (b) the second dosing cycle comprises a single dose (C2D1) of the mosunetuzumab, wherein the C2D1 is the same dose as the C1D3, wherein:

(a) the elderly subject is at least 80-years old; or (b) the unfit subject is at least 60-years old, and wherein the unfit subject exhibits:

(i) an impairment in at least one activity of daily living (ADL) component;

(ii) an impairment in at least one instrumental activity of daily living (IADL) component;

(iii) an impairment in at least one of cardiac function, vascular function, renal function, and/or liver function; and/or (iv) diabetes.

2. The method of claim 1, wherein:

(i) the impairment in cardiac function comprises heart arrhythmia, congestive heart failure (CHF), myocardial infarction, and/or cardiac-related symptoms of hypothyroidism;

(ii) the impairment in vascular function comprises anemia, cerebrovascular accident (CVA), cerebrovascular disease (CVD), chronic obstructive pulmonary disease not otherwise specified (COPD: NOS), hyperlipidemia, peripheral vascular disease, stroke, and/or ischemic attack (TIA);

(iii) the impairment in renal function comprises acute kidney disease and/or chronic kidney disease; and/or (iv) diabetes comprises type 2 diabetes, diabetes with end organ damage (EOD), and/or diabetes without EOD.

3. The method of claim 1, wherein the subject is unsuitable for treatment with R-CHOP therapy.

4. A method of treating a subject having a previously untreated B cell proliferative disorder comprising intravenously administering to the subject, as a monotherapy, mosunetuzumab in a dosing regimen comprising at least a first dosing cycle and a second dosing cycle, wherein:

(a) the first dosing cycle comprises a first dose (C1D1), a second dose (C1D2), and a third dose (C1D3) of the mosunetuzumab, wherein the C1D1 is 1 mg, the C1D2 is 2 mg, and the C1D3 is 13.5 or 30 mg; and (b) the second dosing cycle comprises a single dose (C2D1) of the mosunetuzumab, wherein the C2D1 is the same dose as the C1D3, wherein the subject is unsuitable for treatment with R-CHOP therapy.

5. The method of claim 3, wherein the R-CHOP therapy comprises rituximab, cyclophosphamide, doxorubicin, vincristine, and prednisone, and further wherein the rituximab is administered to the subject at a dose of 375 mg/m² every three weeks.

6. The method of claim 1, wherein:

(a) the first and second dosing cycles are 21-day dosing cycles;

(b) the method comprises administering the C2D1 on Day 1 of the second dosing cycle;

(c) the dosing regimen further comprises one or more additional dosing cycles; and/or (d) the method further comprises administering to the subject one or more additional therapeutic agents to treat or reduce the likelihood of a cytokine release syndrome (CRS) event or a tumor lysis syndrome (TLS) event.

7. The method of claim 6, wherein the method comprises administering the C1D1, the C1D2, and the C1D3 on Days 1, 8, and 15, respectively, of the first dosing cycle.

8. The method of claim 6, wherein:

(a) the dosing regimen comprises six or 15 additional dosing cycles;

(b) the additional dosing cycles are 21-day dosing cycle; and/or (c) one or more of the additional dosing cycles comprise an additional single dose of the mosunetuzumab.

9. The method of claim 8, wherein the additional single dose of the mosunetuzumab is:

(a) administered to the subject on Day 1 of each additional dosing cycle; and/or (b) the same dose as the C1D3.

10. The method of claim 6, wherein the one or more additional therapeutic agents is:

(a) tocilizumab;

(b) an antihistamine;

(c) allopurinol or rasburicase; and/or (d) a corticosteroid.

11. The method of claim 10, wherein:

(a) the antihistamine is diphenhydramine; and/or (b) the corticosteroid comprises prednisone, prednisolone, methylprednisolone, and dexamethasone.

12. The method of claim 11, wherein the corticosteroid comprises prednisone, and wherein prednisone is administered to the subject:

(a) on each of the seven days prior to the administration of the C1D1; and/or (b) at a dose of 100 mg/day.

13. The method of claim 1 wherein the previously untreated B cell proliferative disorder is a previously untreated high-grade B-cell lymphoma and/or a previously untreated non-Hodgkin's lymphoma (NHL).

14. The method of claim 13, wherein the previously untreated NHL is a previously untreated DLBCL.

15. A method of treating a population of subjects having a previously untreated DLBCL comprising intravenously administering to the subjects, as a monotherapy, mosunetuzumab in a dosing regimen comprising eight 21-day dosing cycles, wherein:

(a) the first dosing cycle comprises a first dose (C1D1), a second dose (C1D2), and a third dose (C1D3) of the mosunetuzumab administered on Days 1, 8, and 15, respectively, of the first dosing cycle, wherein the C1D1 is 1 mg, the C1D2 is 2 mg, and the C1D3 is 13.5 or 30 mg; and (b) the second to eighth dosing cycles each comprises a single dose (C2D1-C8D1) of the mosunetuzumab administered on Day 1 of each dosing cycle, wherein each single dose C2D1-C8D1 is the same dose as the C1D3, wherein the subjects are at least 65-years old, and wherein the subjects are unsuitable for treatment with R-CHOP therapy.

16. A method of treating a population of subjects having a previously untreated DLBCL comprising intravenously administering to the subjects, as a monotherapy, mosunetuzumab in a dosing regimen comprising seventeen 21-day dosing cycles, wherein:

(a) the first dosing cycle comprises a first dose (C1D1), a second dose (C1D2), and a third dose (C1D3) of the mosunetuzumab administered on Days 1, 8, and 15, respectively, of the first dosing cycle, wherein the C1D1 is 1 mg, the C1D2 is 2 mg, and the C1D3 is 13.5 or 30 mg; and (b) the second to seventeenth dosing cycles each comprises a single dose (C2D1-C17D1) of the mosunetuzumab administered on Day 1 of each dosing cycle, wherein each single dose C2D1-C17D1 is the same dose as the C1D3, wherein the subjects are at least 65-years old, and wherein the subjects are unsuitable for treatment with R-CHOP therapy.

17. The method of claim 15, wherein (a) the overall response rate is greater than 56%;

(b) the complete response rate is greater than 38%; and/or (c) the rate of cytokine release syndrome having a grade of 3 or higher is less than 5%.

18. The method of claim 16, wherein:

(a) the overall response rate is greater than 56%;

(b) the complete response rate is greater than 38%; and/or (c) the rate of cytokine release syndrome having a grade of 3 or higher is less than 5%.

19. The method of claim 17, wherein greater than 42% of subjects having a complete response maintained complete remission for 12 months.

20. The method of claim 18, wherein greater than 42% of subjects having a complete response maintained complete remission for 12 months.

21. A method of treating a subject having a previously untreated DLBCL comprising intravenously administering to the subject, as a monotherapy, mosunetuzumab in a dosing regimen comprising eight 21-day dosing cycles, wherein:

(a) the first dosing cycle comprises a first dose (C1D1), a second dose (C1D2), and a third dose (C1D3) of mosunetuzumab administered on Days 1, 8, and 15, respectively, of the first dosing cycle, wherein the C1D1 is 1 mg, the C1D2 is 2 mg, and the C1D3 is 30 mg; and (b) the second to eighth dosing cycles each comprises a single dose (C2D1-C8D1) of mosunetuzumab administered on Day 1 of each dosing cycle, wherein each single dose C2D1-C8D1 is the same dose as the C1D3, wherein the subject is at least 65-years old, and wherein the subject is unsuitable for treatment with standard R-CHOP therapy.

22. A method of treating a subject having a previously untreated DLBCL comprising intravenously administering to the subject, as a monotherapy, mosunetuzumab in a dosing regimen comprising seventeen 21-day dosing cycles, wherein:

(a) the first dosing cycle comprises a first dose (C1D1), a second dose (C1D2), and a third dose (C1D3) of mosunetuzumab administered on Days 1, 8, and 15, respectively, of the first dosing cycle, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab administered on Day 1 of each dosing cycle, wherein each single dose C2D1-C17D1 is the same dose as the C1D3, wherein the subject is at least 65-years old, and wherein the subject is unsuitable for treatment with standard R-CHOP therapy.

23. A method of treating an elderly subject having a previously untreated DLBCL comprising intravenously administering to the subject, as a monotherapy, mosunetuzumab in a dosing regimen comprising eight 21-day dosing cycles, wherein:

(a) the first dosing cycle comprises a first dose (C1D1), a second dose (C1D2), and a third dose (C1D3) of mosunetuzumab administered on Days 1, 8, and 15, respectively, of the first dosing cycle, wherein the C1D1 is 1 mg, the C1D2 is 2 mg, and the C1D3 is 30 mg; and (b) the second to eighth dosing cycles each comprises a single dose (C2D1-C8D1) of mosunetuzumab administered on Day 1 of each dosing cycle, wherein each single dose C2D1-C8D1 is the same dose as the C1D3, wherein the subject is at least 80-years old.

24. A method of treating an elderly subject having a previously untreated DLBCL comprising intravenously administering to the subject, as a monotherapy, mosunetuzumab in a dosing regimen comprising seventeen 21-day dosing cycles, wherein:

(a) the first dosing cycle comprises a first dose (C1D1), a second dose (C1D2), and a third dose (C1D3) of mosunetuzumab administered on Days 1, 8, and 15, respectively, of the first dosing cycle, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab administered on Day 1 of each dosing cycle, wherein each single dose C2D1-C17D1 is the same dose as the C1D3, wherein the subject is at least 80-years old.

25. A method of treating an unfit subject having a previously untreated DLBCL comprising intravenously administering to the subject, as a monotherapy, mosunetuzumab in a dosing regimen comprising eight 21-day dosing cycles, wherein:

(a) the first dosing cycle comprises a first dose (C1D1), a second dose (C1D2), and a third dose (C1D3) of mosunetuzumab administered on Days 1, 8, and 15, respectively, of the first dosing cycle, wherein the C1D1 is 1 mg, the C1D2 is 2 mg, and the C1D3 is 30 mg; and (b) the second to eighth dosing cycles each comprises a single dose (C2D1-C8D1) of mosunetuzumab administered on Day 1 of each dosing cycle, wherein each single dose C2D1-C8D1 is the same dose as the C1D3, wherein the subject is at least 60-years old, and wherein the subject exhibits:

(i) an impairment in at least one ADL component;

(ii) an impairment in at least one IADL component;

(iii) an impairment in at least one of cardiac function, vascular function, renal function, and/or liver function; and/or (iv) diabetes.

26. A method of treating an unfit subject having a previously untreated DLBCL comprising intravenously administering to the subject, as a monotherapy, mosunetuzumab in a dosing regimen comprising seventeen 21-day dosing cycles, wherein:

(a) the first dosing cycle comprises a first dose (C1D1), a second dose (C1D2), and a third dose (C1D3) of mosunetuzumab administered on Days 1, 8, and 15, respectively, of the first dosing cycle, wherein the C1D1 is 1 mg, the C1D2 is 2 mg, and the C1D3 is 30 mg; and (b) the second to seventeenth dosing cycles each comprises a single dose (C2D1-C17D1) of mosunetuzumab administered on Day 1 of each dosing cycle, wherein each single dose C2D1-C17D1 is the same dose as the C1D3, wherein the subject is at least 60-years old, and wherein the subject exhibits:

(i) an impairment in at least one ADL component;

(ii) an impairment in at least one IADL component;

(iii) an impairment in at least one of cardiac function, vascular function, renal function, and/or liver function; and/or (iv) diabetes.

* * * * *